(12) United States Patent
Belhe et al.

(10) Patent No.: US 8,702,642 B2
(45) Date of Patent: *Apr. 22, 2014

(54) EXTERNAL ANCHORING CONFIGURATIONS FOR MODULAR GASTROINTESTINAL PROSTHESES

(75) Inventors: Kedar R. Belhe, Minnetonka, MN (US); Paul J. Thompson, Minnetonka, MN (US)

(73) Assignee: MetaModix, Inc., Plymouth, MN (US)

( * ) Notice: Subject to any disclaimer, the term of this patent is extended or adjusted under 35 U.S.C. 154(b) by 5 days.

This patent is subject to a terminal disclaimer.

(21) Appl. No.: 13/568,101

(22) Filed: Aug. 6, 2012

(65) Prior Publication Data

US 2012/0302936 A1 Nov. 29, 2012

Related U.S. Application Data

(63) Continuation of application No. 12/833,605, filed on Jul. 9, 2010, now Pat. No. 8,282,598.

(60) Provisional application No. 61/270,588, filed on Jul. 10, 2009.

(51) Int. Cl.
*A61F 2/04* (2013.01)

(52) U.S. Cl.
USPC .................. 604/8; 604/175; 604/909; 600/37

(58) Field of Classification Search
None
See application file for complete search history.

(56) References Cited

U.S. PATENT DOCUMENTS

| 4,134,405 A | 1/1979 | Smit |
|---|---|---|
| 4,204,530 A | 5/1980 | Finney |
| 4,246,893 A | 1/1981 | Berson |
| 4,314,405 A | 2/1982 | Park |
| 4,315,509 A | 2/1982 | Smit |
| 4,416,267 A | 11/1983 | Garren et al. |
| 4,501,264 A | 2/1985 | Rockey |
| 4,641,653 A | 2/1987 | Rockey |
| 4,716,900 A | 1/1988 | Ravo et al. |
| 4,719,916 A | 1/1988 | Ravo |
| 4,763,653 A | 8/1988 | Rockey |

(Continued)

FOREIGN PATENT DOCUMENTS

| AU | 2006227471 B2 | 9/2006 |
|---|---|---|
| CN | 1618411 A | 5/2005 |

(Continued)

OTHER PUBLICATIONS

International Search Report and Written Opinion issued in PCT/US12/58202, mailed Jan. 23, 2013, 14 pages.

(Continued)

*Primary Examiner* — Jackie Ho
*Assistant Examiner* — Eric Bryant
(74) *Attorney, Agent, or Firm* — Faegre Baker Daniels LLP

(57) ABSTRACT

Components may be used separately or in combination to create anchoring systems for intra-luminal implants for the treatment of metabolic disorders such as obesity and diabetes. Various systems include an external component adapted for deployment around a portion of the gastrointestinal tract (e.g., the duodenum) and an internal component adapted for implantation within the gastrointestinal tract. Various systems use anchors that are based on mechanical interference, elasticity, spring force, shape memory transformation, magnetic attraction, repulsion and/or levitation. Various embodiments rely on longitudinal anchoring of the implants with minimal force against tissue.

16 Claims, 52 Drawing Sheets

(56) References Cited

U.S. PATENT DOCUMENTS

| | | |
|---|---|---|
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,749,921 A | 5/1998 | Lenker et al. |
| 5,753,253 A | 5/1998 | Meyer |
| 5,820,584 A | 10/1998 | Crabb |
| 6,017,563 A | 1/2000 | Knight et al. |
| 6,267,988 B1 | 7/2001 | Meyer |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 * | 1/2008 | Egan ................... 623/23.65 |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Levine et al. |
| 8,114,045 B2 | 2/2012 | Surti |
| 8,211,186 B2 | 7/2012 | Belhe et al. |
| 8,282,598 B2 | 10/2012 | Belhe et al. |
| 2002/0183768 A1 | 12/2002 | Deem et al. |
| 2002/0188354 A1 | 12/2002 | Peghini |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1 * | 5/2004 | Kagan et al. ................... 604/264 |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |
| 2005/0022827 A1 | 2/2005 | Woo et al. |
| 2005/0033331 A1 | 2/2005 | Burnett et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |

(56) References Cited

U.S. PATENT DOCUMENTS

| | | |
|---|---|---|
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0118749 A1* | 5/2009 | Shalon et al. ............. 606/157 |
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0256775 A1 | 10/2010 | Belhe et al. |
| 2010/0305590 A1 | 12/2010 | Holmes et al. |
| 2011/0009690 A1 | 1/2011 | Belhe et al. |
| 2011/0106273 A1 | 5/2011 | Belhe et al. |
| 2012/0065571 A1 | 3/2012 | Thompson et al. |
| 2012/0184893 A1 | 7/2012 | Thompson et al. |
| 2012/0253259 A1 | 10/2012 | Belhe et al. |
| 2012/0253260 A1 | 10/2012 | Belhe et al. |
| 2013/0030351 A1 | 1/2013 | Belhe et al. |

FOREIGN PATENT DOCUMENTS

| | | |
|---|---|---|
| EP | 0137878 A1 | 4/1985 |
| EP | 1420730 A2 | 5/2004 |
| EP | 1492477 A1 | 1/2005 |
| EP | 1492478 A1 | 1/2005 |

(56) References Cited

FOREIGN PATENT DOCUMENTS

| | | |
|---|---|---|
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1881781 A2 | 1/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| WO | WO9849943 A2 | 11/1998 |
| WO | WO02096327 A2 | 12/2002 |
| WO | WO03017882 A2 | 3/2003 |
| WO | WO03086246 A1 | 10/2003 |
| WO | WO03086247 A1 | 10/2003 |
| WO | WO03094785 A1 | 11/2003 |
| WO | WO2004011085 A1 | 2/2004 |
| WO | WO2004017863 A2 | 3/2004 |
| WO | WO2004041133 A1 | 5/2004 |
| WO | WO2004064680 A1 | 8/2004 |
| WO | WO2004064685 A1 | 8/2004 |
| WO | WO2004087014 A2 | 10/2004 |
| WO | WO2004087233 A2 | 10/2004 |
| WO | WO2004049982 B1 | 12/2004 |
| WO | WO2005037152 A1 | 4/2005 |
| WO | WO 2005/037152 * 4/2005 ............... A61F 5/00 |
| WO | WO2005058415 A2 | 6/2005 |
| WO | WO2005060869 A2 | 7/2005 |
| WO | WO2005060882 A1 | 7/2005 |
| WO | WO2005065412 A2 | 7/2005 |
| WO | WO2005097012 A2 | 10/2005 |
| WO | WO2005099591 A2 | 10/2005 |
| WO | WO2005110244 A1 | 11/2005 |
| WO | WO2005110280 A2 | 11/2005 |
| WO | WO2005112822 A1 | 12/2005 |
| WO | WO2005120363 A1 | 12/2005 |
| WO | WO2006014496 A2 | 2/2006 |
| WO | WO2006016894 A1 | 2/2006 |
| WO | WO2006020370 A2 | 2/2006 |
| WO | WO2006028898 A2 | 3/2006 |
| WO | WO2006034062 A1 | 3/2006 |
| WO | WO2006060049 A2 | 6/2006 |
| WO | WO2006062996 A2 | 6/2006 |
| WO | WO2006078781 A1 | 7/2006 |
| WO | WO2006078927 A1 | 7/2006 |
| WO | WO2006102012 A1 | 9/2006 |
| WO | WO2006102240 A2 | 9/2006 |
| WO | WO2006124880 A2 | 11/2006 |
| WO | WO2006127593 A2 | 11/2006 |
| WO | WO2006133311 A2 | 12/2006 |
| WO | WO2007019117 A1 | 2/2007 |
| WO | WO2007030829 A2 | 3/2007 |
| WO | WO2007038715 A1 | 4/2007 |
| WO | WO2007041598 A1 | 4/2007 |
| WO | WO2007075396 A2 | 7/2007 |
| WO | WO2007092390 A2 | 8/2007 |
| WO | WO2007107990 A2 | 9/2007 |
| WO | WO2007127209 A2 | 11/2007 |
| WO | WO2007136468 A2 | 11/2007 |
| WO | WO2007139920 A2 | 12/2007 |
| WO | WO2007142829 A1 | 12/2007 |
| WO | WO2007142832 A1 | 12/2007 |
| WO | WO2007142833 A1 | 12/2007 |
| WO | WO2007142834 A1 | 12/2007 |
| WO | WO2007145684 A2 | 12/2007 |
| WO | WO2008005510 A2 | 1/2008 |
| WO | WO2008030403 A1 | 3/2008 |
| WO | WO2008033409 A1 | 3/2008 |
| WO | WO2008033474 A2 | 3/2008 |
| WO | WO2008039800 A2 | 4/2008 |
| WO | WO2008101048 A2 | 8/2008 |
| WO | WO2008106041 A1 | 9/2008 |
| WO | WO2008106279 A1 | 9/2008 |
| WO | WO2008112942 A2 | 9/2008 |
| WO | WO2008127552 A2 | 10/2008 |
| WO | WO2008141288 A1 | 11/2008 |
| WO | WO2008148047 A2 | 12/2008 |
| WO | WO2008150905 A1 | 12/2008 |
| WO | WO2008154450 A1 | 12/2008 |
| WO | WO2008154594 A2 | 12/2008 |
| WO | WO2009011881 A1 | 1/2009 |
| WO | WO2009011882 A2 | 1/2009 |
| WO | WO2009012335 A1 | 1/2009 |
| WO | WO2009036244 A1 | 3/2009 |
| WO | WO2009046126 A1 | 4/2009 |
| WO | WO2009082710 A1 | 7/2009 |
| WO | WO2009085107 A1 | 7/2009 |
| WO | WO2009086549 A1 | 7/2009 |
| WO | WO2009097582 A1 | 8/2009 |
| WO | WO2009097585 A1 | 8/2009 |
| WO | WO2010115011 A1 | 10/2010 |
| WO | WO2011062882 A1 | 5/2011 |
| WO | WO2011073970 A1 | 6/2011 |
| WO | WO2011099940 A8 | 8/2011 |

OTHER PUBLICATIONS

Buchwald, Henry et al., "Bariatric Surgery: A Systematic Review and Meta-Analysis", JAMA, Oct. 13, 2004, 292 (14), pp. 1724-1737.

Cummings, David E. et al., "Role of the bypassed proximal intestine in the anti-diabetic effects of bariatric surgery", Surgery for Obesity and Related Diseases 3 2007, pp. 109-115.

International Search Report and Written Opinion issued in PCT/US2010/029648, mailed Aug. 24, 2010.

International Search Report and Written Opinion issued in PCT/US2010/041574, mailed Jan. 25, 2011.

International Search Report and Written Opinion issued in PCT1US2011/020560, mailed Mar. 28, 2011, 10 pages.

International Search Report and Written Opinion issued in PCT/US2011/061193 mailed Mar. 9, 2012.

International Search Report and Written Opinion issued in PCT/US2012/023048, mailed Jun. 22, 2012.

Invitation to Pay Additional Fees issued in PCT/US2010/029648, mailed Jun. 1, 2010.

Pories, Walter J. et al., "Surgical Treatment of Obesity and its Effect on Diabetes: 10-6 Follow-up", Am J Clin Nutr 1992, 55, 582S-585S.

Pories, Walter J. et al., "Who Would Have Thought It? An Operation Proves to be the Most Effective Therapy for Adult-Onset Diabetes Mellitus", Annals of Survery, Sep. 1995, 222(3), pp. 339-352.

Rodriguez-Grunert, Leonardo et al., "First Human Experience with endoscopically Delivered and retrieved duodenal-jejunal bypass sleeve", Surgery for Obesity and Related diseases 4 (2008) 55-59.

Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.

(56) References Cited

OTHER PUBLICATIONS

Rubino, Francesco et al., "Potential of Surgery for Curing Type 2 Diabetes Mellitus", Annals of Surgery, Nov. 2002, 236(5), 554-559.

Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.

Strader, April et al., "Weight Loss Through Ileal transposition is accompanied by increased ileal hormone secretion and synthesis in rats", Am J Physiol Endocrinol Metab 288: E447-E453, 2005.

Troy, Stephanie et al., "Intestinal Gluconeogenesis is a key factor for early metabolic changes after gastric bypass but not after gastric lap-band in mice", Cell metabolism 8, 201-211, Sep. 3, 2008.

Vetter, Marion et al., "Narrative Review: Effect of bariatric Surgery on Type 2 Diabetes Mellitus", Annals of Internal Medicine, Jan. 20, 2009, 150(2), pp. 94-104.

\* cited by examiner

EXTERNAL ANCHORING CONFIGURATIONS FOR MODULAR GASTROINTESTINAL PROSTHESES

CROSS-REFERENCE(S) TO RELATED APPLICATION

This application is a continuation of U.S. patent application Ser. No. 12/833,605, filed Jul. 9, 2010, and since patented having U.S. Pat. No. 8,282,598, entitled "External Anchoring Configurations for Modular Gastrointestinal Prostheses," which claims the benefit under 35 U.S.C. §119(e) to U.S. provisional application 61/270,588, filed Jul. 10, 2009, both of which are incorporated herein by reference in their entirety.

TECHNICAL FIELD

This invention generally relates to implants placed within gastrointestinal systems, including the esophagus, the stomach and the intestines. In particular, it relates to implant systems having components implantable and removable using laparoscopic and endoscopic techniques for treatment of obesity, diabetes, reflux, and other gastrointestinal conditions.

BACKGROUND

Bariatric surgery procedures, such as sleeve gastrectomy, the Rouen-Y gastric bypass (RYGB) and the bileo-pancreatic diversion (BPD), modify food intake and/or absorption within the gastrointestinal system to effect weight loss in obese patients. These procedures affect metabolic processes within the gastrointestinal system by either short-circuiting certain natural pathways or creating different interaction between the consumed food, the digestive tract, its secretions and the neuro-hormonal system regulating food intake and metabolism. In the last few years, there has been a growing clinical consensus that obese diabetic patients who undergo bariatric surgery see a remarkable resolution of their Type-2 Diabetes Mellitus (T2DM) soon after the procedure. The remarkable resolution of diabetes after RYGB and BPD typically occurs too fast to be accounted for by weight loss alone, suggesting that there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there is an increasing amount of ongoing effort to develop minimally invasive procedures to mimic the effects of bariatric surgery using minimally invasive procedures. One such procedure involves the use of gastrointestinal implants that modify transport and absorption of food and organ secretions. For example, U.S. Pat. No. 7,476,256 describes an implant having a tubular sleeve with an anchor having barbs. While these implants may be delivered endoscopically, the implants offer the physician limited flexibility and are not readily removable or replaceable, since the entire implant is subject to tissue in-growth after implantation. Moreover, stents with active fixation means, such as barbs that penetrate into the surrounding tissue, may potentially cause tissue necrosis and erosion of the implants through the tissue, which can lead to serious complications, such as systemic infection. Also, due to the intermittent peristaltic motion within the digestive tract, implants such as stents have a tendency to migrate.

SUMMARY

According to various embodiments, the present invention is a gastrointestinal implant system for treating metabolic disorders, such as diabetes and obesity. The system includes a tubular implant adapted for placement within at least a portion of the duodenum, the tubular implant having a securing feature and an external band configured for implantation around at least one of a pylorus, and a duodenum, the external band having a coupling feature for removably engaging and coupling with the securing feature of the internal tubular implant without penetrating the duodenum or pylorus, such that the therapeutic implant resists migration within the gastrointestinal tract, wherein the external band has an inner diameter generally equal to a corresponding outer diameter of the duodenum or pylorus, and the securing feature and coupling feature are configured such that the tubular implant is releasably coupled to the external band to facilitate removal of the tubular implant.

According to various embodiments, the present invention is a modular gastrointestinal implant system for treating metabolic conditions, such as diabetes and obesity. The system includes an external implant configured for affixing around at least a portion of a duodenum or pylorus, the external implant having a docking feature, and a therapeutic implant adapted for placement within a gastrointestinal tract, the therapeutic implant having a securing feature adapted to removably couple with the docking feature without penetrating the gastrointestinal tract, such that the therapeutic implant resists migration within the gastrointestinal tract, wherein the external band has a diameter generally equal to the diameter of the duodenum or pylorus.

According to other exemplary embodiments, the present invention is a method of treating metabolic conditions, such as diabetes and obesity. The method includes placing an external implant around at least a portion of the duodenum, the external implant having a docking feature and the external implant having an inner diameter generally equal to an outer diameter of the corresponding portion of the esophagus, implanting, using a minimally-invasive technique, an internal tubular implant having a securing feature to a location within the duodenum corresponding to the location of the external implant, and causing the securing feature to removably couple with the docking feature without penetrating the duodenum.

According to various disclosed embodiments, systems for anchoring intra-luminal implants within hollow body organs (e.g., the gastrointestinal organs) include an external fixation mechanism that can be delivered to an external surface of the organ (e.g., by laparoscopic techniques) and an intra-luminal implant configured to engage with the external fixation means, without the need for excessive radial force on the organ and without penetrating the tissue. According to various embodiments, the fixation mechanisms operate using techniques such as shape modification of the organ to capture the implant longitudinally or magnetic attraction, repulsion or levitation of the implant. Various embodiments of the present invention are useful for treating metabolic conditions, including for example, diabetes and obesity.

The present invention according to various embodiments is a modular system for creating internal bypass of food and organ secretions within the gastrointestinal tract that includes low-profile implants that are affixed around the stomach, the esophagus, the intestine or externally around junctions of these organs, and gastrointestinal implants that permit internal by-pass of food and organ secretions from one site within the gastrointestinal tract to other sites within the gastrointestinal tract that have complementary design features to the external implant that enables secure placement within the gastrointestinal tract.

The present invention according to various embodiments is a modular system for creating a completely reversible internal bypass of food and organ secretions within the gastrointestinal tract that includes low-profile implants that are affixed around the stomach, the esophagus, the intestine or externally around junctions of these organs and which enable secure attachment of other implants within the gastrointestinal tract, and gastrointestinal implants that permit internal by-pass of food and organ secretions from one site within the gastrointestinal tract to other sites within the gastrointestinal tract that have complementary design features to the external implant that enables secure placement within the gastrointestinal tract.

The present invention according to various embodiments is a modular system for treating gastro-esophageal reflux disease (GERD) that includes low-profile implants that are affixed around the stomach, the esophagus, the intestine or externally around junctions of these organs and which enable secure attachment of other implants within the gastrointestinal tract, and an internal tubular implant of a design that normally permits only one-way passage of food from the esophagus to the stomach and that can be secured within the gastrointestinal tract by the external low-profile implant.

The present invention according to various embodiments is a method for creating a reversible treatment for metabolic disorders, such as diabetes and obesity, and for the treatment of gastro-esophageal reflux disease (GERD), including placing low-profile implants that can be affixed around the stomach, the esophagus, the intestine or externally around junctions of these organs and which enable secure attachment of other implants within the gastrointestinal tract, and placing other gastrointestinal implants that permit internal by-pass of food and organ secretions from one site within the gastrointestinal tract to other sites within the gastrointestinal tract, which do not directly anchor to the tissue but are securely held by the external implant so that the procedure can be reversed easily.

The present invention according to various embodiments is a method of treating metabolic disorders, such as obesity and diabetes, by placing a permanently band like structure around the esophagus, the stomach, the intestine or externally around junctions of these organs, and endoscopically placing a long tubular sleeve within the GI tract with expandable elements at its ends, those expandable elements having design functionality that enables it to be reversibly secured in position by the external band.

The present invention according to various embodiments is a method for creating a gastrointestinal bypass, the method including delivering a band like structure at appropriate locations around the gastrointestinal tract, such as the esophagus, the stomach, the duodenal bulb, the pyloric junction, the gastro-esophageal junction, etc.; and delivering a tubular sleeve with expandable ring shaped elements at its ends, those rings having outward indentations that enable it to be reversibly secured in position by the external band.

According to various embodiments, as a second mode of anchoring, stabilizing, or preventing migration, the external band is coupled to an anatomical feature (e.g., a ligament) external to the tissue of the esophagus, stomach, pylorus, or intestine. In some embodiments, the external band is intertwined with, interlocked with or threaded between the anatomical feature and the tissue. According to one exemplary embodiment, the external band is coupled to the hepatoduodenal ligament. This second mode of anchoring enables the use of external bands that do not rely on excessive compressive force to keep the implant in place, since excessive compressive forces can cause tissue necrosis and erosion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
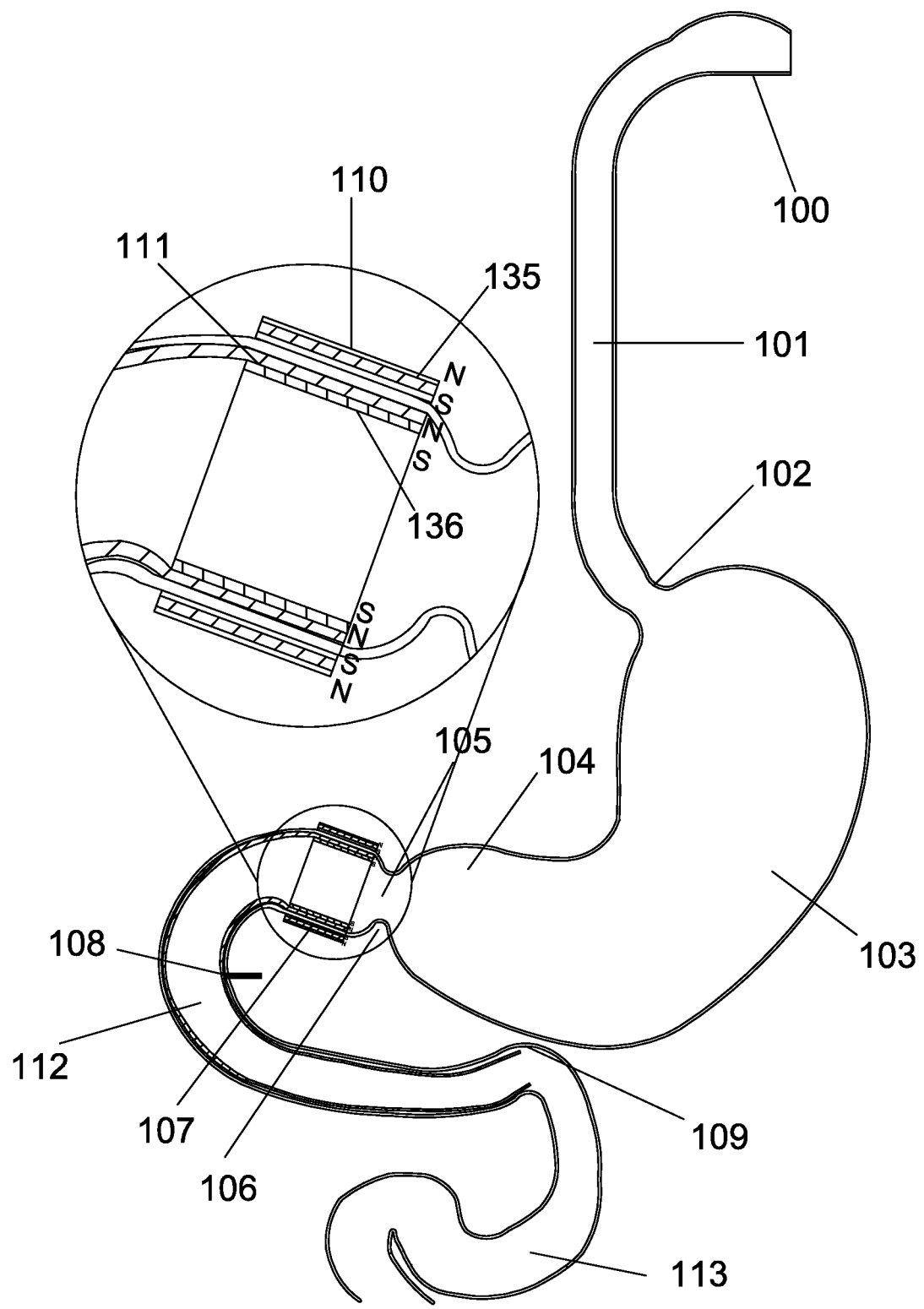
FIG. 1 is a sectional view of a portion of the digestive tract in the body showing an external band implanted around the outside diameter of the duodenal bulb and a tubular implant (sleeve) implanted on the inside surface of the duodenal bulb and anchored magnetically through the duodenal bulb tissue to the external band. The tubular implant extends into the duodenum to the ligament of Treitz.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic, sectional view of a portion of a human digestive tract. As a person ingests food, the food enters the mouth 100, is chewed, and then proceeds down the esophagus 101 to the lower esophageal sphincter at the gastro-esophageal junction 102 and into the stomach 103. The food mixes with enzymes in the mouth 100 and in the stomach 103. The stomach 103 converts the food to a semi-fluid substance called chyme. The chyme enters the pyloric antrum 104 and exits the stomach 103 through the pylorus 106 and pyloric orifice 105. The small intestine is about 21 feet long in adults and is comprised of three sections: the duodenum 112, the jejunum 113 and the ileum (not shown). The duodenum 112 is the first portion of the small intestine and is typically 10-12 inches long. The duodenum 112 is comprised of four sections: the superior, descending, horizontal and ascending. The duodenum 112 ends at the ligament of Treitz 109. The papilla of Vater 108 is the duct that delivers bile and pancreatic enzymes to the duodenum 112. The duodenal bulb 107 is the portion of the duodenum which is closest to the stomach 103.

As shown, an external band 110 is implanted around the duodenal bulb 107 and an internal tubular implant 111 is attached to the external band and extended into the duodenum 112 (e.g., to the ligament of Treitz 109). Magnets 135 on the external band 110 and magnets 136 on the internal tubular implant 111 magnetically interact with (e.g., attraction, repulsion, or levitation) each other and secure the internal tubular implant to the 111 to the external band implant 110 in a removable or reversible configuration. The external band 110 and the internal implant 111 anchor by coupling with each other using any of a variety of techniques including, for example, anchoring means that are based on mechanical interference, elasticity, spring force, shape memory transformation, magnetic attraction, repulsion and/or levitation.

According to some embodiments, the internal implant 111 is configured such that it exerts little or no radial force against an internal surface of the gastrointestinal tract. Likewise, according to various embodiments, the external band is sized and shaped such that, in its final implant configuration, it exerts little or no radial force against an external surface of the gastrointestinal tract. For example, in certain embodiments, the external band has an implanted inner diameter generally equal to an outer diameter of the desired mounting location of the gastrointestinal tract. More specifically, in some such embodiments, the implanted inner diameter of the external band is within ten percent of the corresponding outer diameter of the implant location of the gastrointestinal tract. In other such embodiments, the implanted inner diameter of the external band is within five percent of the corresponding outer diameter of the implant location of the gastrointestinal tract. In other such embodiments, the implanted inner diameter of the external band is within two percent of the corresponding outer diameter of the implant location of the gastrointestinal tract.

According to various embodiments, as a second mode of anchoring, stabilizing, or preventing migration, the external band 110 is coupled to an anatomical feature (e.g., a ligament) external to the tissue of the esophagus, stomach, pylorus, or intestine. In some embodiments, the external band 110 is intertwined with or threaded between the anatomical feature and the tissue. According to one exemplary embodiment, the external band 110 is coupled to the hepatoduodenal ligament. This second mode of anchoring enables the use of external bands that do not rely on excessive compressive force to keep the implant in place, since excessive compressive forces can cause tissue necrosis and erosion.

Figure 2:
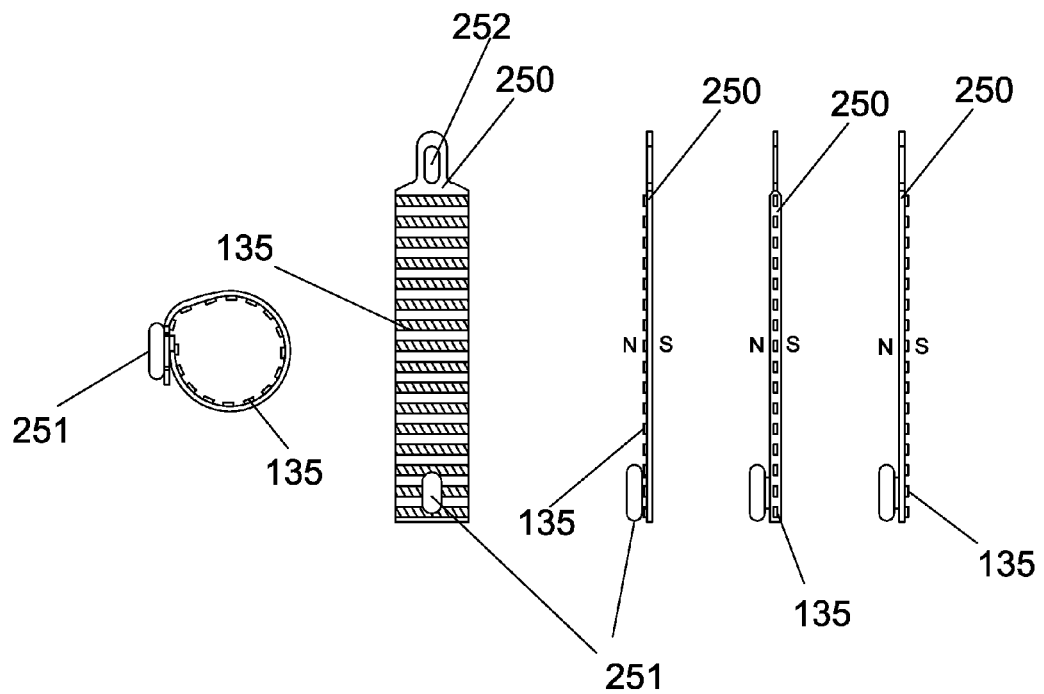
FIGS. 2-7 show various embodiments of an external band that may be used as an external anchoring device to secure an internal tubular implant.

FIG. 2 shows an external band that may be used to provide for an external anchoring device to secure the internal tubular implant. The band 250, according to various embodiments, is made from one or more elastomers (e.g., silicone, polyurethane, and ePTFE), metals or fabrics (e.g., Dacron or a combination of polymers and textile materials). The band can be made flexible with varying degrees of longitudinal elasticity. According to various embodiments, the external band includes magnets 135 located on the inside surface, outside surface, or embedded in the middle of the band. Suitable materials for the magnets include, for example: neodymium-iron-boron [Nd—Fe—B], samarium-cobalt [Sm—Co], alnico, and hard ferrite [ceramic] or other suitable material. The magnets may be plated with gold or platinum or other material to make them radio-opaque or to improve corrosion resistance. The magnets may be encapsulated within a metal casing such as titanium or stainless steel to improve the corrosion resistance and the biocompatibility. As shown in FIG. 2, the magnets 135 are shaped as bars, which may have a length generally similar to the width of the band 250. According to various embodiments, the band is placed around the intended implant location (e.g., the duodenal bulb, esophagus, or stomach). The band, according to various embodiments, is wrapped around the implant location like a belt. As shown, for example, in FIG. 2, one end of the band 250 has a loop 252 and the other end has a button 251. The band is enclosed around the duodenal bulb or other implant location, the loop 252 is snapped over the button 251 to secure the band closed. The magnetic poles of the magnet are aligned such that the all the north poles are aligned to the inside or outside of the band. The magnets on the inside tubular implant are assembled to the device, so the poles are the opposite magnetic polarity, and the outside band and the inside tubular implanted will attract to each other when one device is sleeved inside the other.

Figure 3:
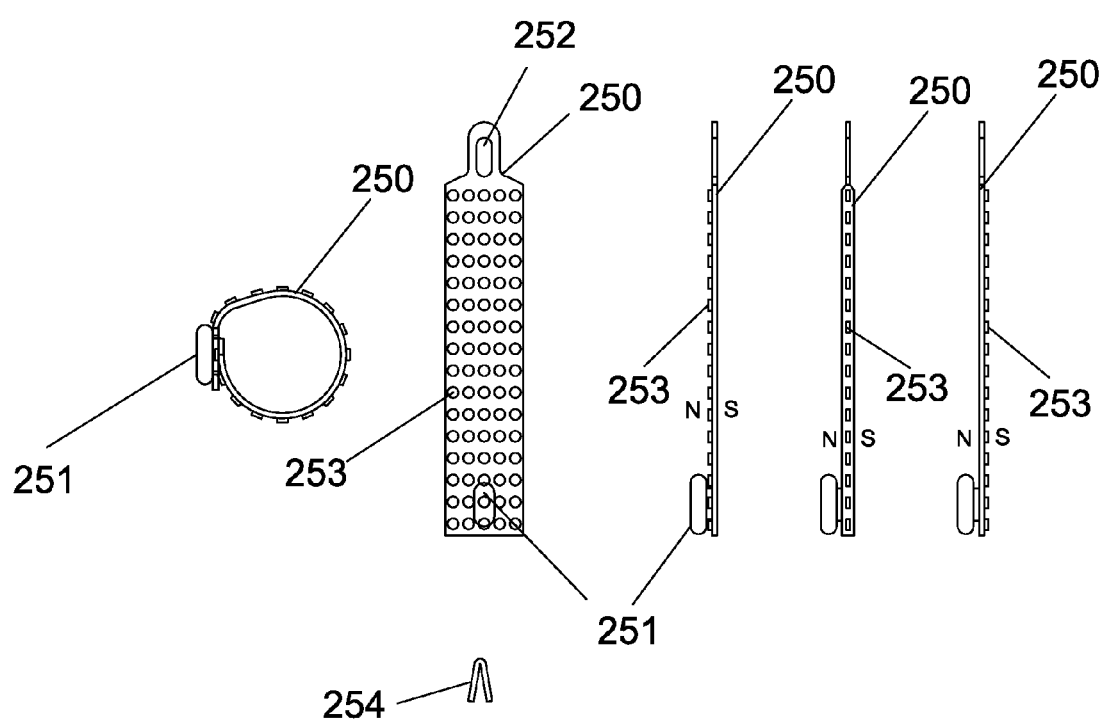

FIG. 3 shows an alternative embodiment of an external band implant 110 in which the magnet 253 shape is changed to be a round disk. The round disk will provide for a band which is easier to longitudinally fold as in 254. This fold will make it easier to insert the band in through a trocar when minimally invasive surgery techniques are used to implant the band.

Figure 4:
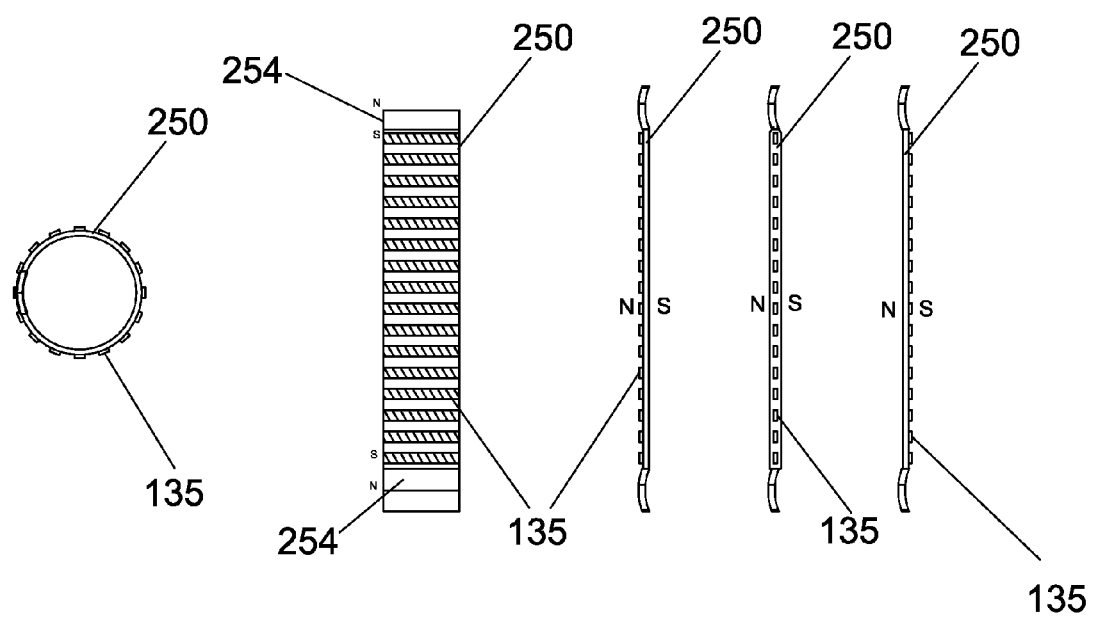

FIG. 4 shows an alternative embodiment of an external band implant 110 with the magnet 135 shaped as in FIG. 2. The band has a magnetic clasp for securing the band 254.

Figure 5:
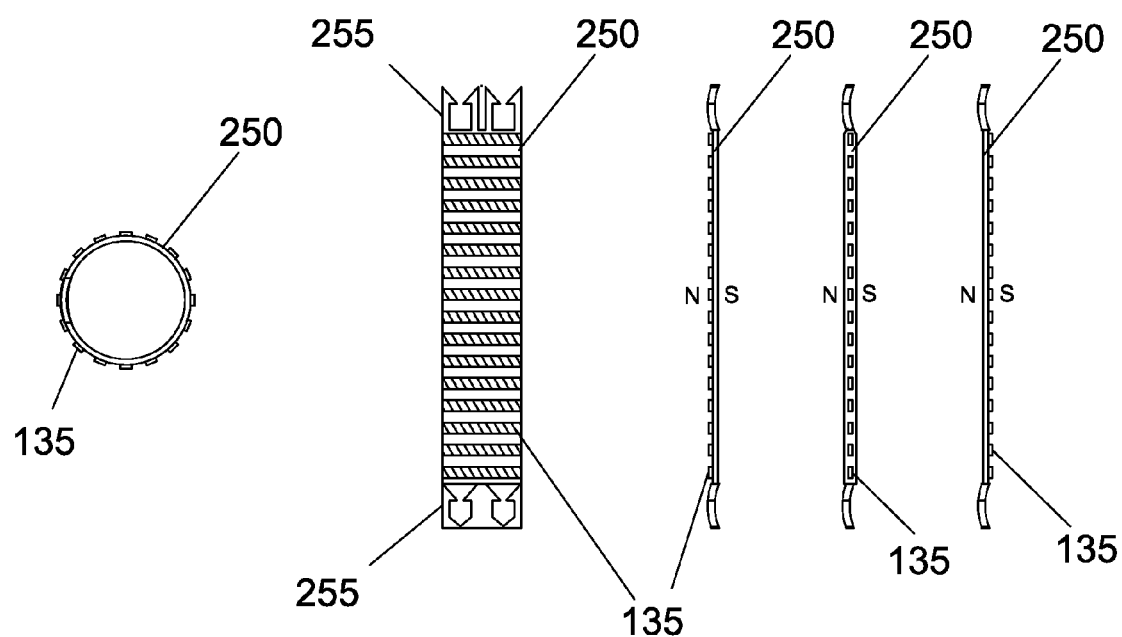

FIG. 5 shows an alternative embodiment of the external band implant 110 with the magnet 135 shaped as in FIG. 2. As shown in FIG. 5, the band has a mechanical clasp for securing the band 255.

Figure 6:
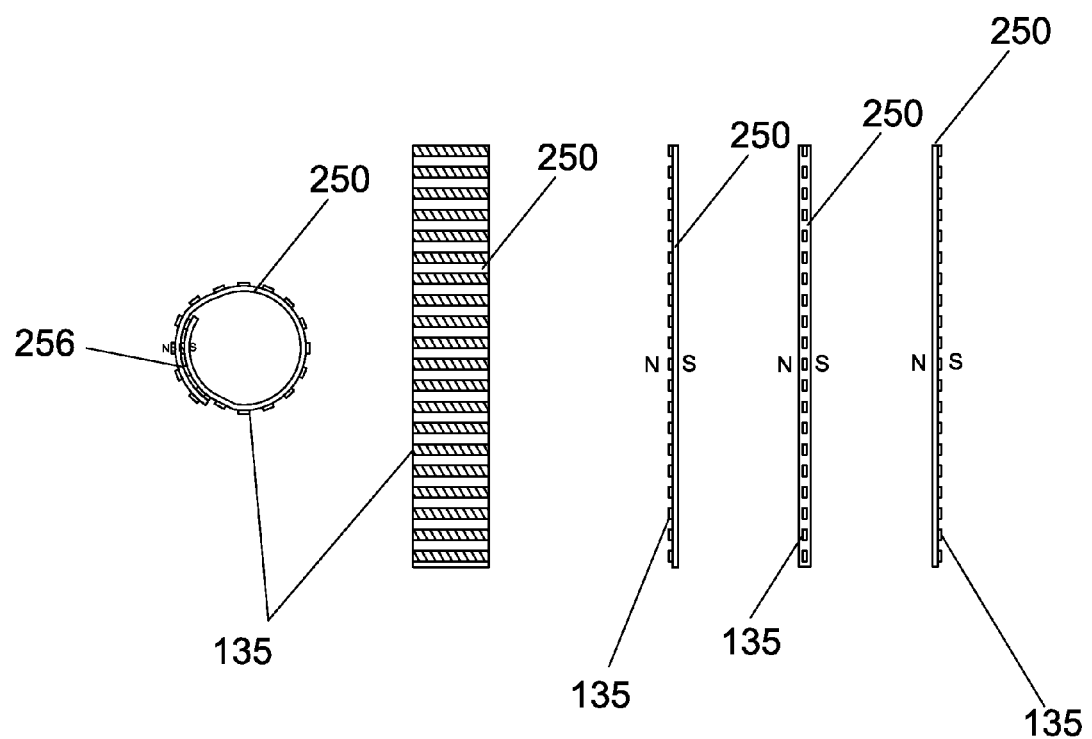

FIG. 6 shows another alternative embodiment of an external band implant 110. The two ends of the band are secured by overlapping the band and the magnets on the inner layer of the band and the outer layer of the band are attracted to each other to hold and secure the band. The band is adjustable in size by changing the length of the overlap 256.

Figure 7:
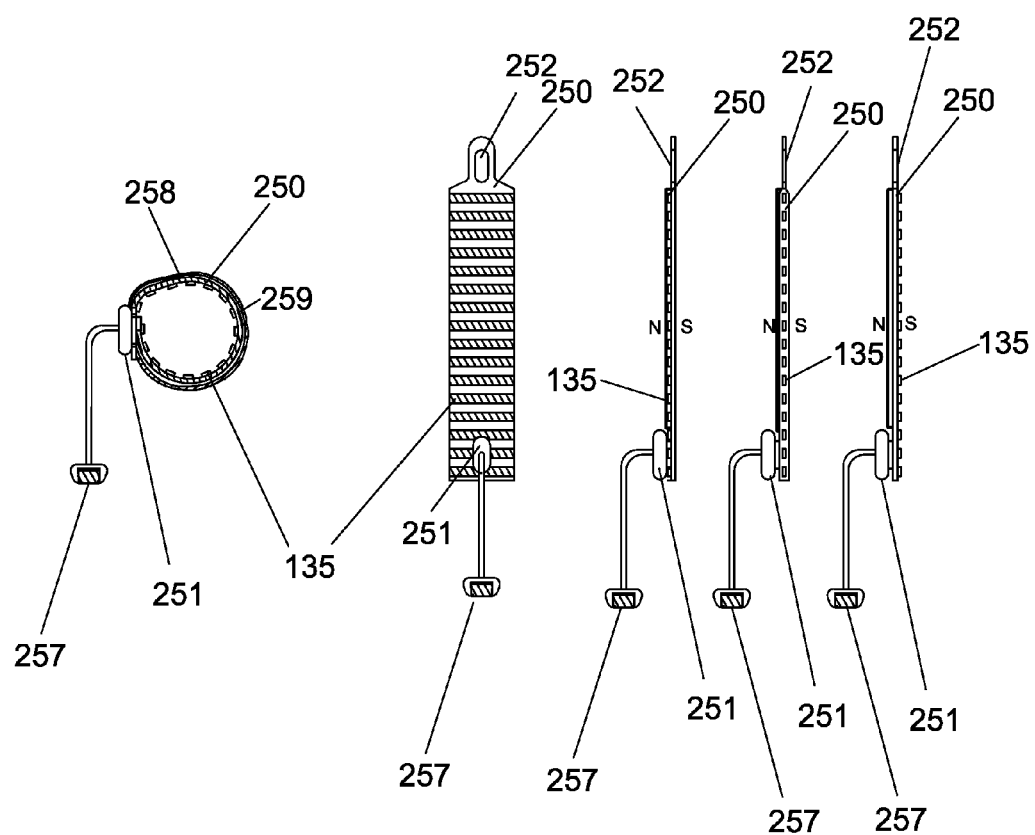

FIG. 7 shows another alternative embodiment of an external band implant 110. The band is secured with the same means as in FIG. 2. The band has been modified to have two layers. The inner layer 250 is similar to FIG. 2., but there is now also an outer band 258. The two bands 250 and 258 form an annular space 259 in between the two bands. This annular space can be filled with air, saline or other suitable material to cause the band to inflate balloon like with the main expansion inward to reduce the inside diameter of the band. The fluid in the device can be adjusted by inserting a needle through the septum 257. Additional fluid may be added or removed through the septum to change the sizing of the band.

Figure 8:
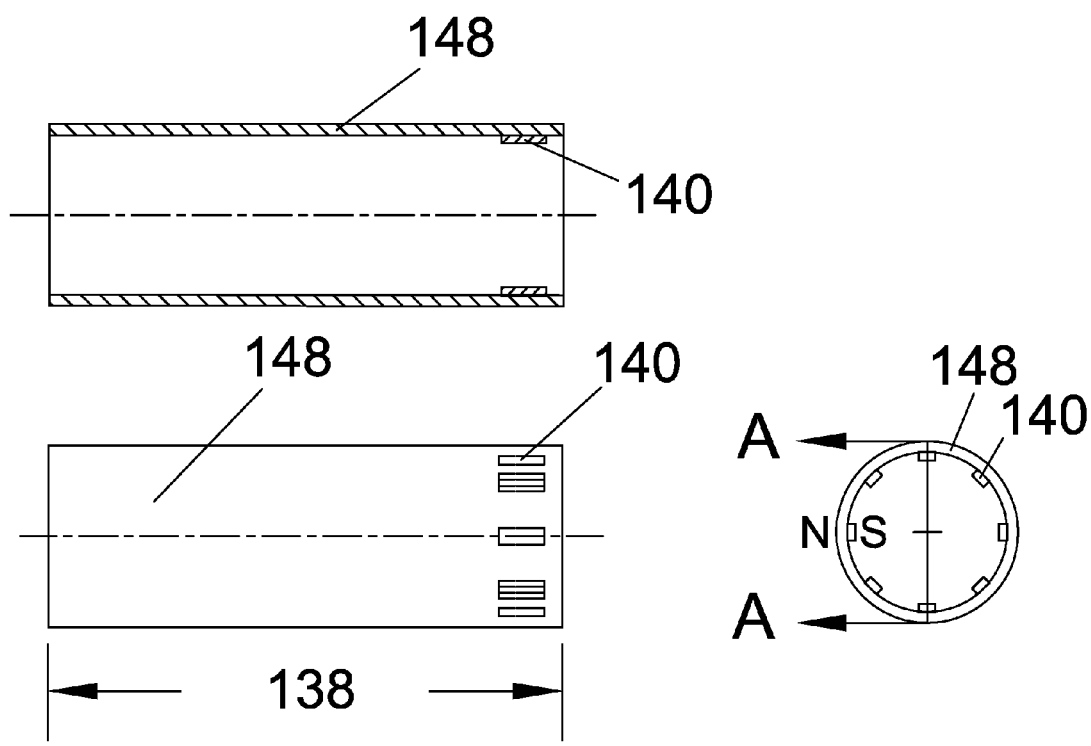
FIG. 8 shows a tubular implant that can be used to bypass the stomach, duodenum or other intestinal lumen.

FIG. 8 shows an internal tubular implant that can be used to bypass the stomach 103, duodenum 112 or other intestinal lumen. The tubular implant is made of a thin wall tube 148 and a series of magnets 140 attached to the inside of the thin wall tube. Section A-A in FIG. 8 shows a sectional view of the tubular implant. The tubular implants, according to various embodiments, are made from one or more of the following materials: silicone, polyether block amides (PEBAX), polyurethanes, silicone polyurethane copolymers, Nylon, polyethylene terphalate (PET), ePTFE, Kevlar, Spectra, Dyneena, polyvinyl chloride (PVC), polyethylene, polyester elastomers or other suitable materials. The thin wall tube length, according to various embodiments, may range from about 1 inch in length up to about 5 feet in length. The thickness of the thin walled tube will typically be in the range of from about 0.0001 inch thick up to about 0.10 inch thick. The diameter of the tubular implant will typically range from about 25 mm to about 35 mm, with a maximum range anticipated of from about 5 mm to about 70 mm in diameter.

Figure 9:
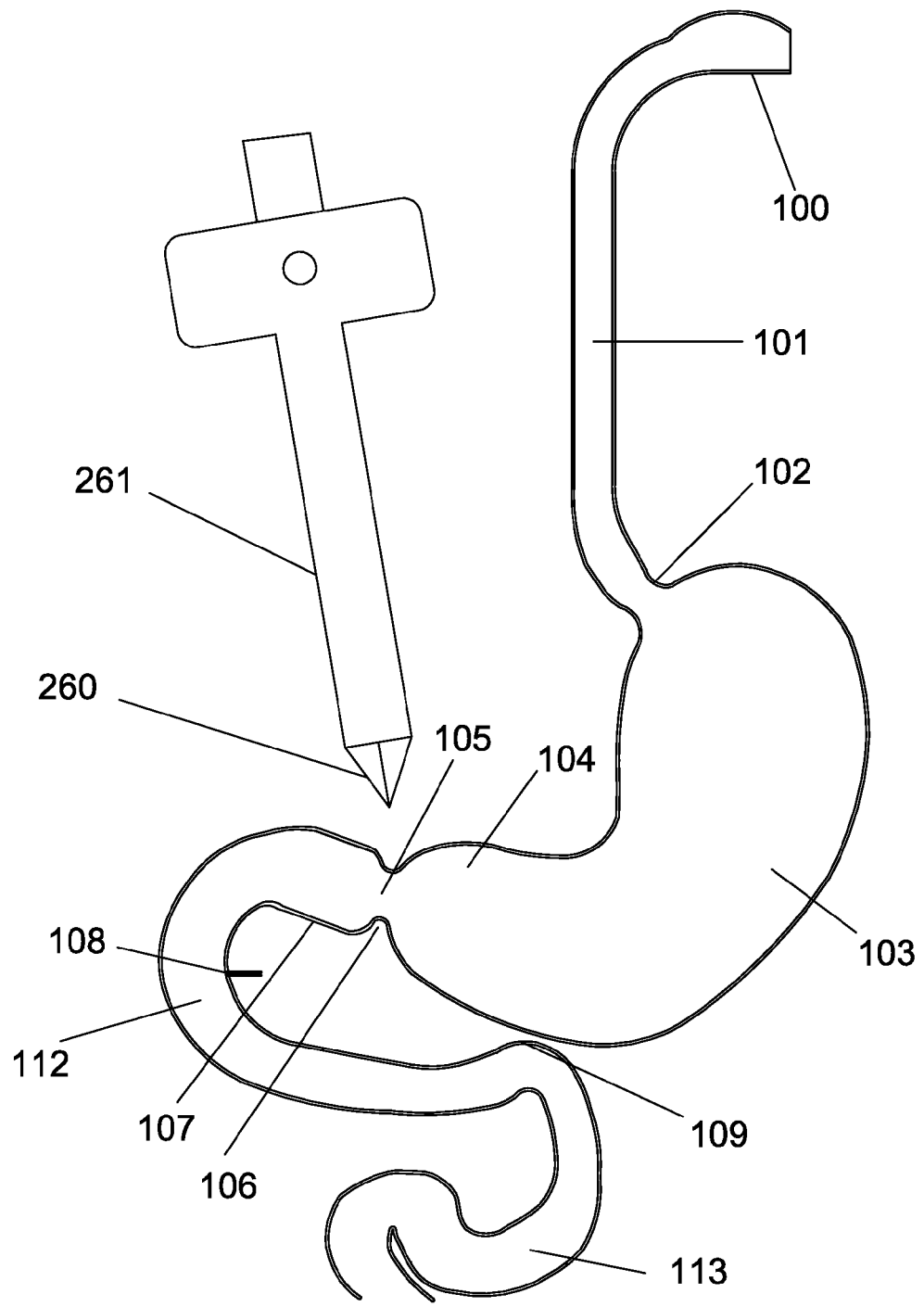
FIG. 9 is a schematic view showing a trocar and cannula operable to access the implant location of the duodenal bulb using laparoscopic techniques.

FIG. 9 shows a cross-sectional view of a portion of the digestive tract in the body with a trocar 260 and cannula 261 inserted to access the implant location of the duodenal bulb using laparoscopic techniques. An alternative access route is to use natural orifice surgery via the esophagus, stomach or vagina.

Figure 10:
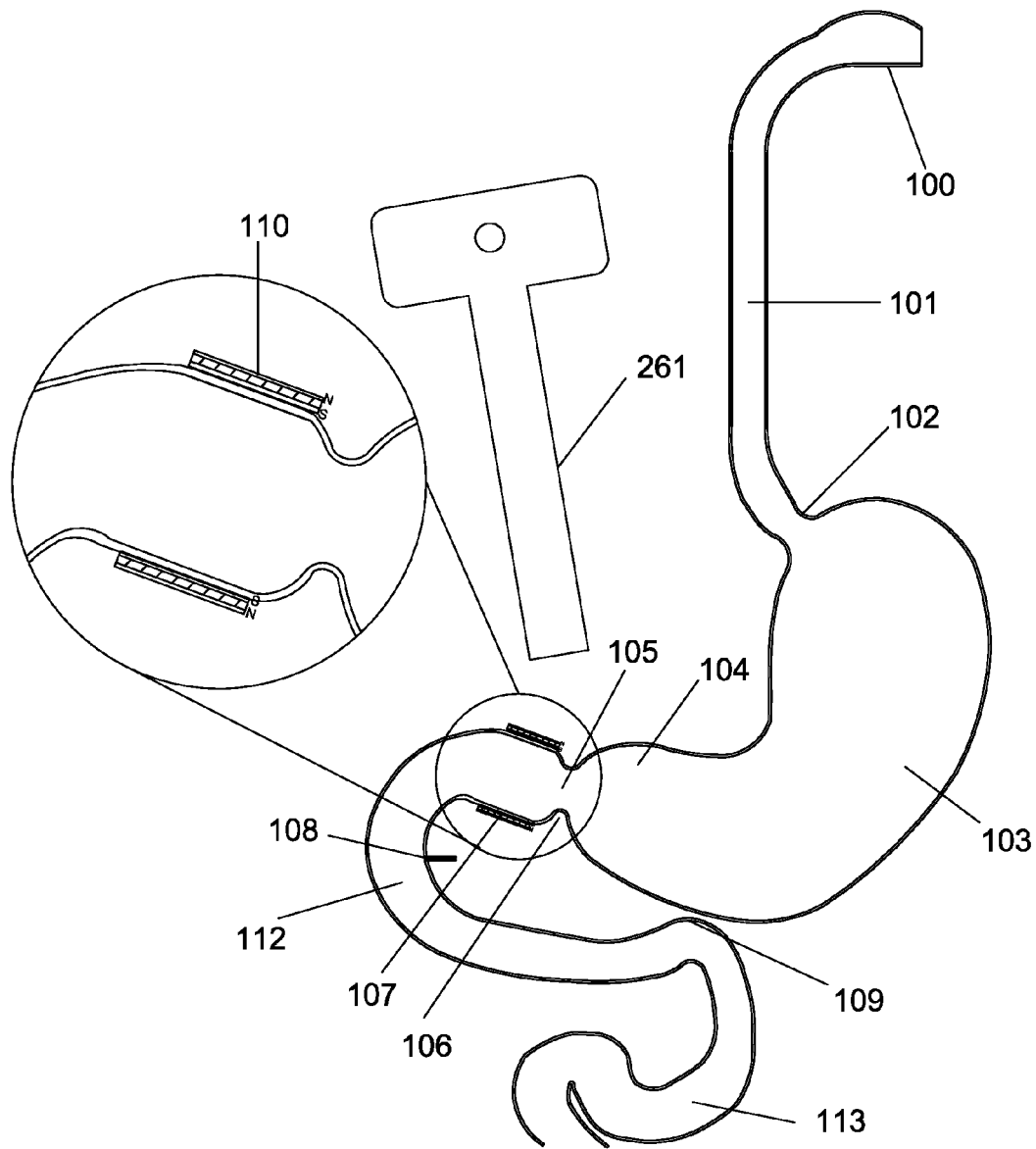
FIG. 10 is a schematic view showing a cannula inserted to access the implant location of the duodenal bulb, and an external band implanted around the duodenal bulb.

FIG. 10 shows a cross-sectional view of a portion of the digestive tract in the body with the trocar removed and cannula 261 inserted to access the implant location of the duodenal bulb using laparoscopic techniques. As shown, the external band 110 has been implanted around the duodenal bulb.

Figure 11:
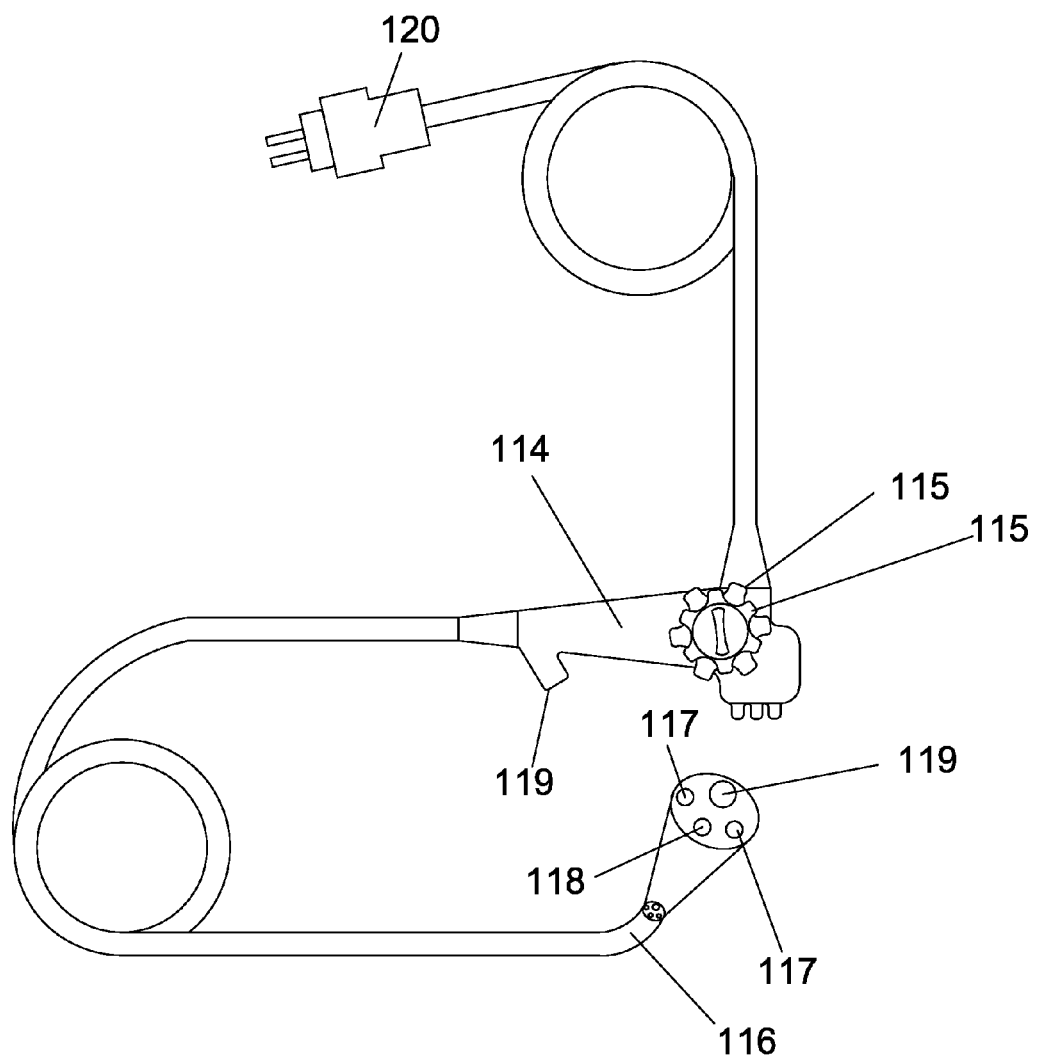
FIG. 11 shows an exemplary endoscope used for diagnostic and therapeutic procedures in the gastrointestinal (GI) tract.

FIG. 11 shows an endoscope 114. Endoscopes 114 are used for diagnostic and therapeutic procedures in the gastrointestinal (GI) tract. The typical endoscope 114 is steerable by turning two rotary dials 115 to cause deflection of the working end 116 of the endoscope. The working end of the endoscope 116 or distal end, typically contains two fiber bundles for lighting 117, a fiber bundle for imaging 118 (viewing) and a working channel 119. The working channel 119 can also be accessed on the proximal end of the endoscope. The light fiber bundles and the image fiber bundles are plugged into a console at the plug in connector 120. The typical endoscope has a working channel in the 2.6 mm to 3.2 mm diameter range. The outside diameter of the endoscopes are typically in the 8 mm to 12 mm diameter range, depending on whether the endoscope is for diagnostic or therapeutic purposes.

Figure 12:
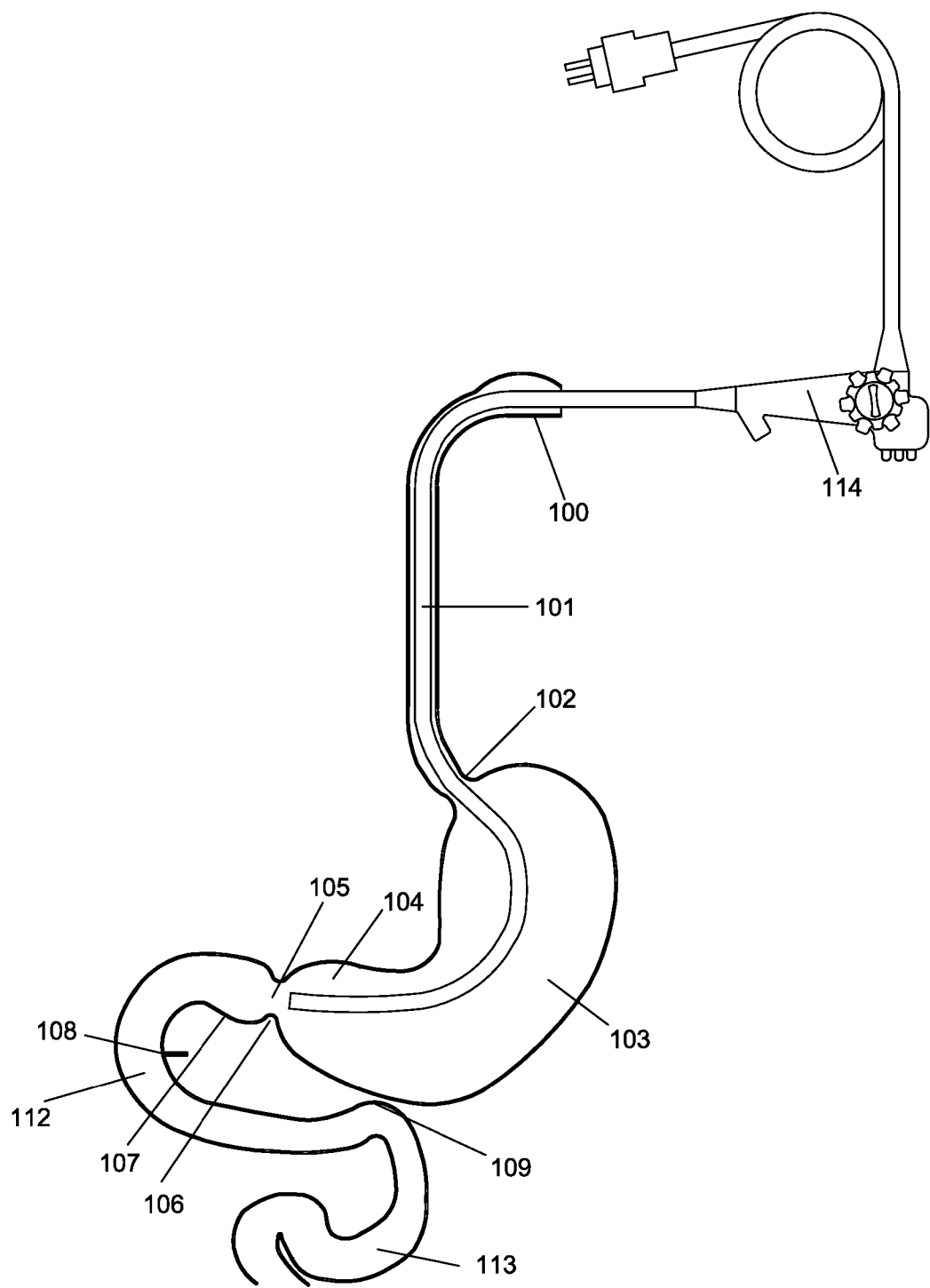
FIG. 12 is a sectional view of a portion of the digestive tract in the body, with an endoscope passing through the esophagus into the stomach, and the end of the scope is positioned to allow viewing of the pylorus.

FIG. 12 is a cross-sectional view of a portion of the digestive tract in a human body. An endoscope 114 has been inserted through: the mouth 100, esophagus 101, stomach 103 and pyloric antrum to allow visualization of the pylorus 106.

Figure 13A:
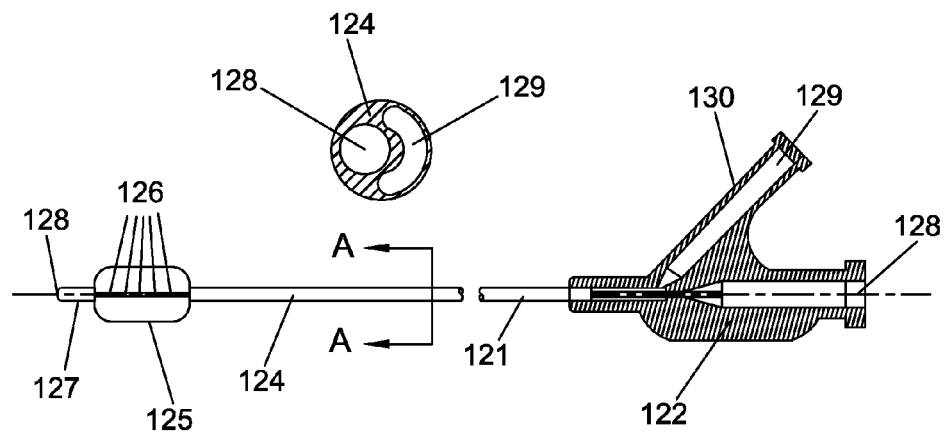
FIG. 13A shows an over-the-wire sizing balloon that can be used to measure the diameter of the pylorus, duodenal bulb, esophagus, pyloric antrum or other lumen in the GI tract.

FIG. 13A shows an over the wire sizing balloon 121 that is used to measure the diameter of the pylorus 106, duodenal bulb 107, esophagus 102, pyloric antrum 104 or other lumen in the GI tract. The sizing balloon is composed of the following elements: proximal hub 122, catheter shaft 124, distal balloon component 125, radiopaque marker bands 126, distal tip 127, guide wire lumen 128, inflation lumen 129. Distal balloon component 125 can be made from silicone, silicone polyurethane copolymers, latex, nylon 12, PET (Polyethylene terphalate) Pebax (polyether block amide), polyurethane, polyethylene, polyester elastomer or other suitable polymer. The distal balloon component 125 can be molded into a cylindrical shape, into a dog bone or a conical shape. The distal balloon component 125 can be made compliant or non-compliant. The distal balloon component 125 can be bonded to the catheter shaft 124 with glue, heat bonding, solvent bonding, laser welding or suitable means. The catheter shaft can be made from silicone, silicone polyurethane copolymers, latex, nylon 12, PET (Polyethylene terphalate) Pebax (polyether block amide), polyurethane, polyethylene, polyester elastomer or other suitable polymer.

Section A-A in FIG. 13A shows a sectional view of the catheter shaft 124. The catheter shaft 124 is shown as a dual lumen extrusion with a guide wire lumen 128 and an inflation lumen 129. The catheter shaft 124 can also be formed from two coaxial single lumen round tubes in place of the dual lumen tubing. The balloon is inflated by attaching a syringe (not shown) to luer fitting side port 130. The sizing balloon accommodates a guidewire through the guidewire lumen from the distal tip 127 through the proximal hub 122. The sizing balloon can be filled with a radiopaque dye to allow visualization and measurement of the size of the anatomy with a fluoroscope. The sizing balloon 121 has two or more radiopaque marker bands 126 located on the catheter shaft to allow visualization of the catheter shaft and balloon position. The marker bands 126 also serve as a fixed known distance reference point that can be measured to provide a means to calibrate and determine the balloon diameter with the use of the fluoroscope. The marker bands can be made from tantalum, gold, platinum, platinum iridium alloys or other suitable material.

Figure 13B:
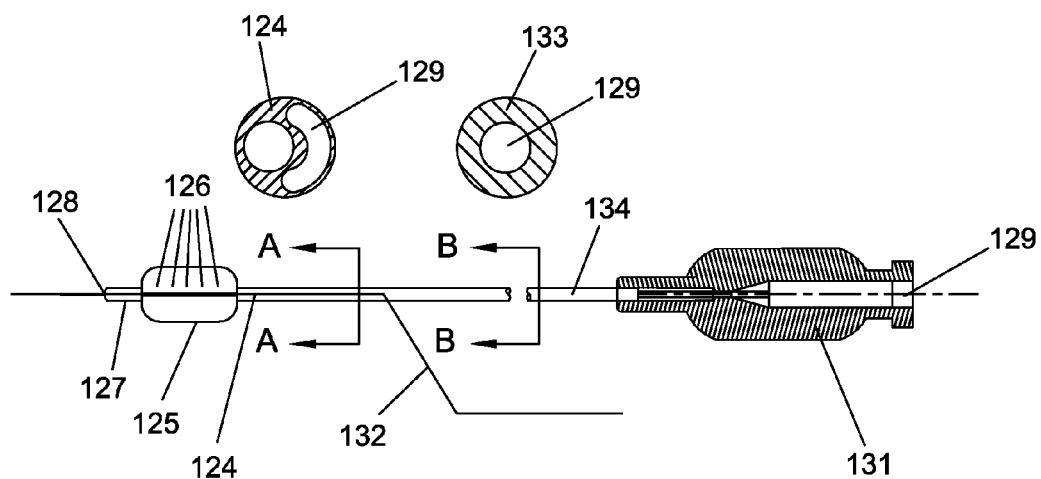
FIG. 13B shows a monorail sizing balloon that can be used to measure the diameter of the pylorus, duodenal bulb, esophagus, pyloric antrum or other lumen in the GI tract.

FIG. 13B shows a rapid exchange sizing balloon 134 that is used to measure the diameter of the pylorus 106, duodenal bulb 107, esophagus 102, pyloric antrum 104 or other lumen in the GI tract. The sizing balloon is composed of the following elements: proximal luer 131, catheter shaft 124, distal balloon component 125, radiopaque marker bands 126, distal tip 127, guide wire lumen 128, inflation lumen 129. The materials of construction will be similar to that of FIG. 4A. The guidewire lumen 128 does not travel the full length of the catheter, it starts at the distal tip 127 and exits out the side of the catheter at a distance shorter than the overall catheter length. Guidewire 132 is inserted into the balloon catheter to illustrate the guidewire path through the sizing balloon. The sizing balloon catheter shaft changes the section along its length from a single lumen at section B-B 133 to a dual lumen at section A-A at 124.

Figure 14:
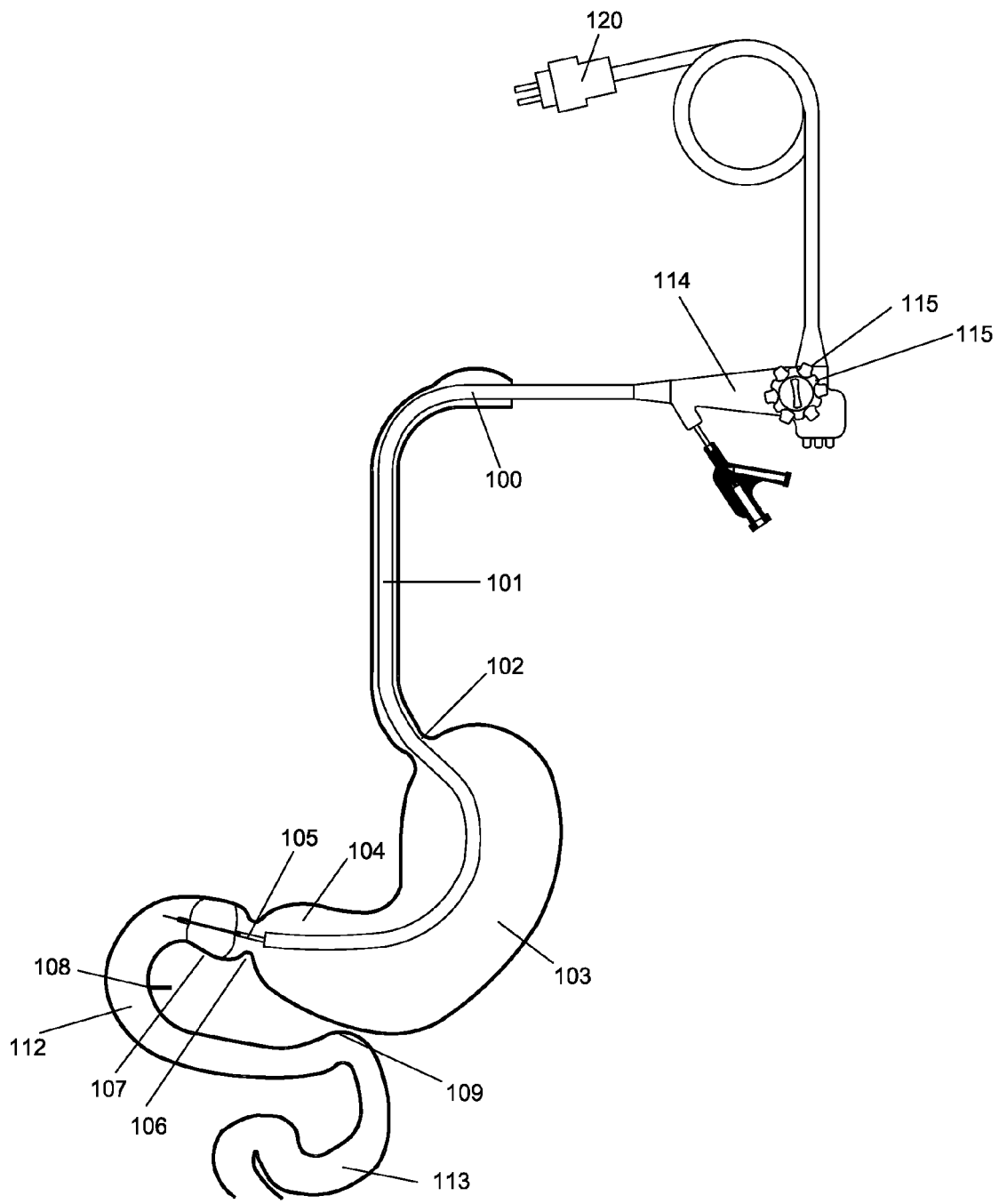
FIG. 14 is a sectional view of a portion of the digestive tract in the body, with an endoscope inserted into the GI tract up to the pylorus and a sizing balloon inserted through the working channel and into the area of the duodenal bulb. The balloon is inflated to measure the diameter of the duodenal bulb.

FIG. 14 shows an endoscope 114 inserted into the GI tract up to the pylorus 106. A sizing balloon 121 is inserted through the working channel 119 of the endoscope and into the area of the duodenal bulb 107. The sizing balloon 121 is inflated with a contrast agent. The diameter of the duodenal bulb 107 is measured with a fluoroscope.

Figure 15:
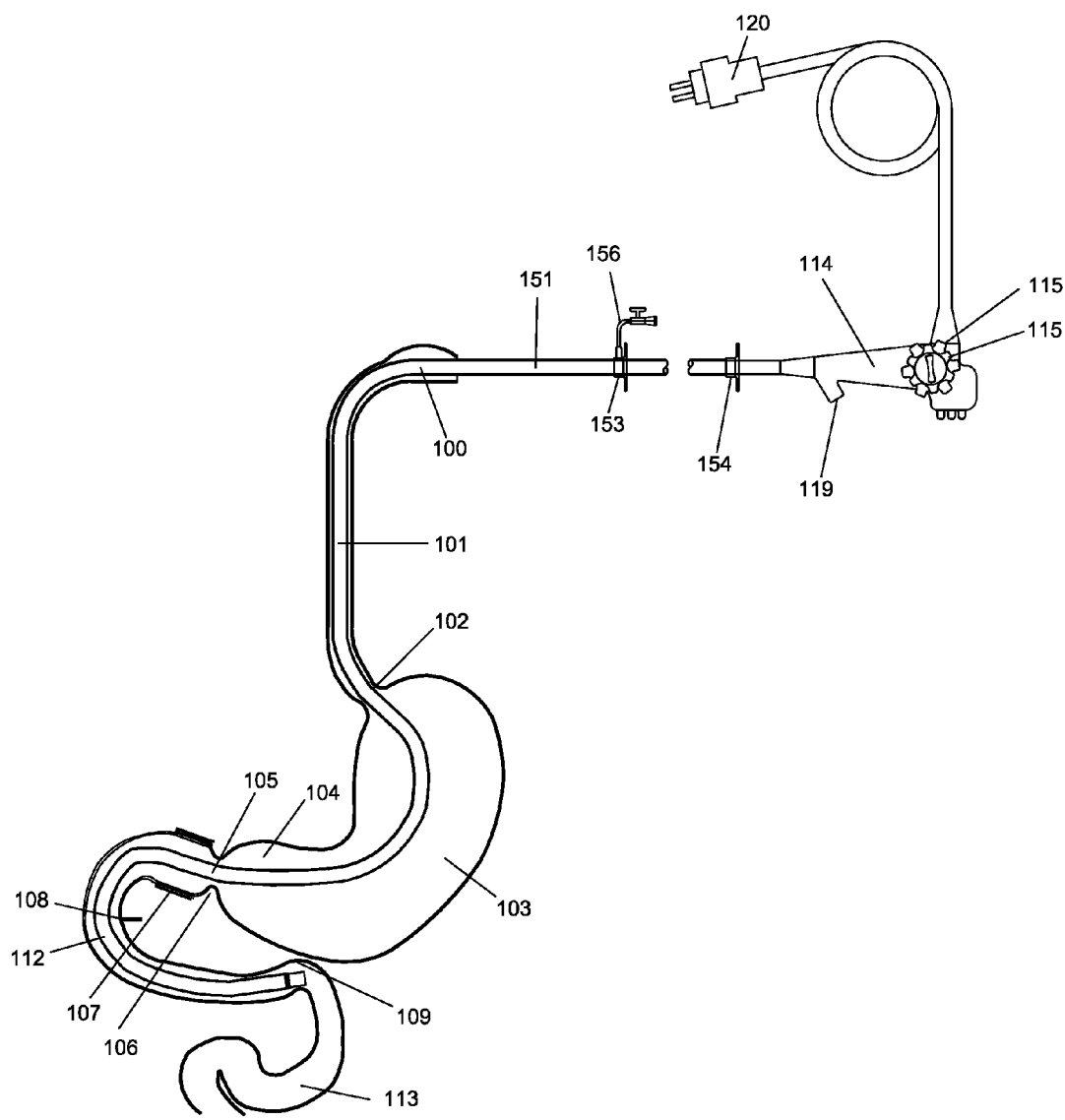
FIG. 15 shows the endoscope and delivery catheter advanced through the external anchoring device into the duodenum to the ligament of Treitz.

FIG. 15 shows a sectional view of a portion of the digestive tract in the body. An internal tubular implant is loaded onto the delivery catheter. The delivery catheter, according to various embodiments, is advanced into the duodenum 112 until the distal end of the delivery catheter is at the ligament of Treitz 109. While in many embodiments, the end of the delivery catheter is positioned at the ligament of Treitz 109, according to other embodiments, the end of the delivery catheter is located proximal or distal to the ligament of Treitz 109. For example, the distal end of the delivery catheter may be located in the jejunum 113. The internal tubular implant is deployed from the delivery catheter by pulling handle 153 towards 154.

Figure 16:
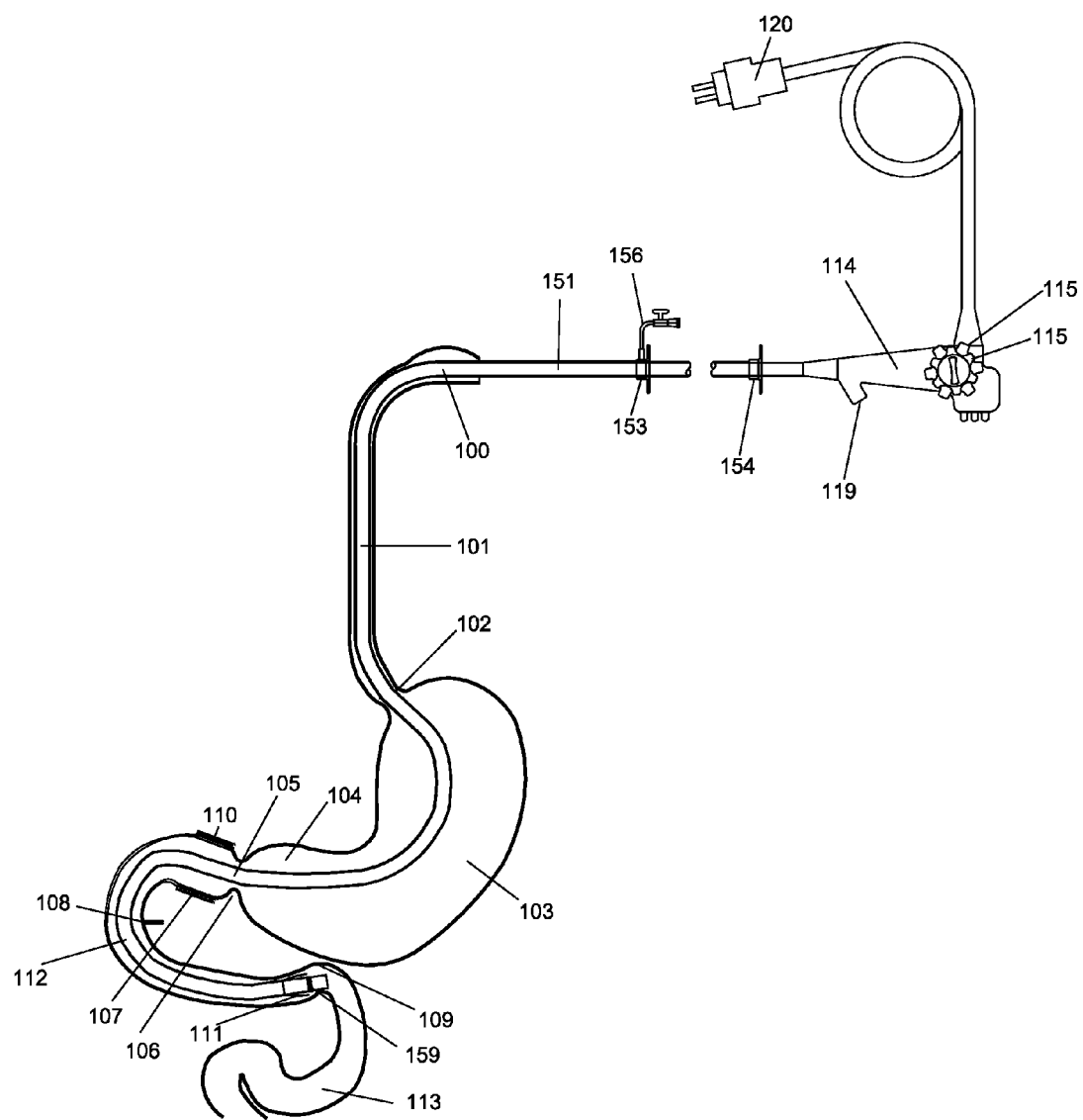
FIG. 16 shows the endoscope and delivery catheter advanced through the external anchoring device into the duodenum to the ligament of Treitz. The outer sheath of the delivery catheter is retracted to partially expose the tubular implant.

Next, as shown in FIG. 16, the outer sheath 151 on the delivery catheter is retracted a couple of inches to expose the tubular implant 111.

Figure 17:
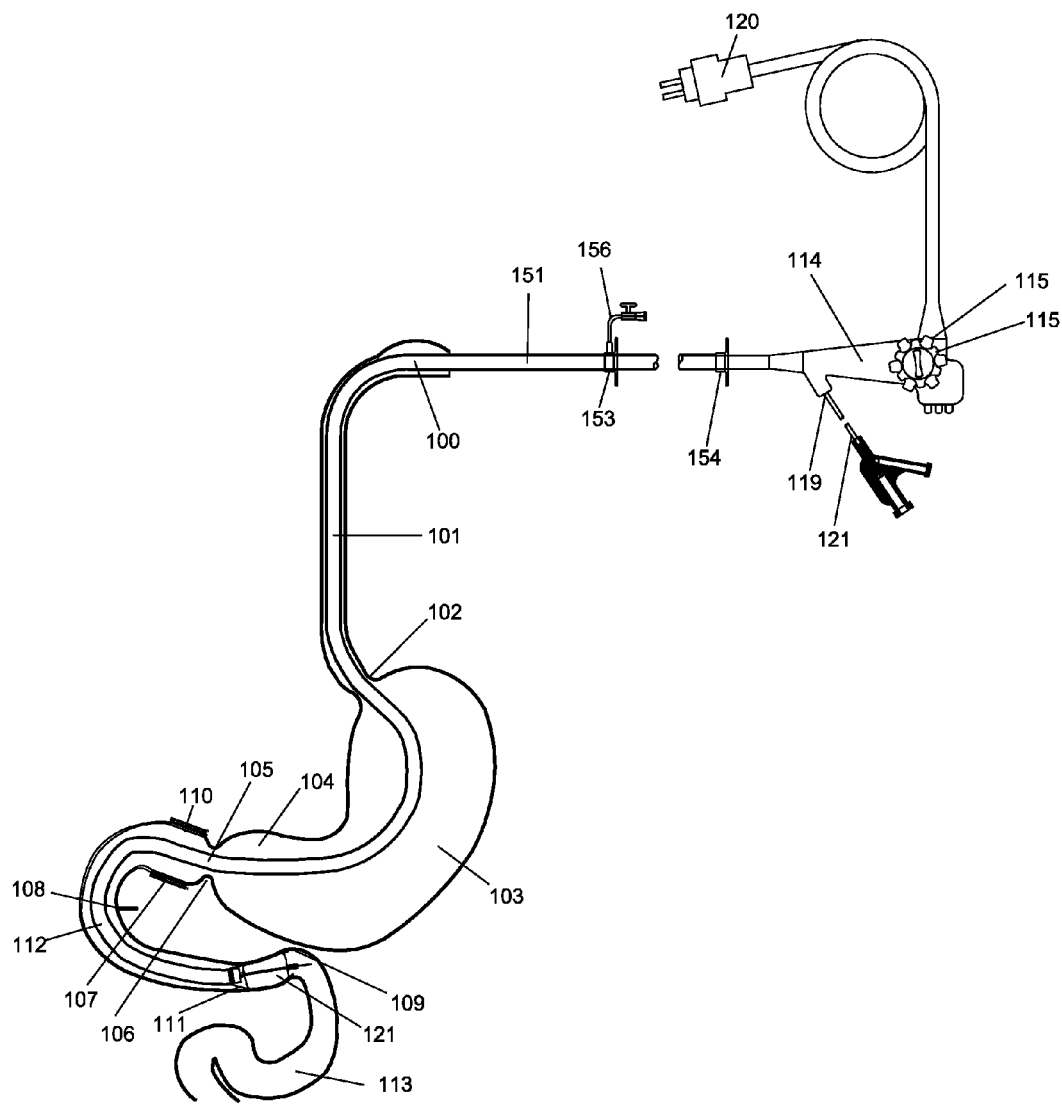
FIG. 17 shows the endoscope and delivery catheter advanced through the external anchoring device into the duodenum to the ligament of Treitz. The outer sheath of the delivery catheter is retracted to partially expose the tubular implant. A balloon catheter is inserted through the working channel of the endoscope to the area of the partially exposed tubular implant. The balloon is inflated to temporarily secure the tubular implant to the duodenum.

Next, as shown in FIG. 17, a sizing balloon 121 is inserted through the working channel 119 on endoscope 114. The sizing balloon 121 is advanced about one inch beyond the distal end of the endoscope 114 but still inside of the tubular implant 111. The sizing balloon 121 is then inflated with saline or contrast agent. The inflated sizing balloon 121 will hold the tubular implant 111 in place in the duodenum 112 or jejunum 113 (e.g., near the ligament of Treitz 109).

Figure 18:
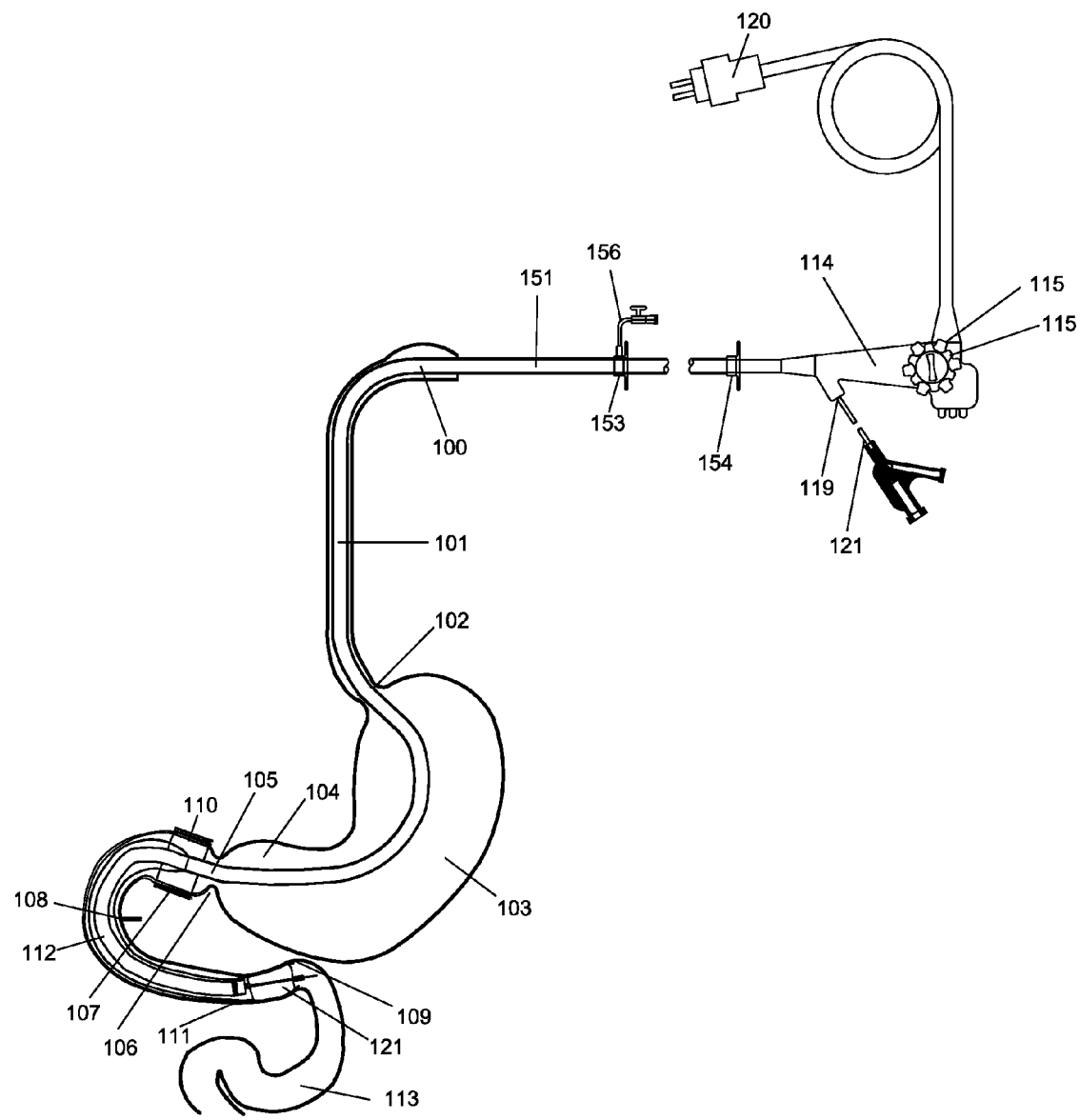
FIG. 18 shows the system of FIG. 17, where the outer sheath is retracted further to unsheath the tubular implant up to the duodenal bulb.

Then, as shown in FIG. 18, the outer sheath 151 is retracted further to expose all but a couple of centimeters of the tubular implant 111. The outer sheath 151 end is now near the pylorus 106.

Figure 19:
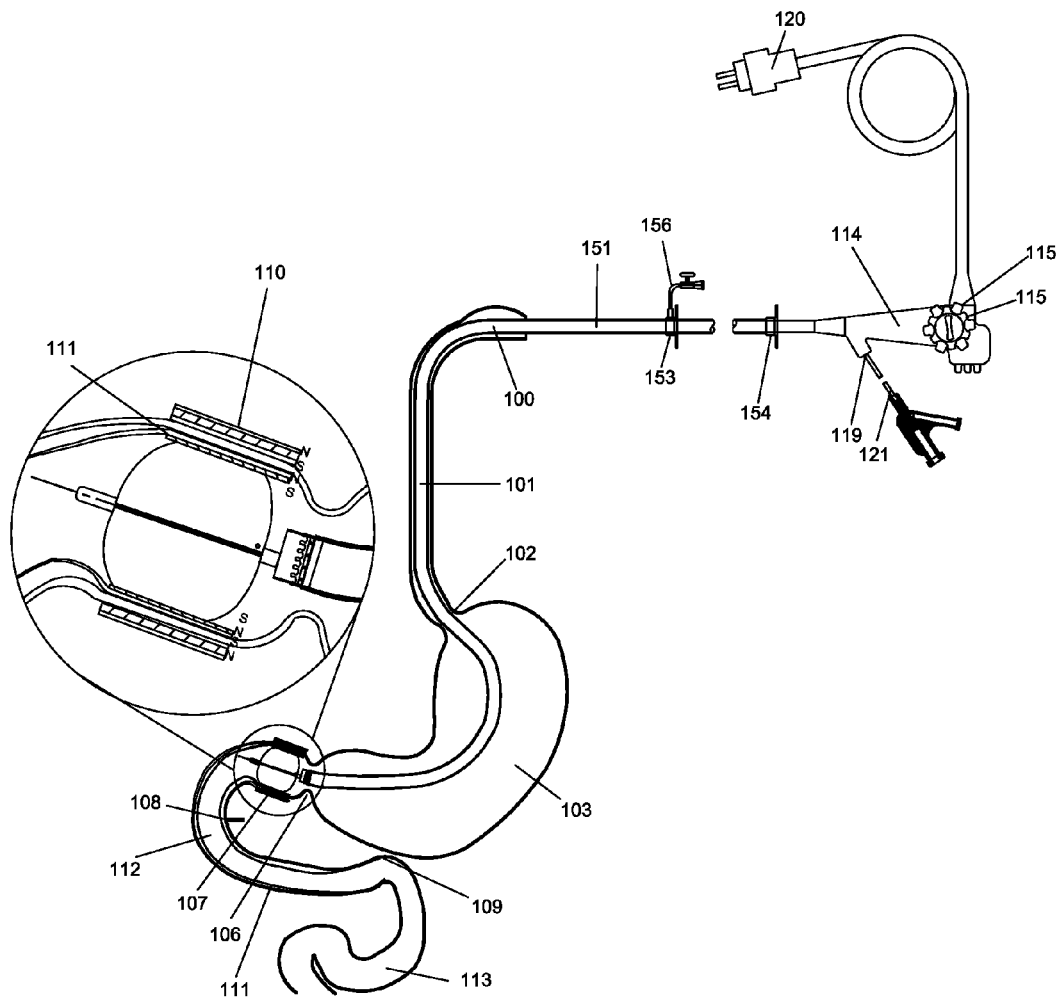
FIG. 19 shows the system of FIG. 18, where the endoscope has been withdrawn to the duodenal bulb. The balloon on the balloon catheter is then deflated and the balloon catheter is withdrawn to the duodenal bulb. The balloon is then re-inflated to open up and secure the proximal end of the tubular implant to the inside diameter of the docking element.

Then, as shown in FIG. 19, the distal end of the endoscope 114 has been pulled back to the pyloric orifice 105 and the sizing balloon 121 has been deflated and repositioned and reinflated to seat the proximal end of the internal tubular implant 111 to be in contact with the outer band 110. The magnets 140 on the tubular sleeve are now in contact with the magnets 140 on the docking element. The magnetic attraction between the magnets 140 secures the tubular implant 111 to the docking element 110.

Figure 20:
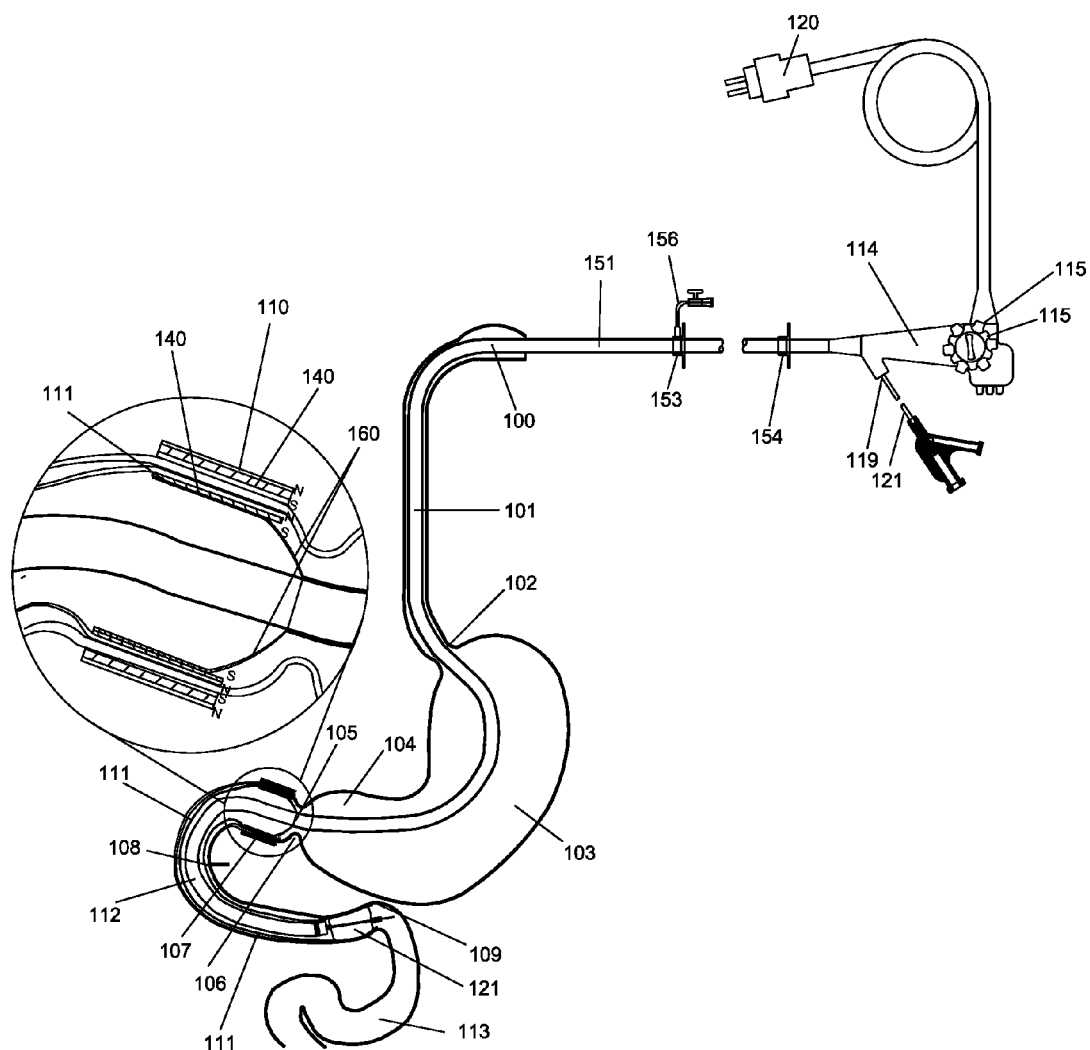
FIG. 20 shows an alternative device and method for deploying the proximal end of the tubular element.

FIG. 20 is an alternative embodiment showing a means to seat the proximal end of the internal tubular implant 111 to the outer band 110. A nitinol conical/tubular shaped forceps 160 are attached to the inner catheter near the proximal end of where the tubal implant is loaded on the delivery catheter. The nitinol forceps 160 have an elastic memory in the open state. When the outer sheath 151 is fully retracted, the conical forceps open and, in turn, open the proximal end of the tubular implant 111 and seats the magnets 140 on the tubular implant 111 to the magnets 140 on the outer band 111.

Figure 21:
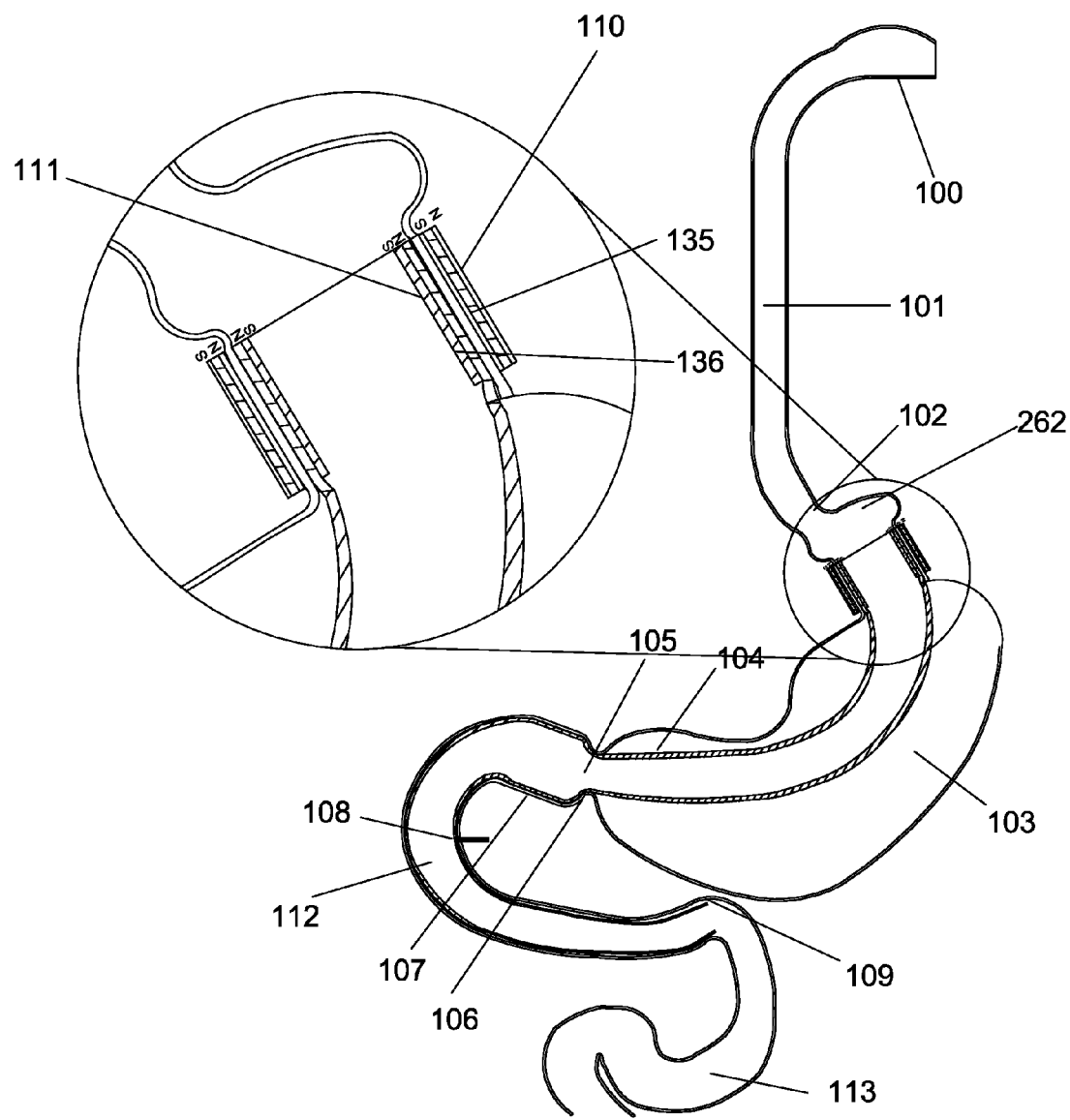
FIG. 21 is a sectional view of a portion of the digestive tract in the body. An external anchoring device is implanted around the stomach a couple of inches below the gastro-esophageal junction. The external anchoring device can serve as a restrictive means and can form a pouch-like restrictive segment at the top of the stomach. An internal tubular implant is implanted from the external anchoring device at the stomach to the ligament of Treitz.

FIG. 21 shows a sectional view of a portion of the digestive tract in a human body. As shown, magnets 135 on the external band 110 and magnets 136 on the internal tubular implant 111 are magnetically attracted to each other and secure the internal tubular implant to the 111 to the external band implant 110. As shown, the external band 110 is secured to the tubular implant 111 at or near the gastro-esophageal junction. The external band 110 around the stomach creates a small pouch like area at the top of the stomach and causes a restrictive component to food flow into the digestive system. An external band 110 is implanted around the upper portion of the stomach and an internal tubular implant 111 is attached to the external band 110 and extended into the duodenum 112 or jejunum 113 (e.g., at or near the ligament of Treitz 109).

Figure 22:
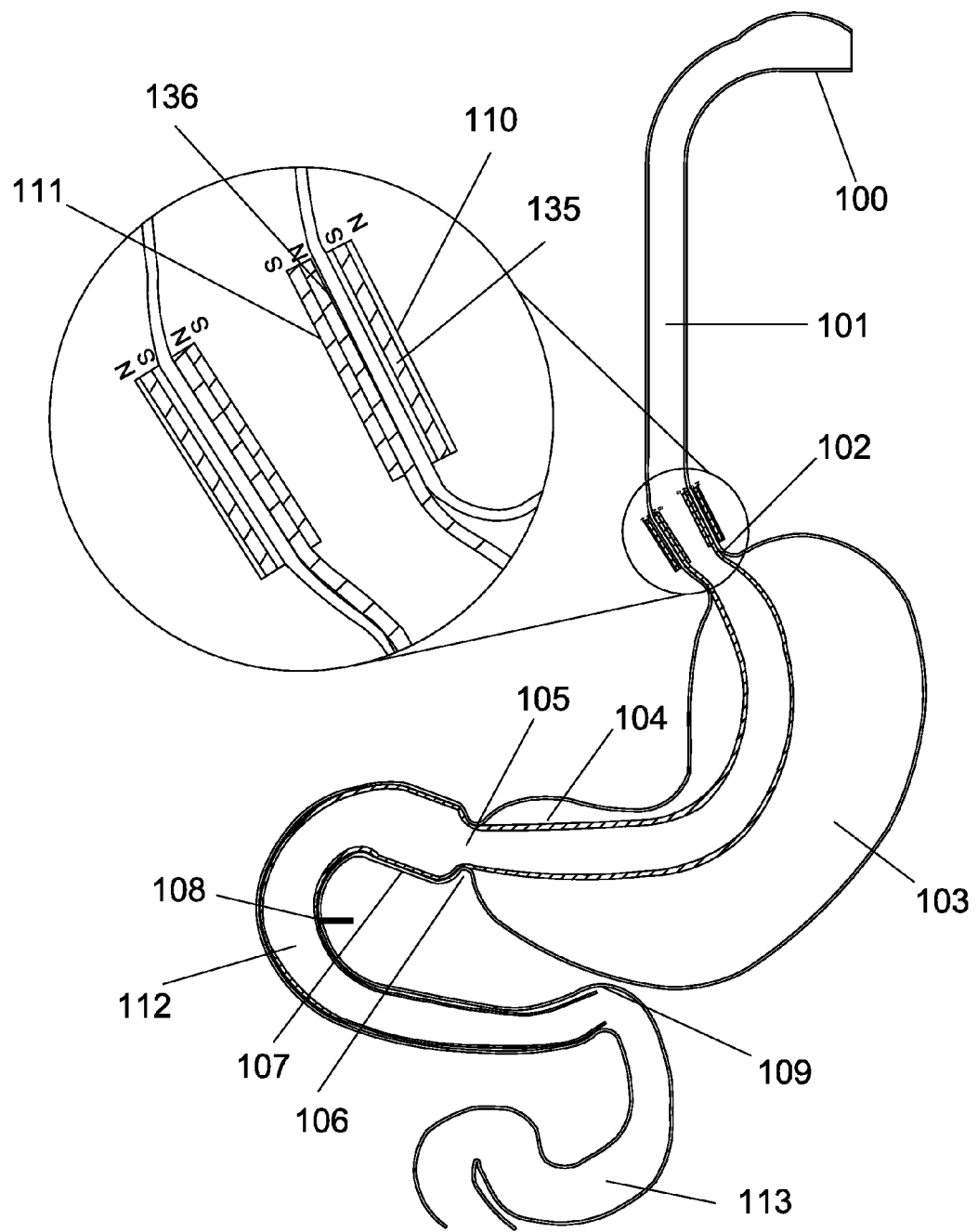
FIG. 22 is a sectional view of a portion of the digestive tract in the body. An external anchoring device is implanted around the esophagus at gastro-esophageal junction. An internal tubular implant is implanted from the external anchoring device at the gastro-esophageal junction to the ligament of Treitz.

FIG. 22 shows a sectional view of a portion of the digestive tract in a human body. As shown, magnets 135 on the external band 110 and magnets 136 on the internal tubular implant 111 are magnetically attracted to each other and secure the internal tubular implant to the 111 to the external band implant 110. As shown, the external band 110 is secured to the tubular implant 111 at or near the gastro-esophageal junction. An external band 110 is implanted around the esophagus and an internal tubular implant 111 is attached to the external band 110 and extended into the duodenum 112 or the jejunum 113 (e.g., at or near the ligament of Treitz 109).

Figure 23:
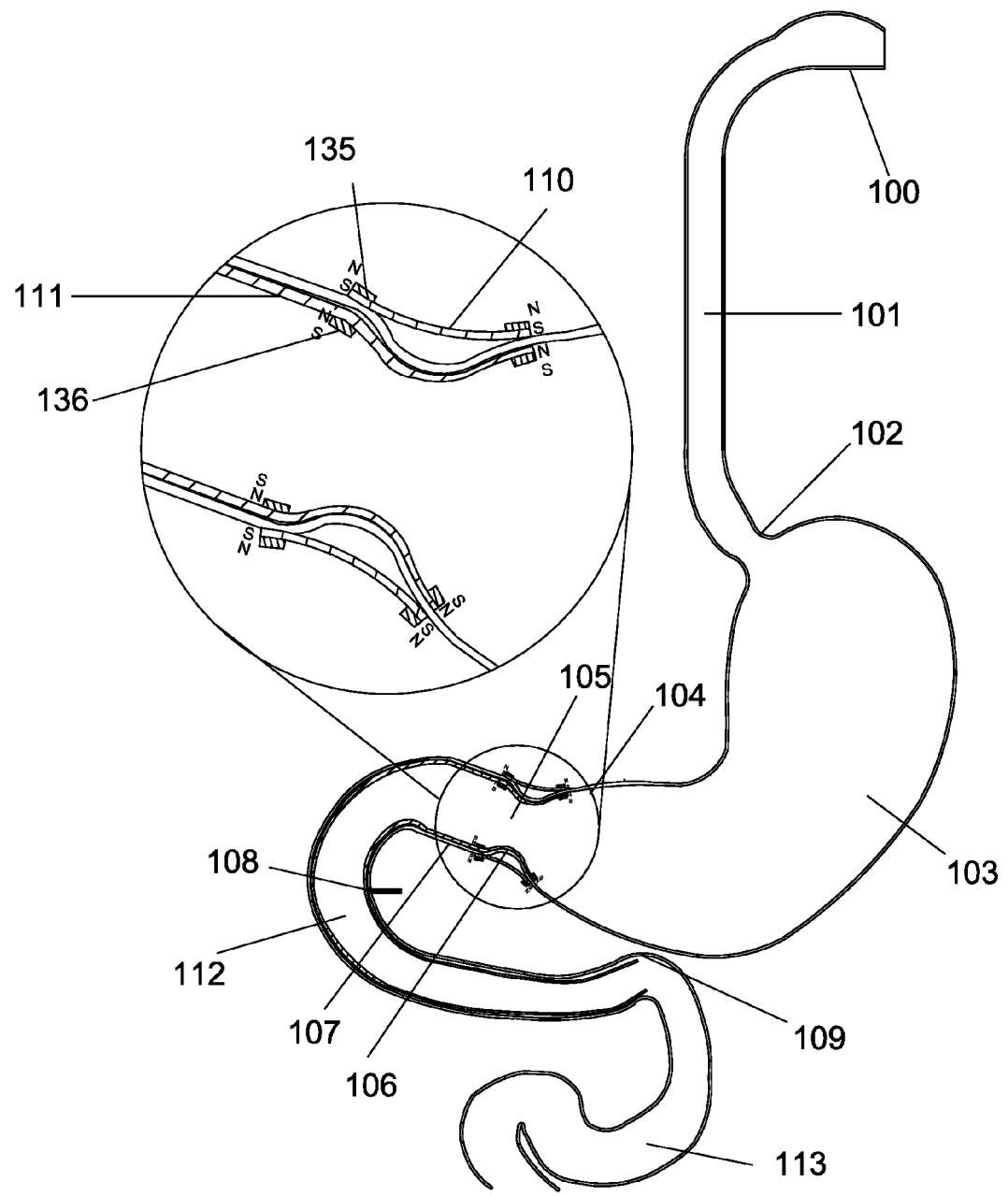
FIG. 23 is a sectional view of a portion of the digestive tract in the body. An external anchoring device is implanted around the pylorus. An internal tubular implant is implanted from the external anchoring device at the pylorus to the ligament of Treitz.

FIG. 23 shows a sectional view of a portion of the digestive tract in a human body. As shown, magnets 135 on the external band 110 and magnets 136 on the internal tubular implant 111 are magnetically attracted to each other and secure the internal tubular implant 111 to the external band implant 110. As shown, the external band 110 is secured to the tubular implant 111 at or near the gastrointestinal junction (e.g., across the pylorus) and the internal tubular implant 111 extends into the duodenum 112 or the jejunum 113 (e.g., to the ligament of Treitz 109).

Figure 24:
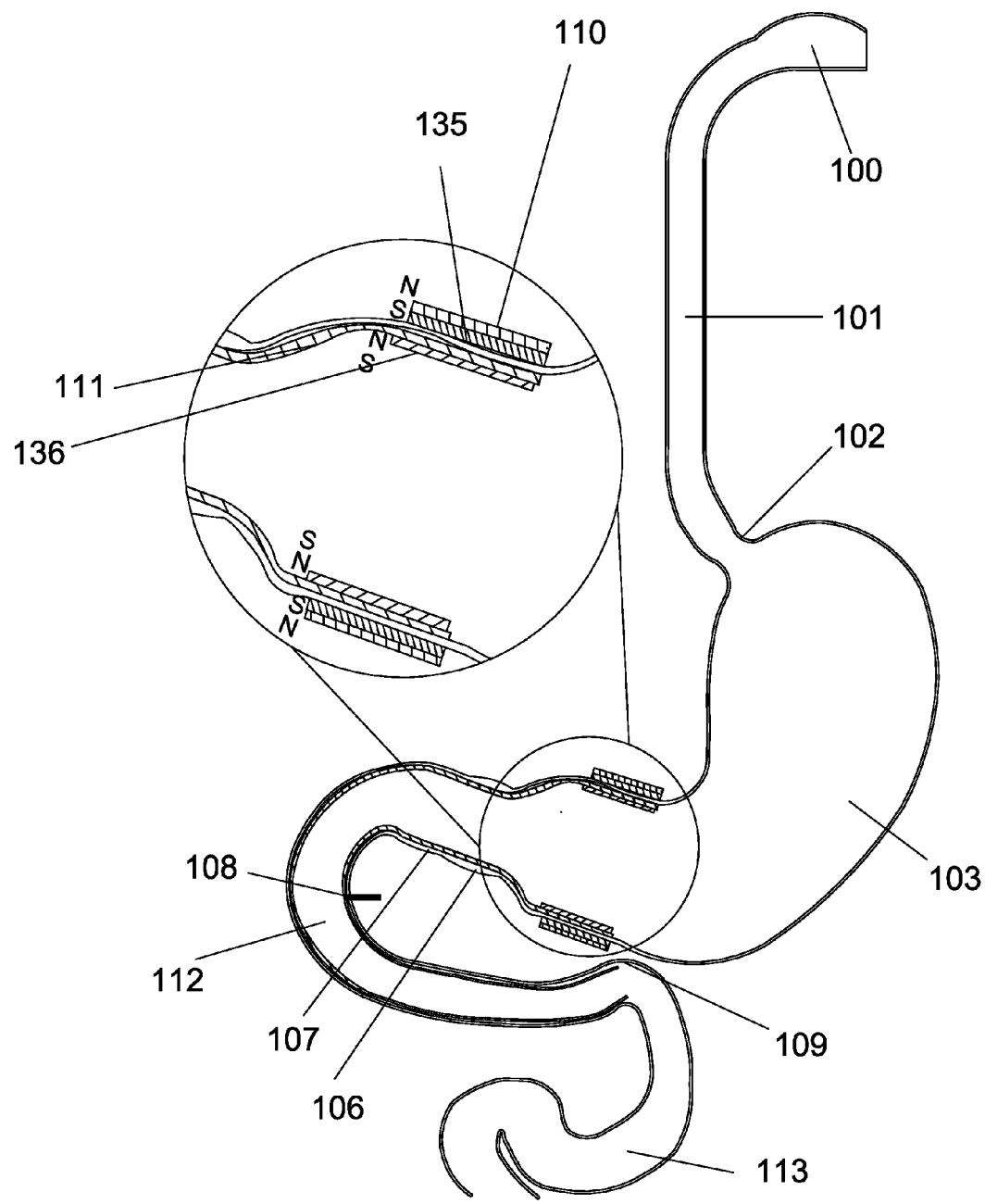
FIG. 24 is a sectional view of a portion of the digestive tract in the body. An external anchoring device is implanted around the stomach antrum. An internal tubular implant is implanted from the external anchoring device at the stomach antrum to the ligament of Treitz.

FIG. 24 shows a sectional view of a portion of the digestive tract in a human body. As shown, the external band 110 is implanted around the stomach antrum and an internal tubular implant 111 is attached to the external band 110 and is extended into the duodenum 112 or the jejunum 113 (e.g., to the ligament of Treitz 109). As shown, magnets 135 on the external band 110 and magnets 136 on the internal tubular implant 111 are magnetically attracted to each other and secure the internal tubular implant 111 to the external band implant 110.

Figure 25:
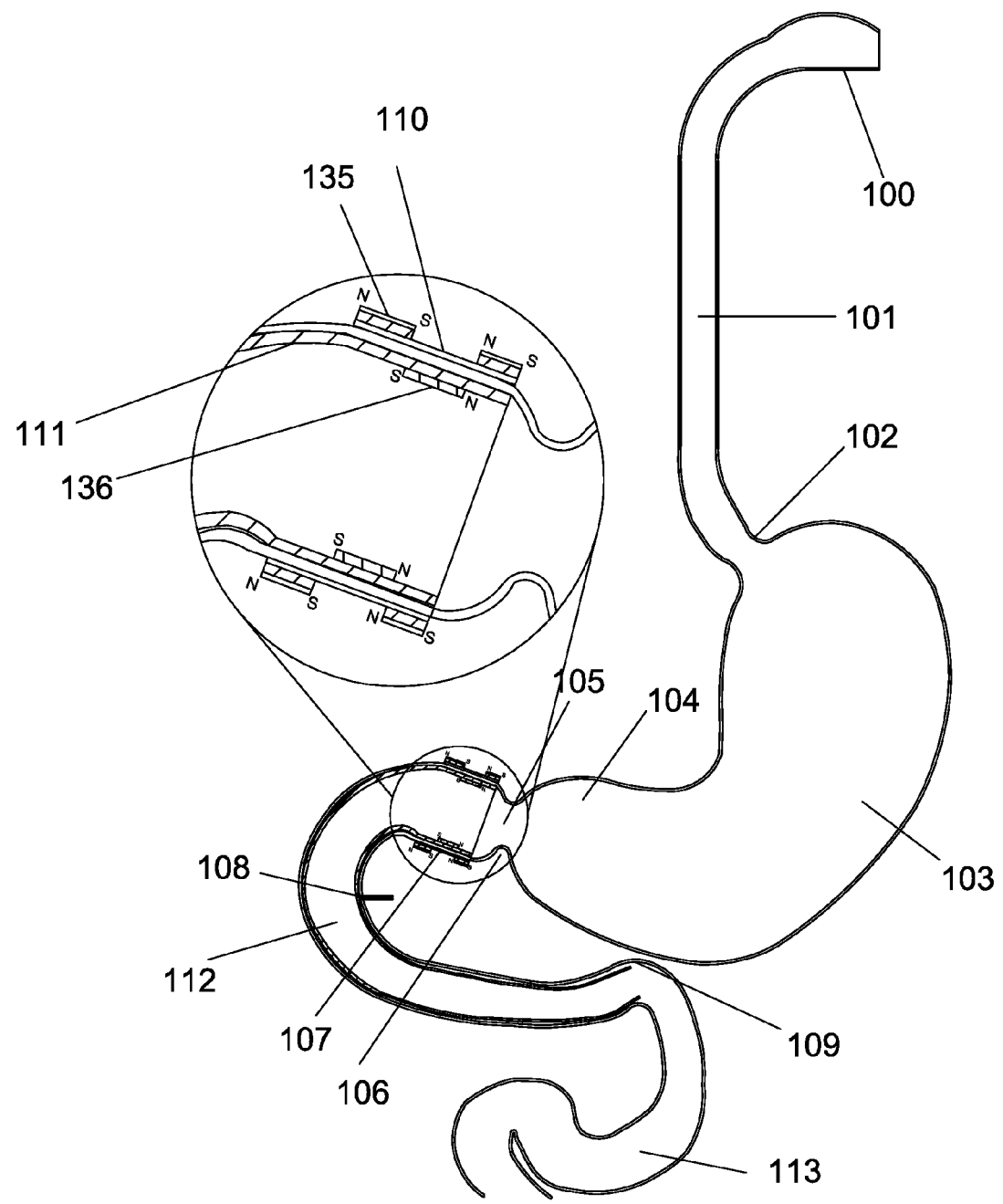
FIG. 25 is a sectional view of a portion of the digestive tract in the body. An external anchoring device is implanted around the duodenal bulb. An internal tubular implant is implanted from the duodenal bulb to the ligament of Treitz.

FIG. 25 shows a sectional view of a portion of the digestive tract in a human body. An external band 110 is implanted around the duodenal bulb 107 and an internal tubular implant 111 is attached to the external band 110 and extended into the duodenum 112 or the jejunum 113 (e.g., to the ligament of Treitz 109). Magnets 135 on the external band 110 and magnets 136 on the internal tubular implant 111 are magnetically repelled from each other and secure the internal tubular implant 111 to the external band implant 110.

Figure 26:
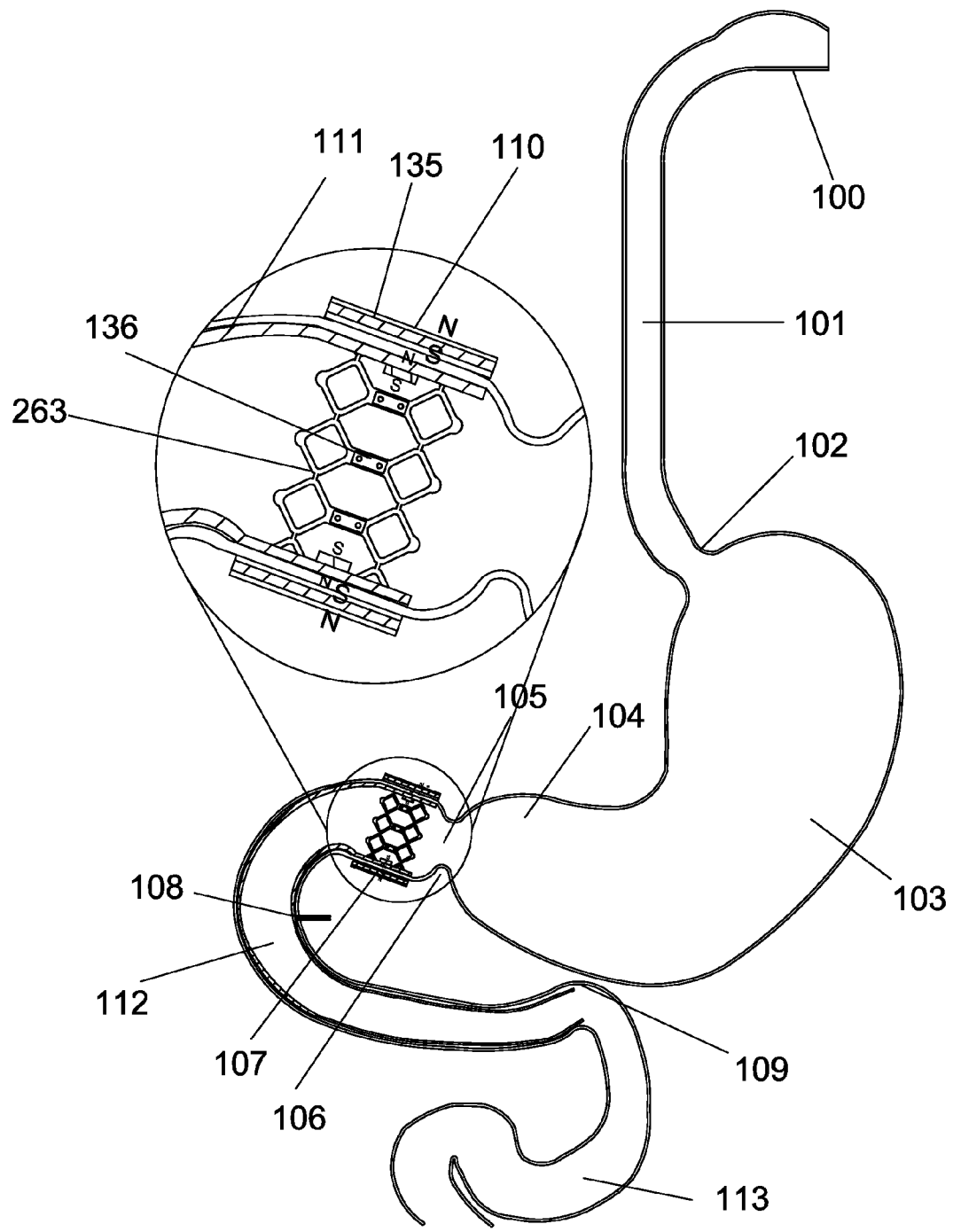
FIG. 26 is a sectional view of a portion of the digestive tract in the body. An external anchoring device is implanted around the duodenal bulb. An internal tubular implant is implanted from the duodenal bulb to the ligament of Treitz. The internal tubular implant uses a stent which has magnets integrated into it which attract to the magnets on the external band.

FIG. 26 is a sectional view of a portion of the digestive tract in a human body. An external band 110 is implanted around the duodenal bulb 107 and an internal tubular implant 111 is attached to the external band 110 and extended into the duodenum 112 or the jejunum 113 (e.g., to the ligament of Treitz 109). As shown, magnets 135 on the external band 110 and magnets 136 on the internal tubular implant 111 are magnetically attracted and secure the internal tubular implant 111 to the external band implant 110. In this embodiment, the internal tubular implant 111 includes and is coupled to a stent 263 (with magnets attached).

Figure 27:
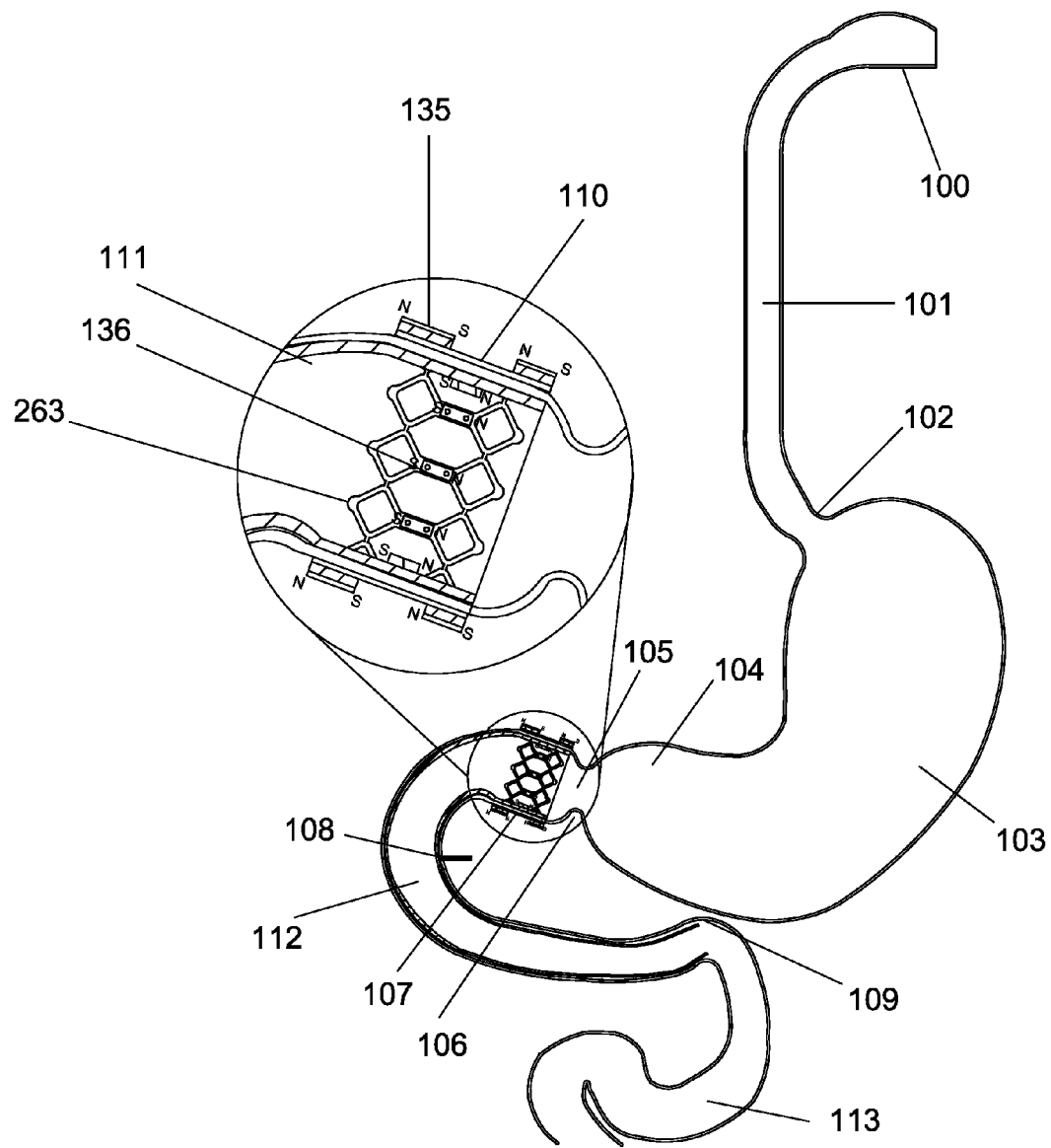
FIG. 27 is a sectional view of a portion of the digestive tract in the body. An external anchoring device is implanted around the duodenal bulb. An internal tubular implant is implanted from the duodenal bulb to the ligament of Treitz. The internal tubular implant uses a stent which has magnets integrated into it. The magnets on the external band and magnets on the internal band repel each other and limit movement or dislodgement of the internal tubular implant.

FIG. 27 is a sectional view of a portion of the digestive tract in a human body. An external band 110 is implanted around the duodenal bulb 107 and an internal tubular implant 111 is attached to the external band 110 and extended into the duodenum 112 or the jejunum 113 (e.g., to the ligament of Treitz 109). As shown, magnets 135 on the external band 110 and magnets 136 on the internal tubular implant 111 are magnetically repelled and secure the internal tubular implant 111 to the external band implant 110. Stent 263 (with magnets attached) is attached to internal tubular implant 111. In some embodiments, the stent 263 has an expanded outer diameter of generally equal to an inner diameter of the corresponding implant location of the gastrointestinal tract. According to some embodiments, the expanded outer diameter of the stent is within about ten percent, about five percent, or about two percent of the inner diameter of the corresponding implant location of the gastrointestinal tract.

FIGS. 28-31 show various embodiments of an external band 264 and an internal implant 111 configured for removably or reversibly coupling with each other. As shown, in each of these embodiments, the internal implant includes a portion including a feature or a structure adapted to mechanically couple with a corresponding (e.g., mating) feature or structure of the external band 264. In each case, the coupling is accomplished through or across a gastrointestinal organ or tissue (e.g., across the duodenum, the pylorus, or the gastric antrum), but without penetrating such tissue. In some embodiments, the external band 264 and the internal implant 111 are not in direct mechanical contact, but instead engage or couple with each other with intervening gastrointestinal tissue.

Figure 28:
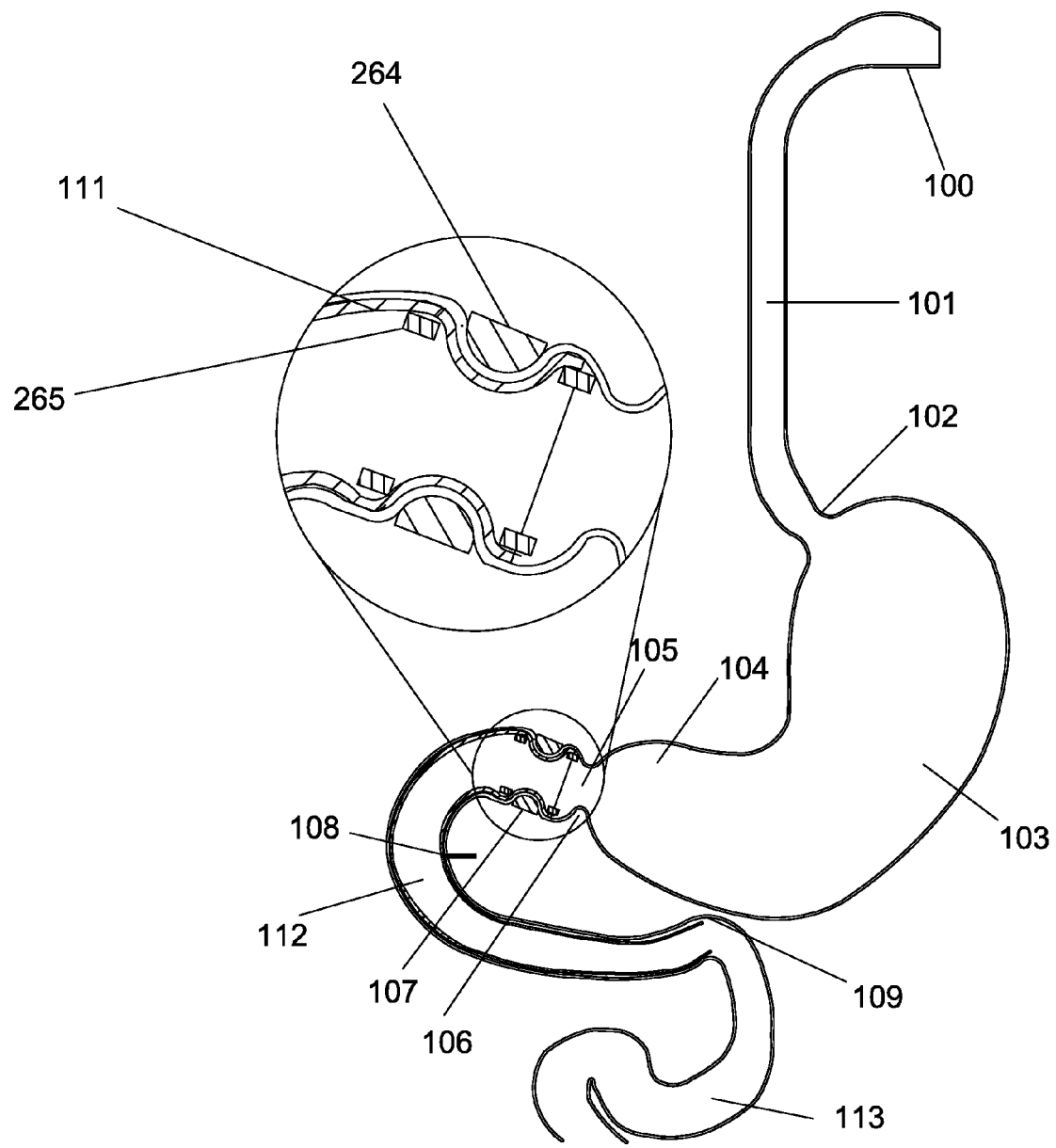
FIGS. 28-31 show sectional views of various embodiments of an external anchoring device implanted around the duodenal bulb. An internal tubular implant is implanted from the duodenal bulb to the ligament of Treitz. The internal tubular implant one of more expandable rings or stents to anchor the device inside of the duodenal bulb.

FIG. 28 is a sectional view of a portion of the digestive tract in a human body. An external band 264 is implanted around the duodenal bulb 107 and an internal tubular implant 111 is attached to the external band 264 and extended into the duodenum 112 or the jejunum 113 (e.g., to the ligament of Treitz 109). As shown, diameter interference between at least a portion of the external band 264 and internal implant 110 limit longitudinal movement without exerting substantial radial force on the gastrointestinal tract. As shown, the tubular implant 111 includes an expandable ring or stent 265, which is attached to the tube portion of the tubular implant 111 and operates to secure the internal tubular implant 111 to the external band 264.

Figure 29:
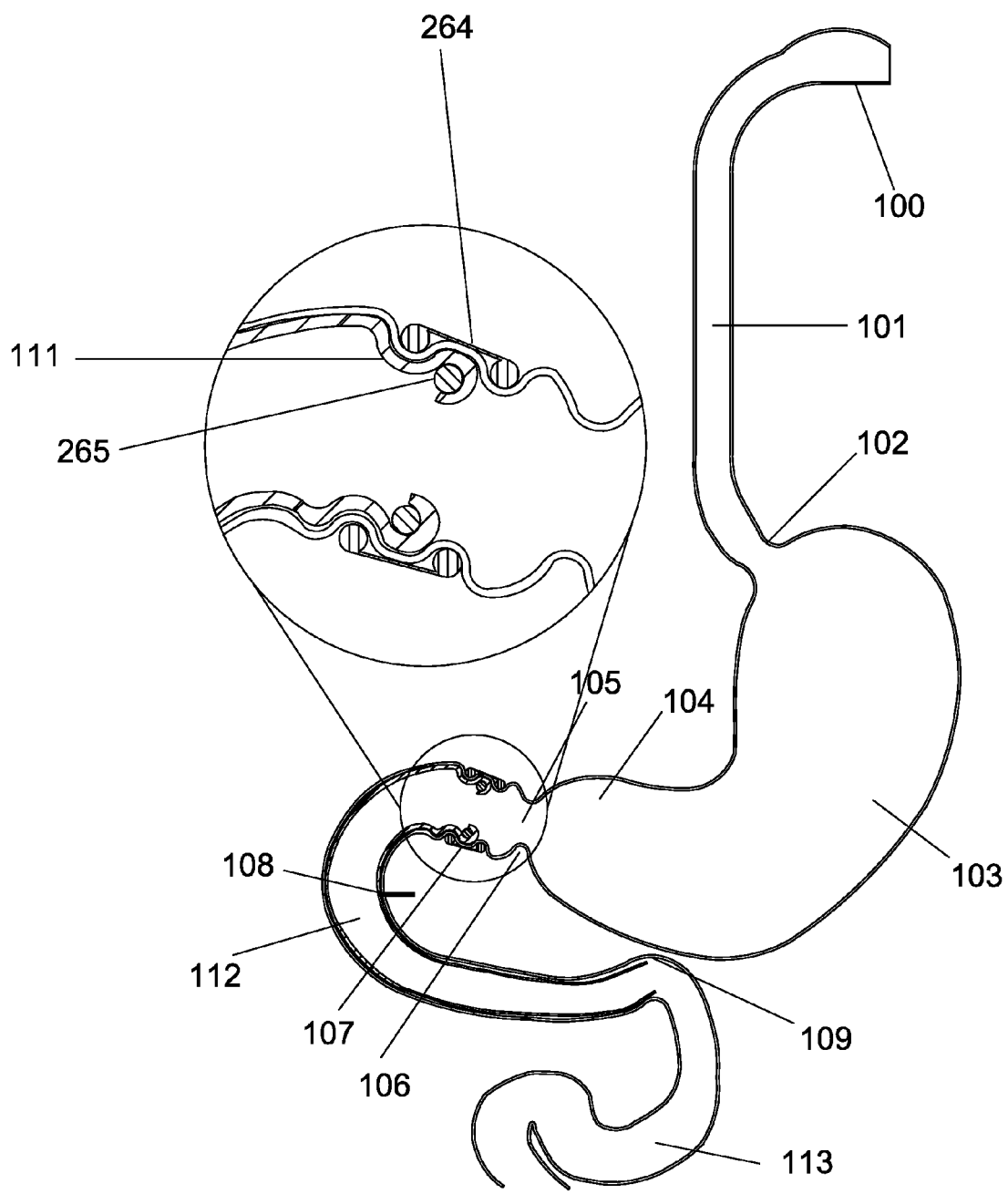

FIG. 29 is a sectional view of a portion of the digestive tract in a human body. An external band 264 is implanted around the duodenal bulb 107 and an internal tubular implant 111 is coupled to the external band and extended into the duodenum 112 or the jejunum 113 (e.g., to the ligament of Treitz 109). As shown, diameter interference with the external band 264 and internal implant 111 secure the implant 110 within the gastrointestinal system and limit longitudinal movement without exerting too much radial force. The tubular implant 111 includes an attached expandable ring or stent 265.

Figure 30:
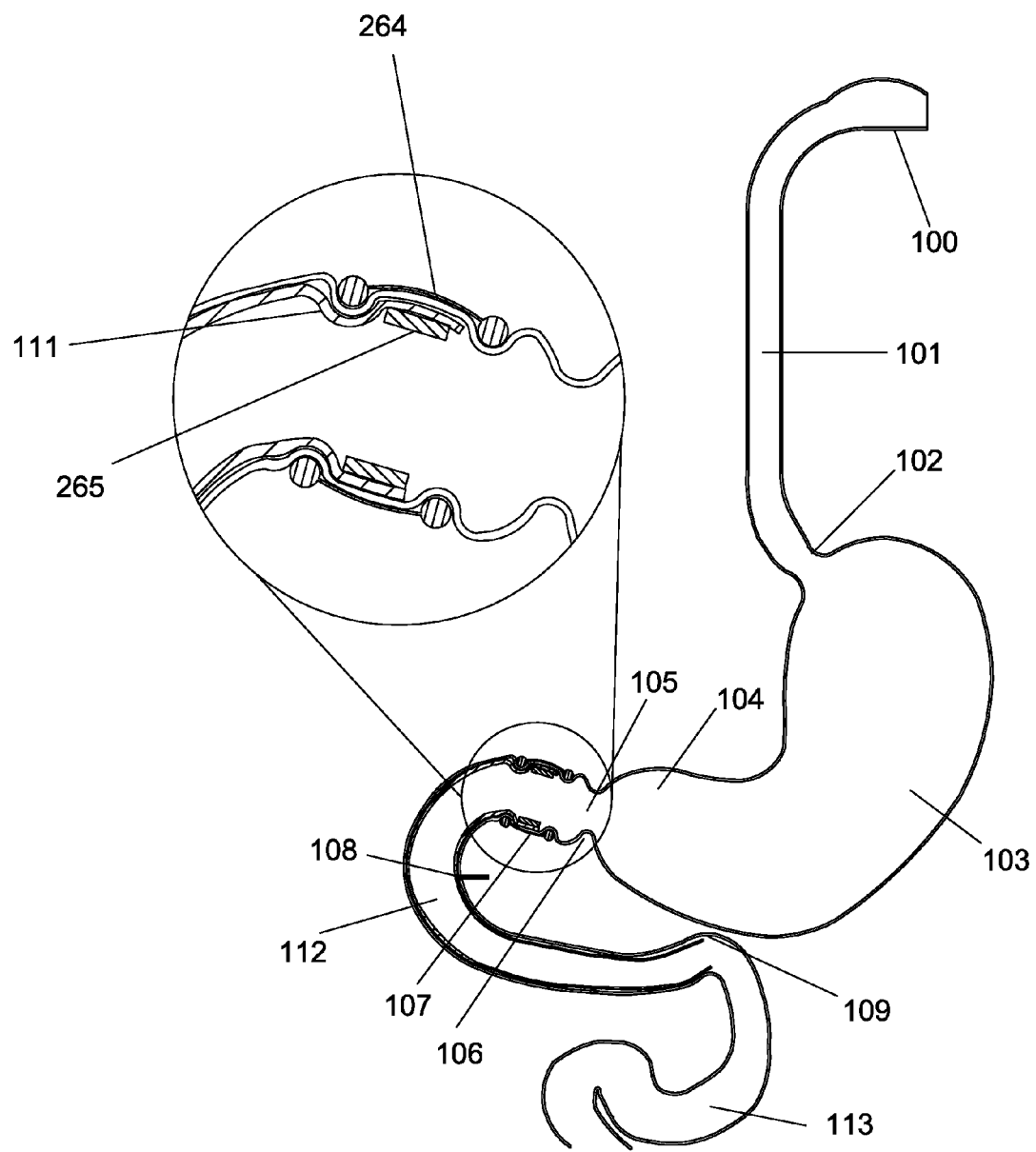

FIG. 30 is a sectional view of a portion of the digestive tract in a human body. An external band 264 is implanted around the duodenal bulb 107 and an internal tubular implant 111 is attached to the external band 264 and extended into the duodenum 112 or the jejunum 113 (e.g., to the ligament of Treitz 109). As shown, diameter interference with the external band 264 and internal implant 111 limit longitudinal movement without exerting too much radial force. Expandable ring/stent 265 is attached to internal tubular implant 111. According to exemplary embodiments, the external band 264 (of FIGS. 28-30) includes a portion or portions having a final, implanted inner diameter smaller than an outer diameter of a corresponding securing portion (e.g., the ring or stent 265) of the internal implant, such that, upon implantation, the external band 264 mates with, couples with, or otherwise interacts with the internal tubular implant 111 to prevent or resist longitudinal movement or migration of the tubular implant. Likewise, according to various embodiments, the ring of stent 265 has an expanded outer diameter of generally equal to an inner diameter of the corresponding implant location of the gastrointestinal tract. According to some embodiments, the expanded outer diameter of the stent is within about ten percent, about five percent, or about two percent of the inner diameter of the corresponding implant location of the gastrointestinal tract.

Figure 31:
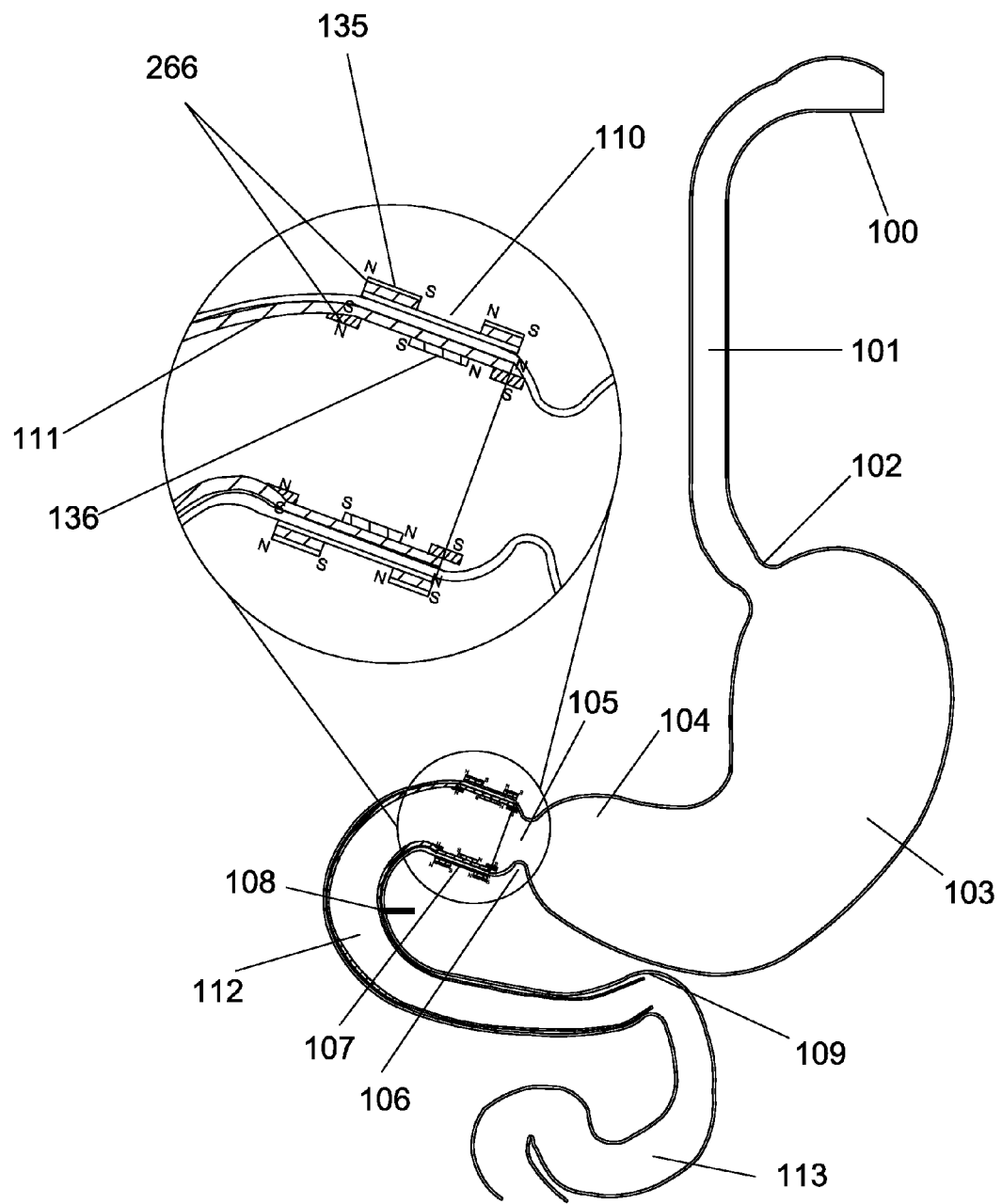

FIG. 31 is a sectional view of a portion of the digestive tract in a human body. An external band 110 is implanted around the duodenal bulb 107 and an internal tubular implant 111 is attached to the external band 110 and extended into the duodenum 112 or the jejunum 113 (e.g., to the ligament of Treitz 109). As shown, magnets 135 on the external band 110 and magnets 136 on the internal tubular implant 111 are magnetically repelled from each other and secure the internal tubular implant to the 111 to the external band implant 110. In various embodiments, the internal implant 111 also includes magnets 266, which are attracted to corresponding magnets on the external band 110.

Figure 32:
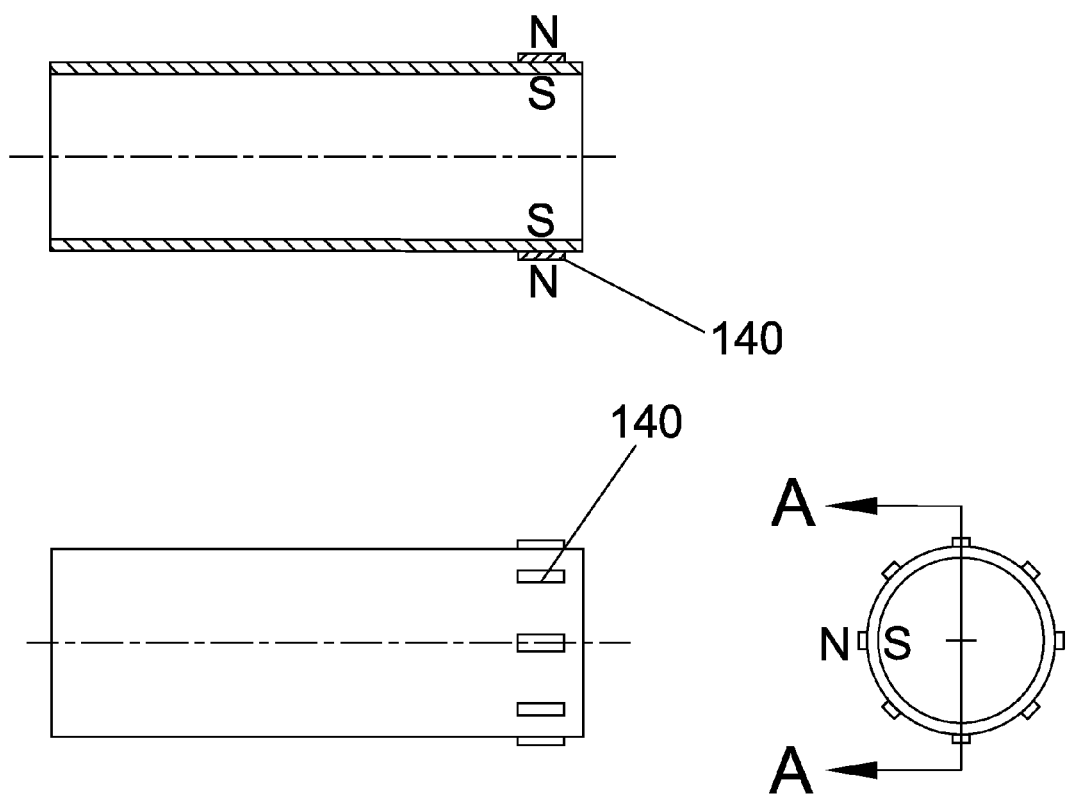
FIGS. 32-33 show tubular implants or sleeves including one or more magnets for attachment.
Figure 33:
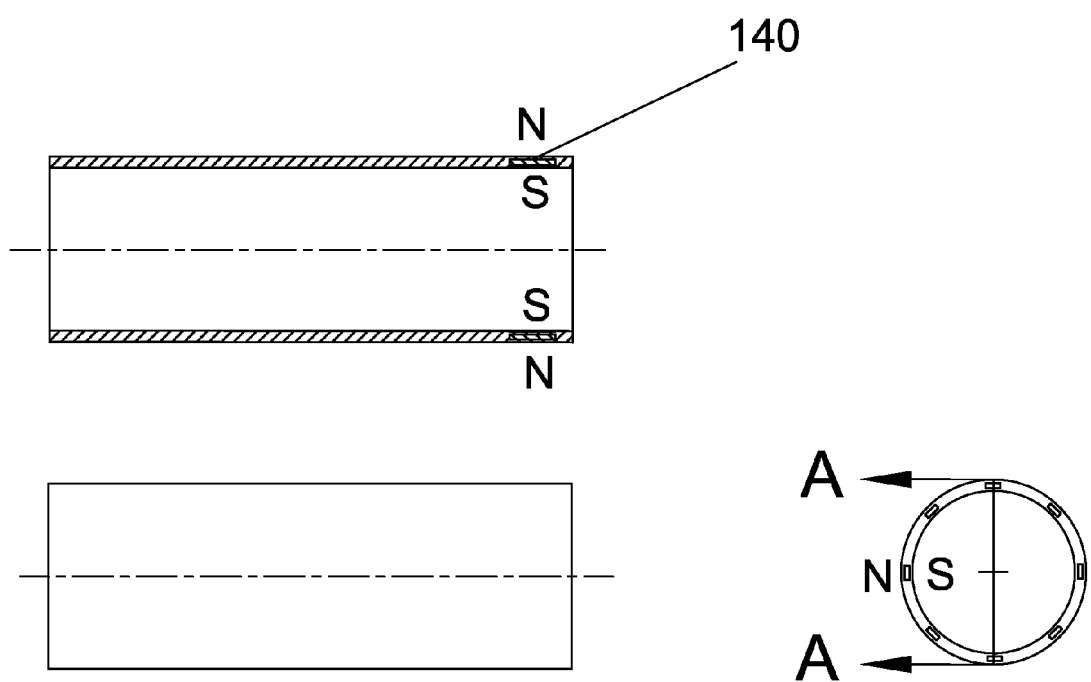

FIGS. 32-33 show various embodiments of an internal tubular implant. The tubular implant is designed to attach to another tubular implant or to an external band by a magnetic attachment means. In the embodiment of FIG. 32, the tubular implant has magnets 140 on the outside diameter. In the embodiment of FIG. 33, the tubular implant has magnets 140 in the wall thickness. In various embodiments, the magnets 140 are adapted for coupling the tubular implant to an external band, a docking element or another internal implant. Sections A-A in FIGS. 32 and 33 show sectional views of the tubular implant.

Figure 34:
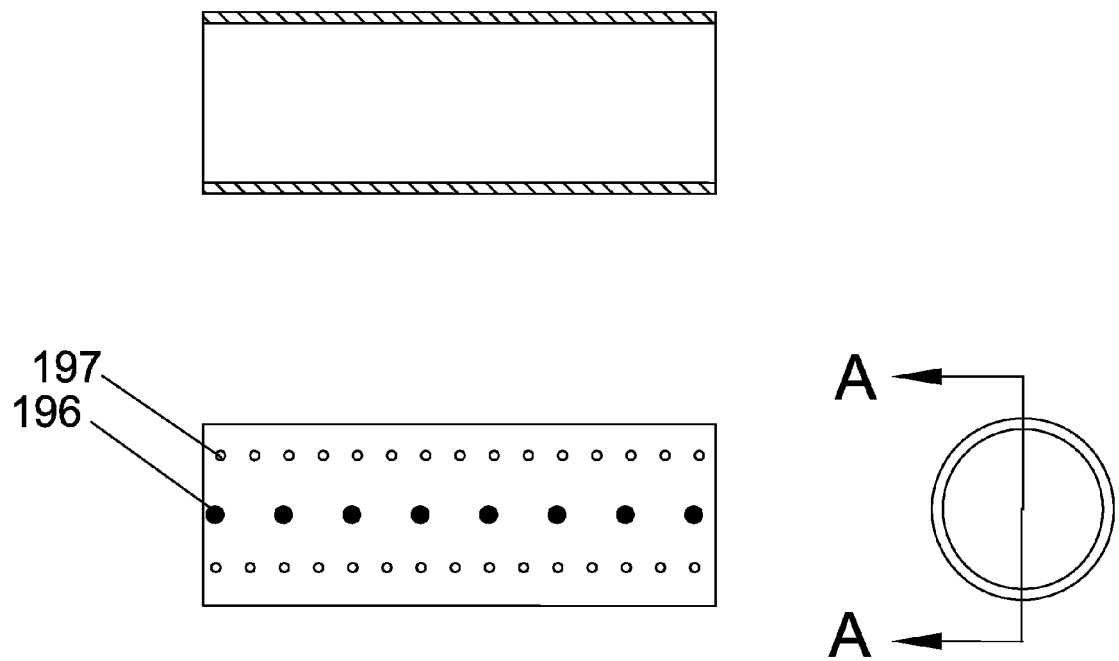
FIGS. 34-39 show various embodiments of an internal tubular implant sleeve.
Figure 35:
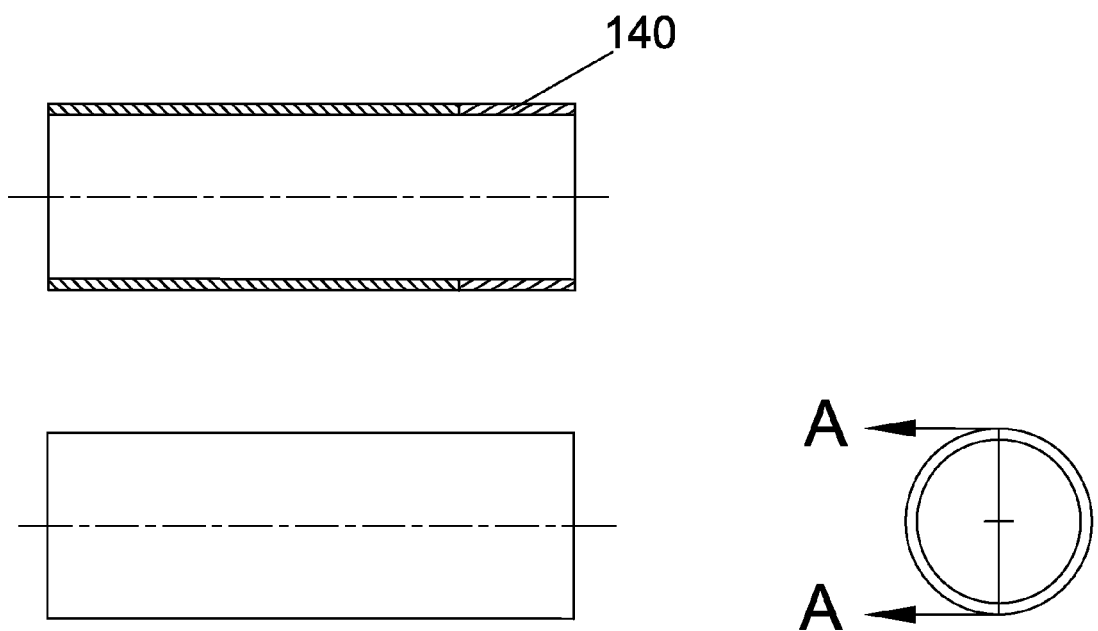
Figure 36:
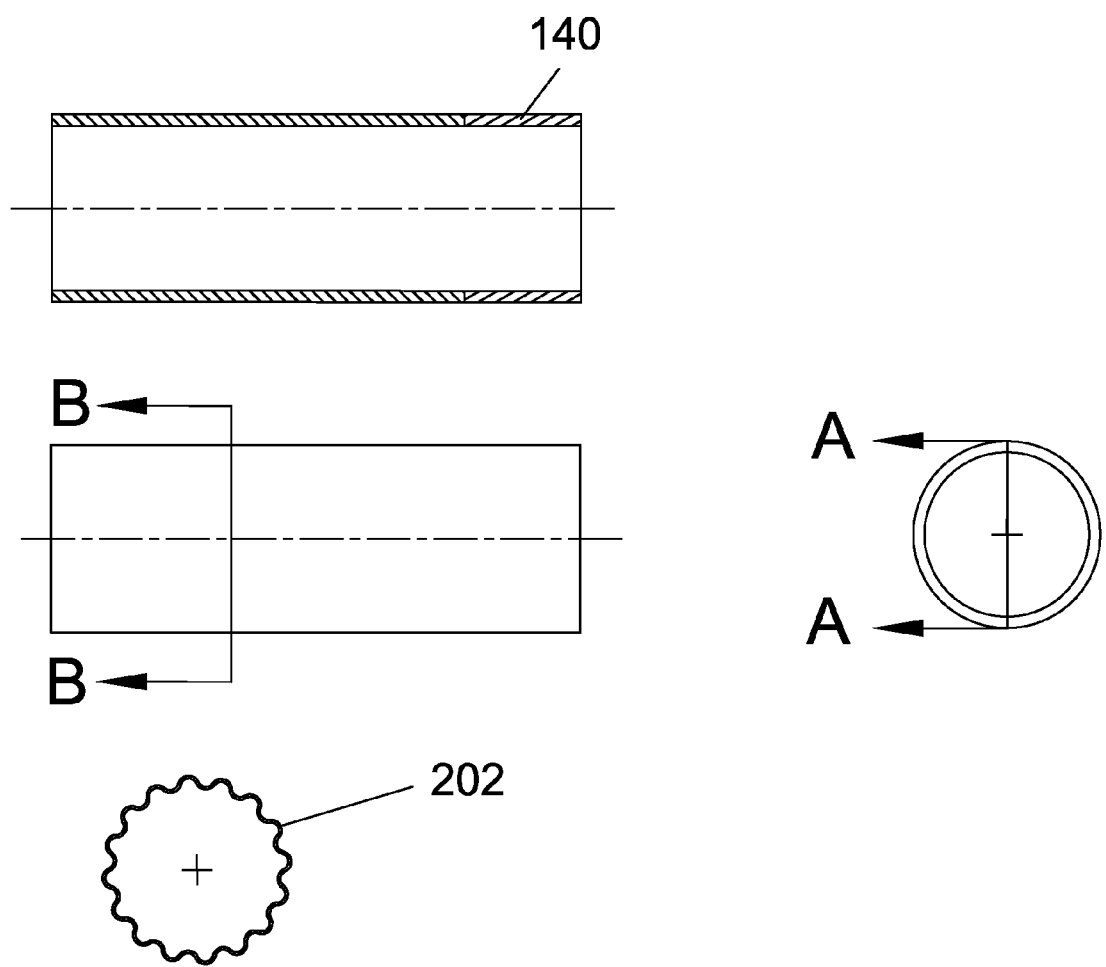
Figure 37:
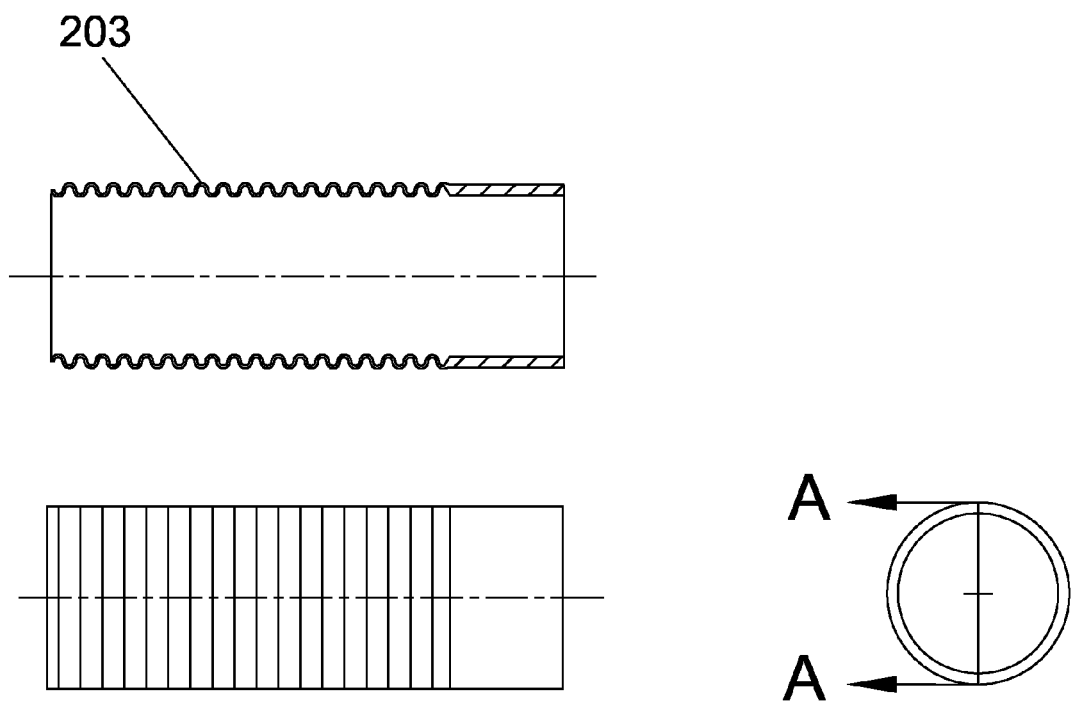

FIGS. 34-36 shows various embodiments of a simple sleeve used as a component of an internal tubular implant, or for extending a tubular implant. In the embodiment of FIG. 34, the sleeve has radio-opaque markers 196 and may have holes in the sleeve 197 to allow some fluid flow through the sleeve, if required. In the embodiment of FIG. 35, the sleeve has magnetic particles or ferromagnetic material 140 incorporated into the sleeve to allow attachment of the sleeve to a magnetic docking station or tubular implant. In the embodiment of FIG. 36, the sleeve has magnetic particles or ferromagnetic material 140 incorporated into the sleeve to allow attachment of the sleeve to a magnetic docking station or tubular implant. In various embodiments, the sleeve also has longitudinal pleats 202 in the surface to allow it to collapse in diameter more uniformly and may help to reduce the loaded profile. The longitudinal pleats maybe be over the entire length or just apportion of the diameter or length. In the embodiment of FIG. 37, the sleeve has pleats around the circumference 203. These circumferential pleats will allow the tubular implant or sleeve to bend easier without kinking. Sections A-A in FIGS. 34-36 show sectional views of the sleeve. Section B-B in FIG. 36 shows another sectional view of the sleeve.

Figure 38:
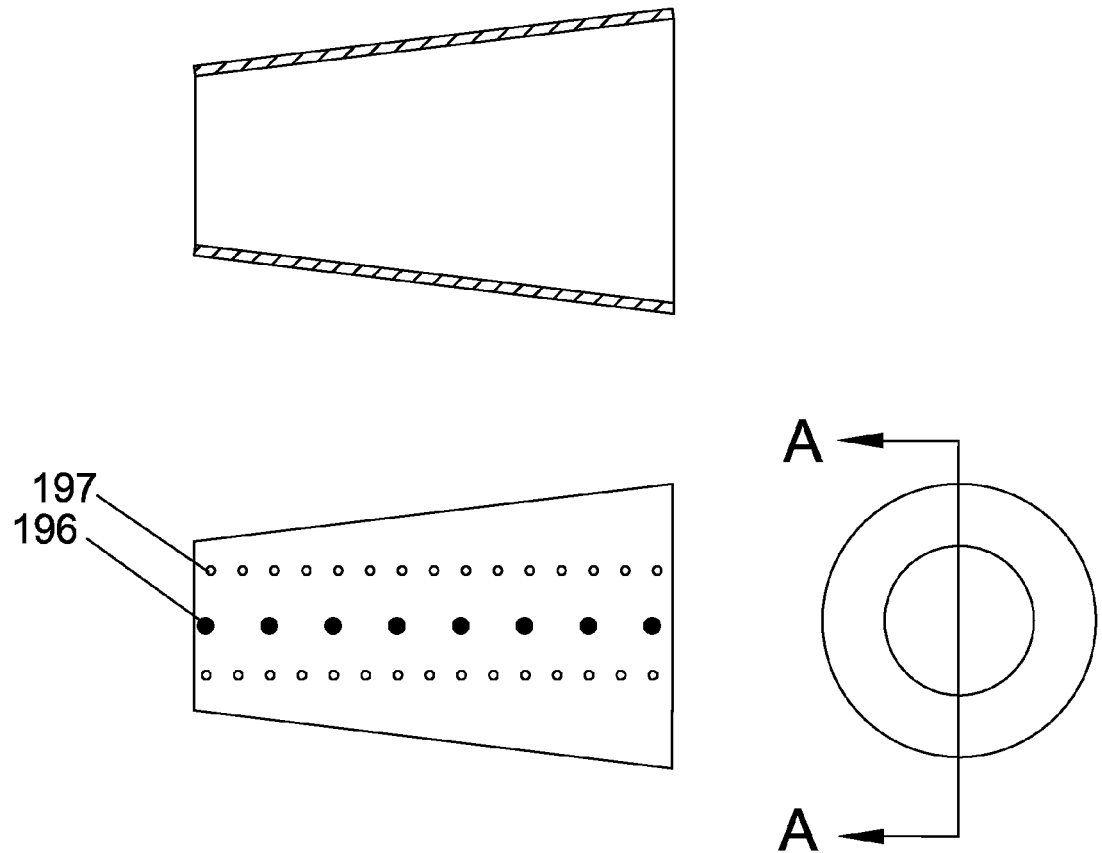

FIG. 38 is a simple sleeve with a conical diameter. The simple sleeve may be used as part of a docking station or tubular implant. Section A-A in FIG. 38 shows a sectional view of the sleeve.

Figure 39:
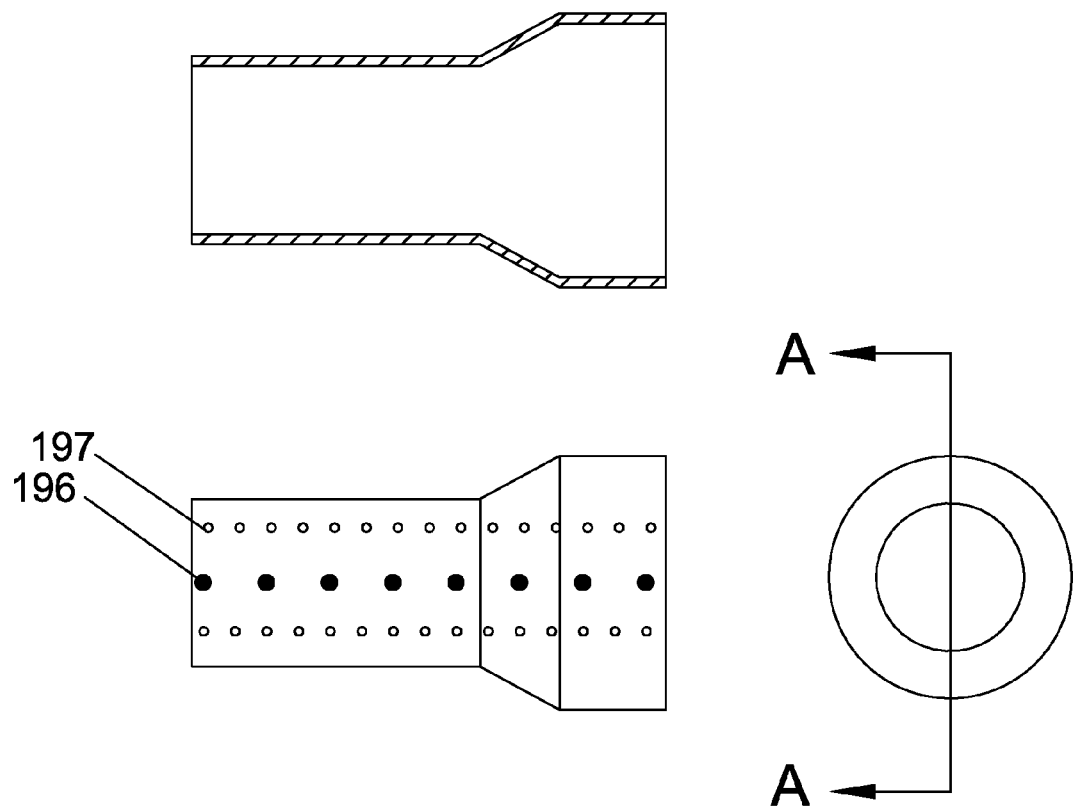

FIG. 39 is a simple sleeve with a stepped diameter. The simple sleeve may be used as part of a docking station or tubular implant. Section A-A in FIG. 39 shows a sectional view of the sleeve.

Figure 40:
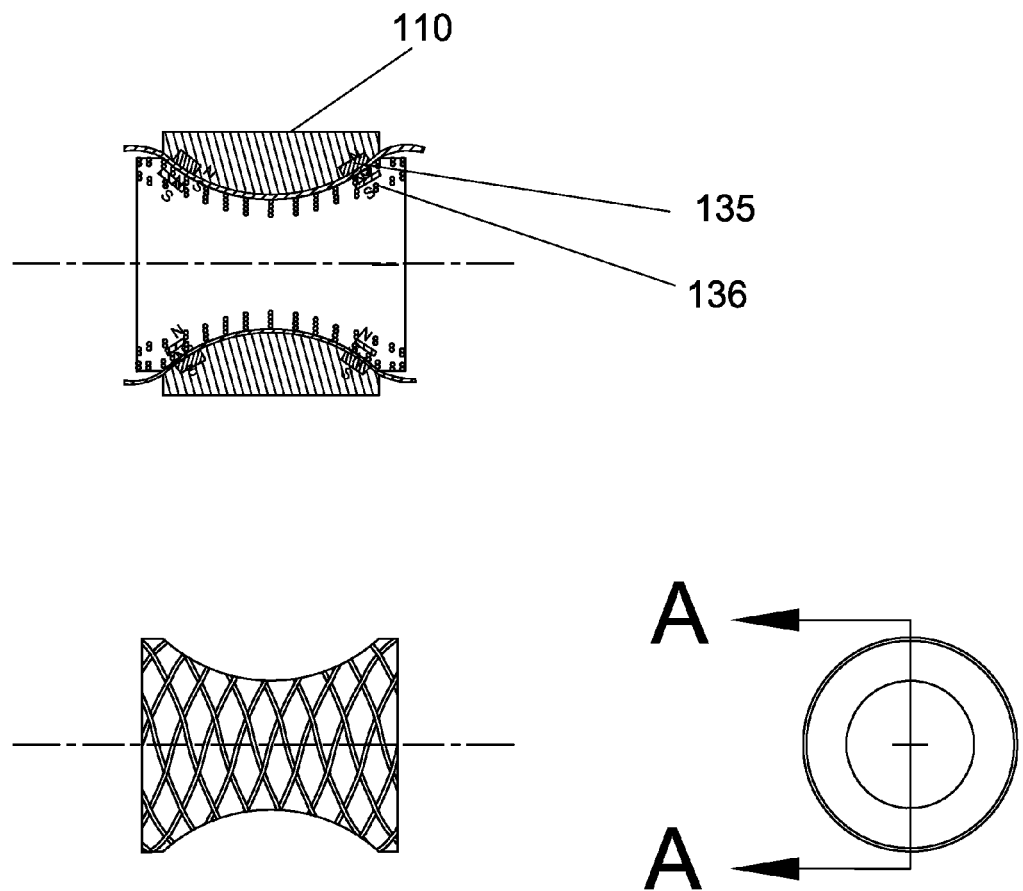
FIG. 40 shows a stent which may be used as an anchoring device for internal tubular implant. The stent may incorporate magnets that attract or repel portions of the external band. The stent device may also anchor the sleeve of the internal tubular implant by mechanical means.

FIG. 40 is a stent that can be used to couple with an external band 110. The stent may incorporate magnets to allow magnetic attract or repulsion to an external band. As shown, magnets 136 are associated with the stent and are configured to interact with magnets 135 associated with the external band 110. According to various embodiments, the stent is integrated with or otherwise adapted to couple with an internal implant. For example, the stent may serve as a docking element for a sleeve portion of the tubular implant. Section A-A in FIG. 40 shows a sectional view of the stent.

Figure 41A:
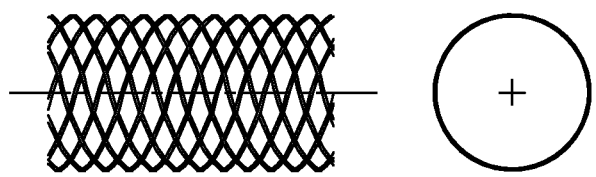
FIGS. 41A-48 show various embodiments of a stent that may be used as an anchoring device for an internal tubular implant.

FIG. 41A shows a stent that can be used with or as a part of an internal implant. The stent can be braided from round or flat wire. The drawing of the stent is in the expanded state. The mesh of the stent may be left open or it may be covered with a suitable material previously disclosed in this application. The stent may be balloon expanded or self expanding. The mesh of the stent may be left open or it may be covered with a suitable material previously disclosed in this application.

Figure 41B:
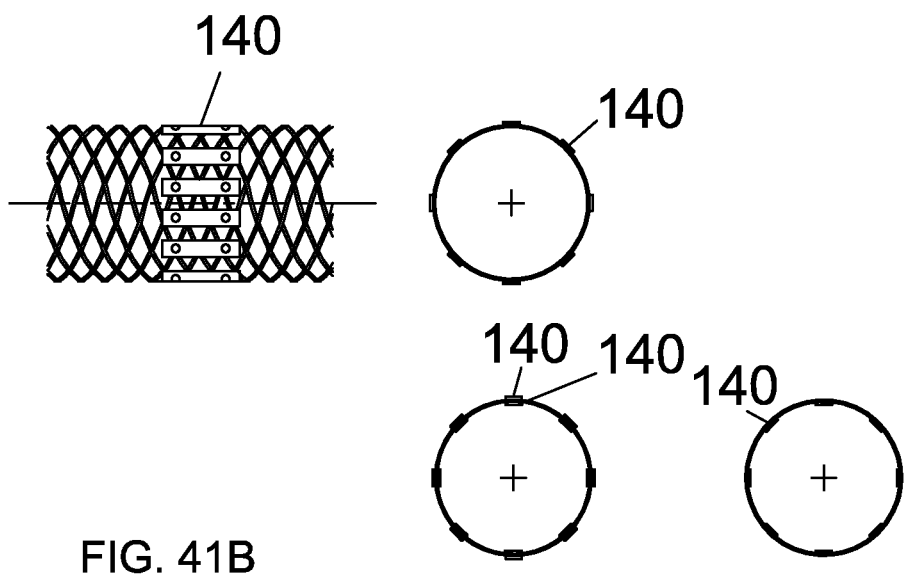

FIG. 41B shows a stent that can be used as a part of the internal implant. The stent can be braided from round or flat wire. The drawing of the stent is in the expanded state. The stent may include magnets 140 attached to the stent. The magnets 140 may be on the inside diameter, outside diameter, both the inside or outside diameter or incorporated into the wall. The magnets 140 can be used as a means to attach a tubular implant, such as 111. The mesh of the stent may be left open or it may be covered with a suitable material previously disclosed in this application. The stent may be balloon expanded or self expanding. The mesh of the stent may be left open or it may be covered with a suitable material previously disclosed in this application.

Figure 42A:
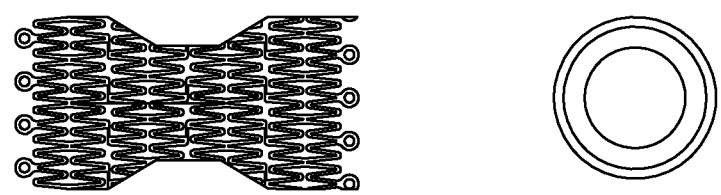

FIG. 42A shows a stent that can be used as part of an internal implant. In various embodiments, the stent is laser cut from round metal tubing or from a flat sheet of metal. The central portion of the stent's diameter may be set to a smaller diameter to provide increased resistance to stent migration. The stent may be balloon expanded or self expanding. The mesh of the stent may be left open or it may be covered with a suitable material previously disclosed in this application.

Figure 42B:
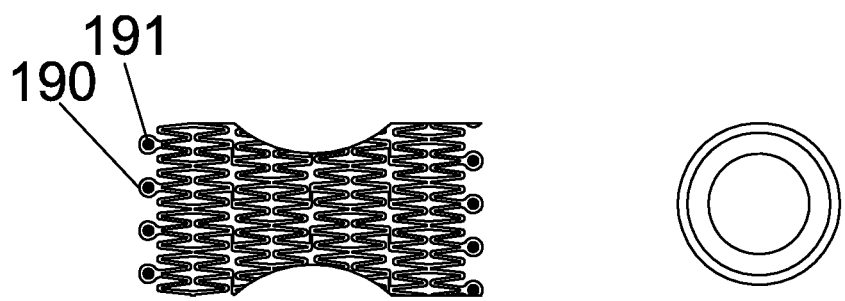

FIG. 42B shows a stent that can be used as a part of an internal implant. According to various embodiments, the stent is laser cut from round metal tubing or from a flat sheet of metal. The central portion of the stent's diameter may be shaped into an hour glass shape to provide increased resistance to stent migration. The stent has hoops 190 at the end of the stent. The hoops may be used to interlock with a stent retainer 159 on the inner catheter 152 to prevent premature deployment before the sheath is fully retracted. Radiopaque markers 191 can be attached to the end of the stent to increase the radio-opacity of the stent. A metal insert may be pressed/swaged into the hoops 190. The insert may be made from a high atomic density material, such as tantalum, gold, platinum or iridium. The insert may take the form of a disk or sphere and may be plastically deformed to fill the hoop cavity. The stent may be balloon expanded or self expanding. The mesh of the stent may be left open or it may be covered with a suitable material previously disclosed in this application. According to various embodiments, the stent of FIG. 42A or 42B includes a narrow central portion adapted to generally fit within an align with the pylorus.

Figure 43A:
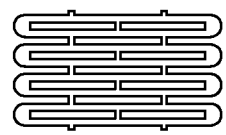
Figure 43A:
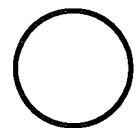
Figure 43B:
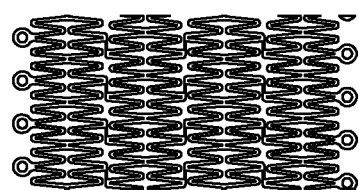
Figure 43B:
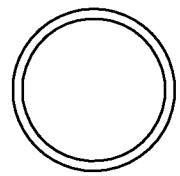

FIGS. 43A and 43B show embodiments of a stent that can be used as a part of an internal implant docking element. According to various embodiments, the stent is laser cut from round metal tubing or from a flat sheet of metal. The stent may be balloon expanded or self expanding. The mesh of the stent may be left open or it may be covered with a suitable material previously disclosed in this application.

Figure 44A:
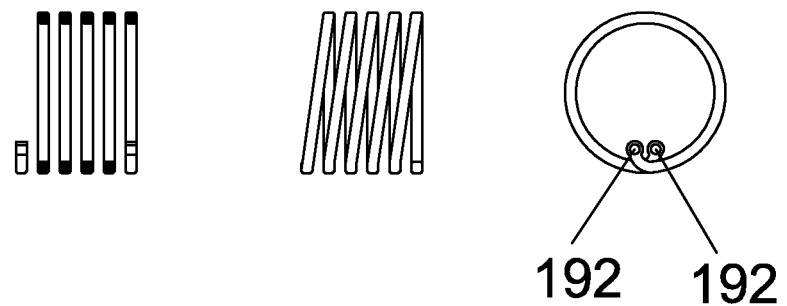
Figure 44B:
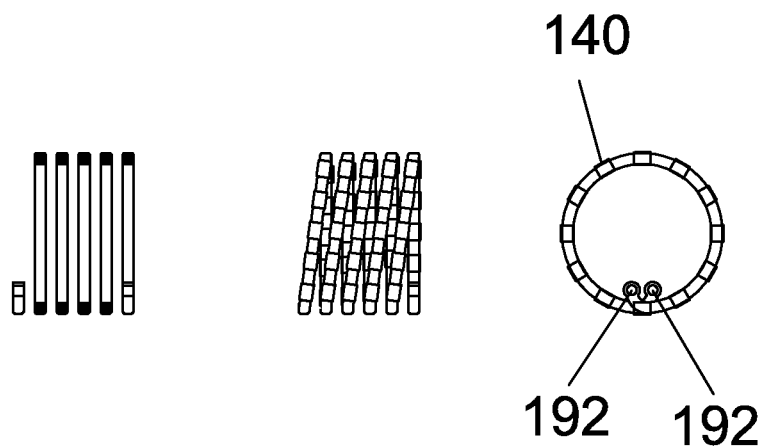

FIG. 44A shows a coil stent that can be used as a part of an internal implant. According to various embodiments, the stent is made from round or flat wire. The stent may be self expanding or balloon expandable. The stent also may be laser cut into a coil from tubing. According to various embodiments, the stent is made from nitinol. The mesh of the stent may be left open or it may be covered with a suitable material previously disclosed in this application. The stent has a hoop 192 at each end of the coil. The stent can be wound down onto a catheter by inserting a pin into the hoops on each end of the stent and rotating the pins in opposite directions to cause the stent to wind down onto the catheter. In the embodiment of FIG. 44B, the stent has magnets 140 on the coil of the stent. The magnets can be used as an attachment means to a tubular implant.

Figure 45:
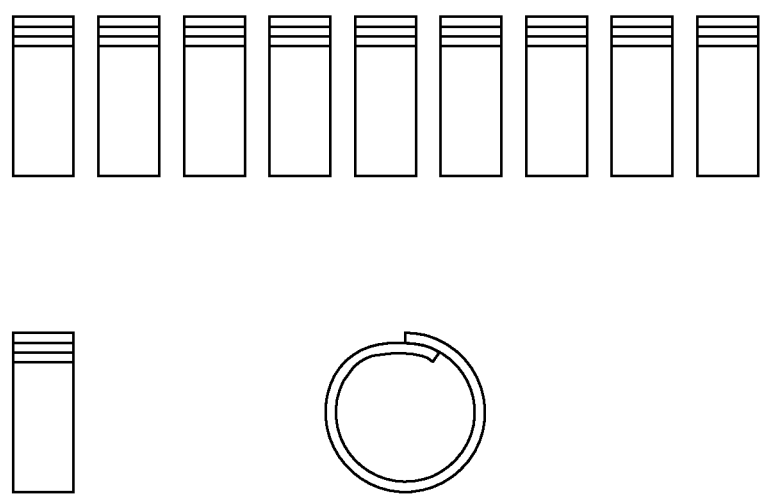

FIG. 45 shows a coil stent that can be used as a part of an internal implant. According to various embodiments, the stent is made from wire or sheet nitinol metal. Several stents in series adjacent to each other can be used to form the docking element.

Figure 46A:
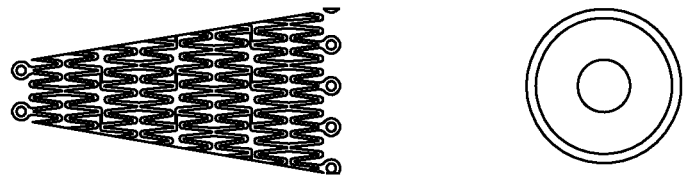
Figure 46B:
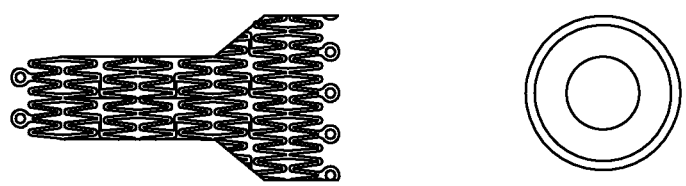

FIG. 46A shows a stent that can be used as a part of an internal implant. According to various embodiments, the stent is laser cut from round metal tubing or from a flat sheet of metal. The stent may be balloon expanded or self expanding. The mesh of the stent may be left open or it may be covered with a suitable material previously disclosed in this application. As shown in FIG. 46A, the stent is shaped to a conical shape to provide increased resistance to stent migration and to more closely fit the anatomy. As shown in FIG. 46B, the stent is shaped to a have a stepped diameter to provide increased resistance to stent migration and to more closely fit the anatomy.

Figure 47A:
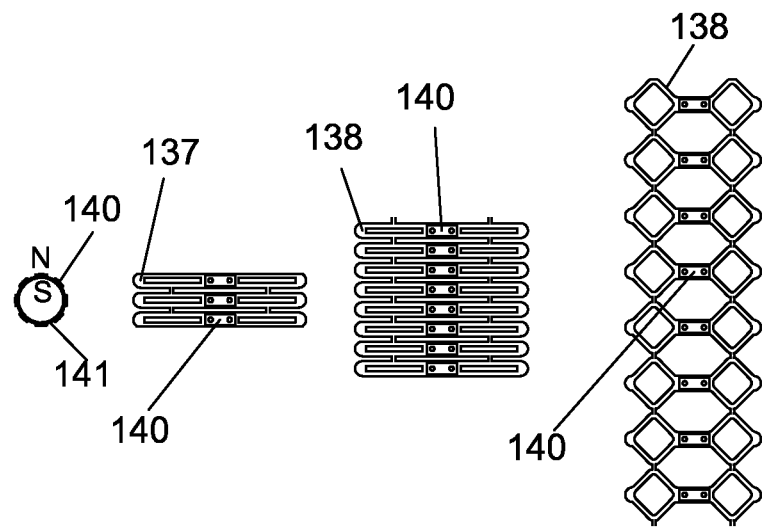

FIG. 47A shows a stent that can used as a part of an internal implant. The stents of this invention can be comprised of one or more of the following materials: Nickel titanium alloys (Nitinol), Stainless steel alloys: 304, 316L, BioDur® 108 Alloy, Pyromet Alloy® CTX-909, Pyromet® Alloy CTX-3, Pyromet® Alloy 31, Pyromet® Alloy CTX-1, 21Cr-6Ni-9Mn Stainless, 21Cr-6Ni-9Mn Stainless, Pyromet Alloy 350, 18Cr-2Ni-12Mn Stainless, Custom 630 (17Cr-4Ni) Stainless, Custom 465® Stainless, Custom 455® Stainless, Custom 450® Stainless, Carpenter 13-8 Stainless, Type 440C Stainless, Cobalt chromium alloysMP35N, Elgiloy, L605, Biodur® Carpenter CCM alloy, titanium and titanium alloys, Ti-6A14V/ELI and Ti-6A1-7Nb, Ti-15Mo tantalum, tungsten and tungsten alloys, pure platinum, platinum-Iridium alloys, platinum-nickel alloys, niobium, iridium, Conichrome, gold and gold alloys. The stent may also be comprised of one or more of the following absorbable metals: pure iron and magnesium alloys. The stent may also be comprised of the following plastics: polyetheretherketone (PEEK), polycarbonate, polyolefins, polyethylenes, polyether block amides (PEBAX), nylon 6, 6-6, 12, polypropylene, polyesters, polyurethanes, polytetrafluoroethylene (PTFE) poly(phenylene sulfide) (PPS), poly(butylene terephthalate) PBT, polysulfone, polyamide, polyimide, poly(p-phenylene oxide) PPO, acrylonitrile butadiene styrene (ABS), polystyrene, poly(methyl methacrylate) (PMMA), polyoxymethylene (POM), ethylene vinyl acetate, styrene acrylonitrile resin, polybutylene. The stent may also be comprised of the following absorbable polymers: polyglycolic acid (PGA), polylactide (PLA), poly(e-caprolactone), poly (dioxanone) poly(lactide-coglycolide).

According to various embodiments, the stent 137 stent is laser cut from a round tubing or from a flat sheet of metal. The flat representation of the stent circumference is shown in item 138. The flat representation of an expanded stent is shown in item 139. The end view of the stent is shown 141. Magnets 140 are attached to the stent on the outside diameter. The magnets 140 may be attached to the stent by use of a mechanical fastener, glue, suture, welding, snap fit or other suitable means. The stent can be either balloon expandable or self expanding. The magnets may be located in middle of the stent or at the ends of the stent. Suitable materials for the magnets include: neodymium-iron-boron [Nd—Fe—B], samarium-cobalt [Sm—Co], alnico, and hard ferrite [ceramic] or other suitable material.

Figure 47B:
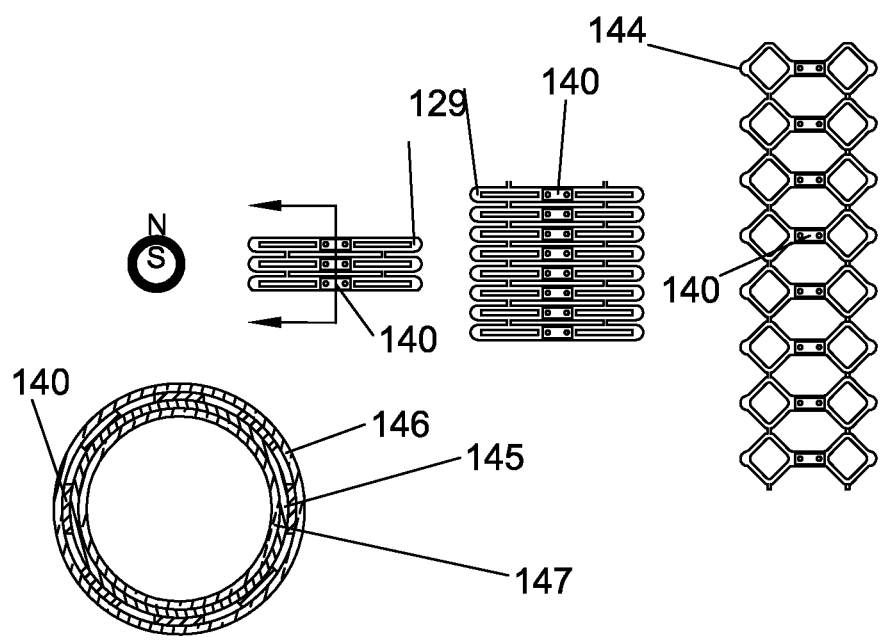

FIG. 47B shows a stent that can used as a part of an internal implant. Stent 142 may be laser cut from a round tubing or from a flat sheet of metal. The flat representation of the stent circumference is shown in item 143. The flat representation of an expanded stent is shown in item 144. The end view of the stent is shown 145. Permanent magnets 140 are attached to the stent on the outside diameter. This stent is a covered stent. The stent covering is not shown on items 142, 143 or 144. The covering are shown on the end view which shows stent 145. Stent may have an outside covering 146, inside covering 147 or both. Suitable materials for the covering include, but are not limited to: silicone, polyether block amides (PEBAX), polyurethanes, silicone polyurethane copolymers, nylon 12, polyethylene terphalate (PET), ePTFE, Kevlar, Spectra, Dyneena, polyvinyl chloride (PVC), polyethylene or polyester elastomers. The coverings may be dip coated onto the stent or they may be made as a separate tube and then attached to the stent by adhesives or mechanical fasteners, such as suture, rivets, or by thermal bonding of the material to the stent or another layer. The covering may also have drugs incorporated into the polymer to provide for a therapeutic benefit. The covering 146 or 147 may also be of biologic origin. Suitable biologic materials include, but are not limited to: Amnion, Collagen Type I, II, HI, IV, V, VI—Bovine, porcine, ovine, placental tissue or placental veins or arteries and small intestinal sub-mucosa.

Figure 48:
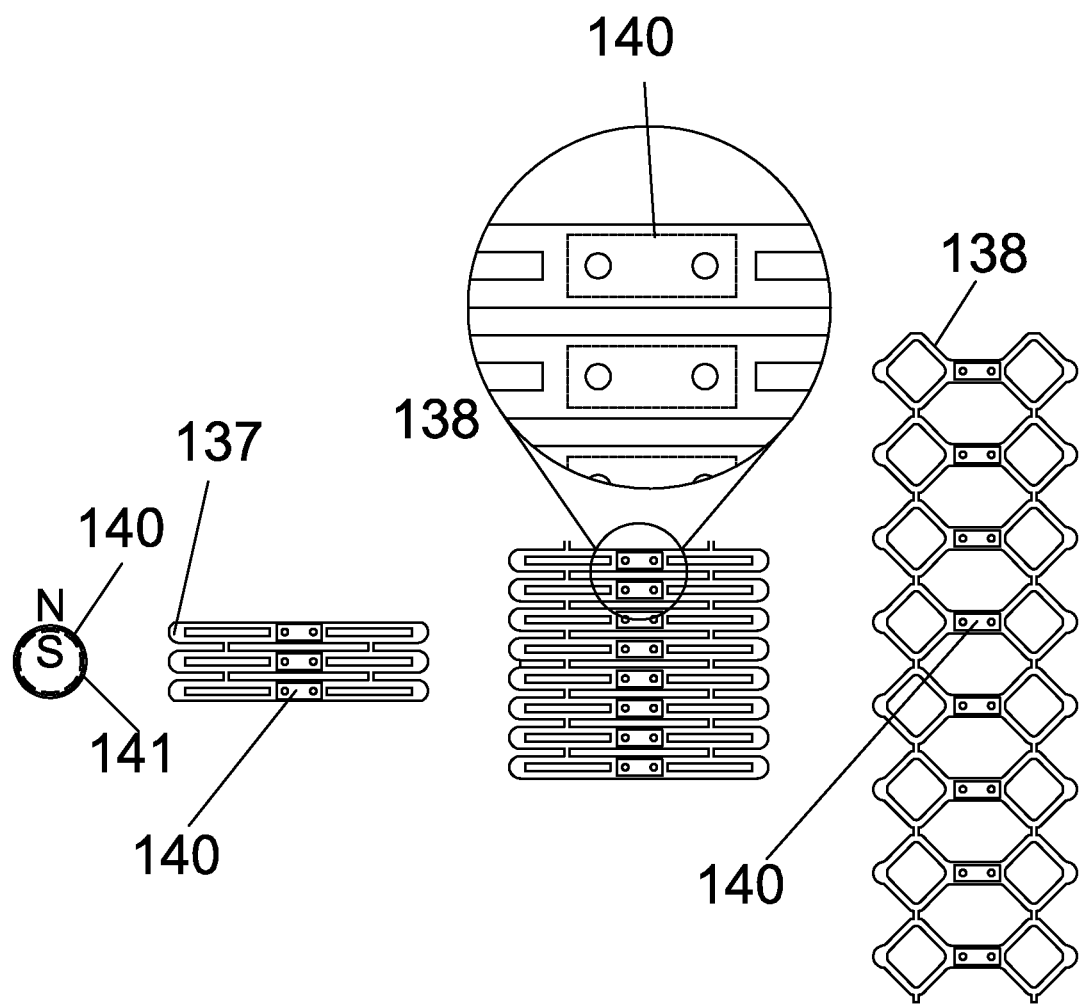
Figure 49:
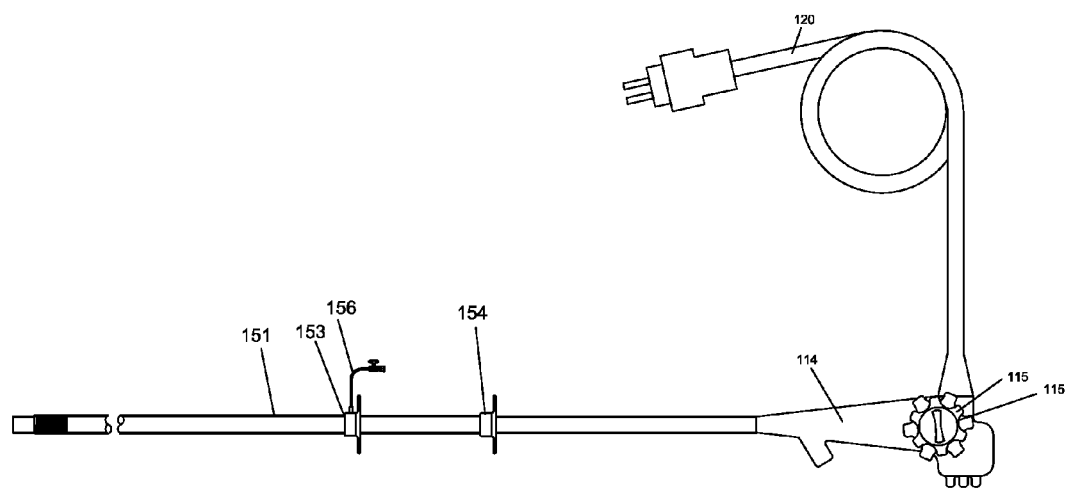
FIG. 49 shows a delivery device for an internal tubular implant that is designed to go over the outside of an endoscope. The delivery device is loaded over the outside of an endoscope.

FIG. 48 shows a stent that can used as a part of an internal implant. Stent may be laser cut from a round metal tubing or from a flat sheet of metal. The flat representation of the stent circumference is shown in item 138. The flat representation of an expanded stent is shown in item 137. The end view of the stent is shown 141. Magnets 140 are attached to the stent on the inside diameter. The magnets may be attached to the stent by use of a mechanical fastener, glue, suture, welding, snap fit or other suitable means. The stent can be either balloon expandable or self expanding. The magnets may be located in middle of the stent or at the ends of the stent. Suitable materials for the magnets include: neodymium-iron-boron [Nd—Fe—B], samarium-cobalt [Sm—Co], alnico, and hard ferrite (ceramic) or other suitable material. The stent may be balloon expanded or self expanding FIG. 49 shows the delivery catheter for the apparatus disclosed loaded over an endoscope.

Figure 50:
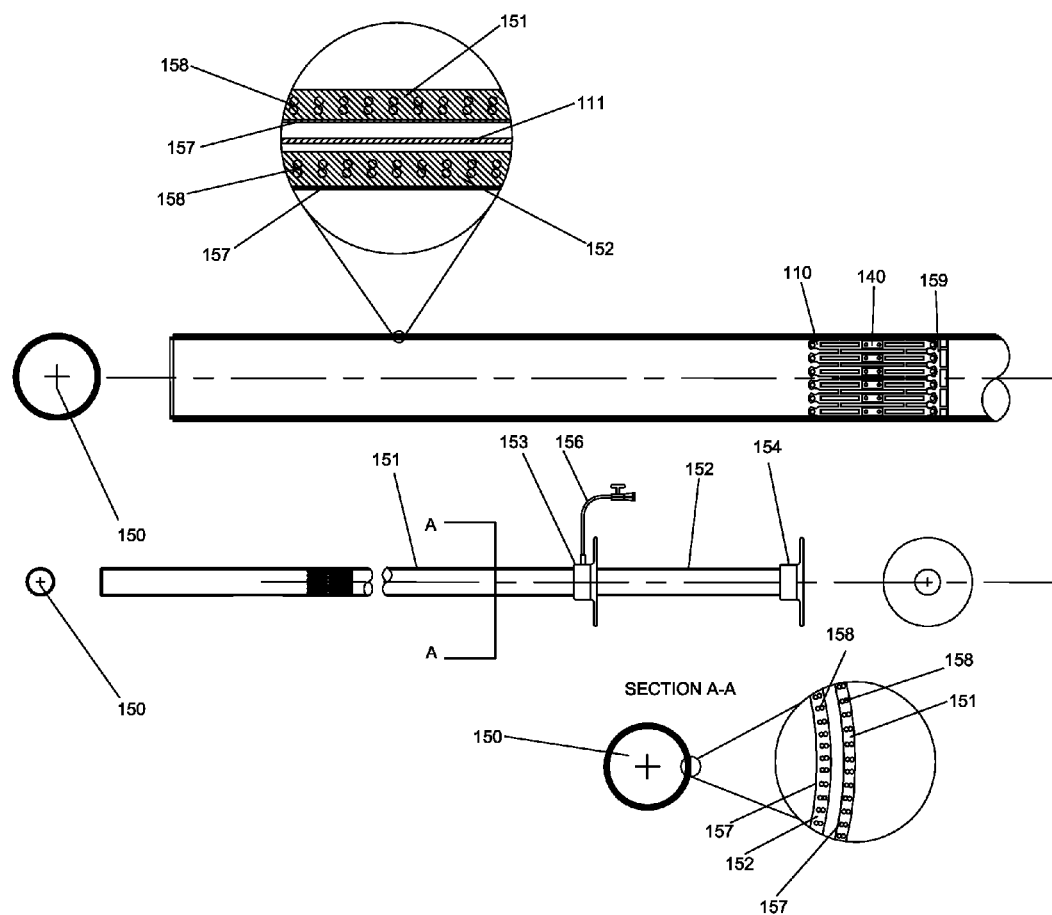
FIGS. 50-51 show various embodiments of a delivery device for an internal tubular implant.

FIG. 50 shows an alternative embodiment drawing of a delivery catheter for a self expanding internal tubular implant. The tubular implant is located distal to the docking element. The delivery catheter could also be used for delivery of a stented sleeve construct where the sleeve and stent are integrated together into one implant. The delivery catheter is constructed with a central lumen 150 large enough to allow the catheter to be loaded over the outside diameter of the endoscope 114. The delivery catheter consists of an outer catheter 151 and an inner catheter 152.

To load the tubular implant onto the delivery catheter the outer sheath handle 153 is retracted towards the inner catheter handle 154 until distance is a small as possible. The outer sheath is then partially closed by advancing the outer sheath handle 153 away from the inner sheath handle 154. Continue advancing the outer sheath 151, when the tubular implant is completely covered by the outer sheath 151, the loading process is complete for the tubular implant. The delivery catheter also has a space on the inner catheter for the modular implant to be loaded. Attached to the inner catheter is a stent retainer 159. The purpose of the stent retainer 159 is to prevent the stent from releasing from the delivery catheter prematurely during deployment. The stent retainer 159 is fastened to the inner catheter. The stent retainer 159 can be made from metal or plastic and can be made radio-opaque by making it from a radio-opaque material such as tantalum. The stent retainer 159 has a complementary shape that holds the tips on the stent and does not allow the stent to move distally or forward until the outer sheath 151 is fully retracted to the stent retainer 159. The catheter has a side port 156 which allows the space between the inner and outer sheaths to be flushed with saline. The outer sheath 151 and inner sheath 152 may be made from a simple single layer polymer extrusion, such as from polyethylene or PTFE. The outer sheath 151 may also be constructed in the following manner. The sheath inner diameter surface is constructed of a thin wall PTFE liner 157. A layer of reinforcement 158 is placed over the PTFE liner 157. According to various embodiments, the reinforcement is either a braid of wire or a coil of wire. The wire cross-section can be either round or rectangular. In some embodiments, the wire is made from a metal such as 316, 304 stainless steel, Nitinol, or other suitable material. The wire diameters are typically in the 0.0005 inch to 0.010 inch diameter range. The outer jacket material may be reflowed into the reinforcement layer by melting the material and flowing the melted polymer into the spaces in between the braided wire or the coiled wires.

Figure 51:
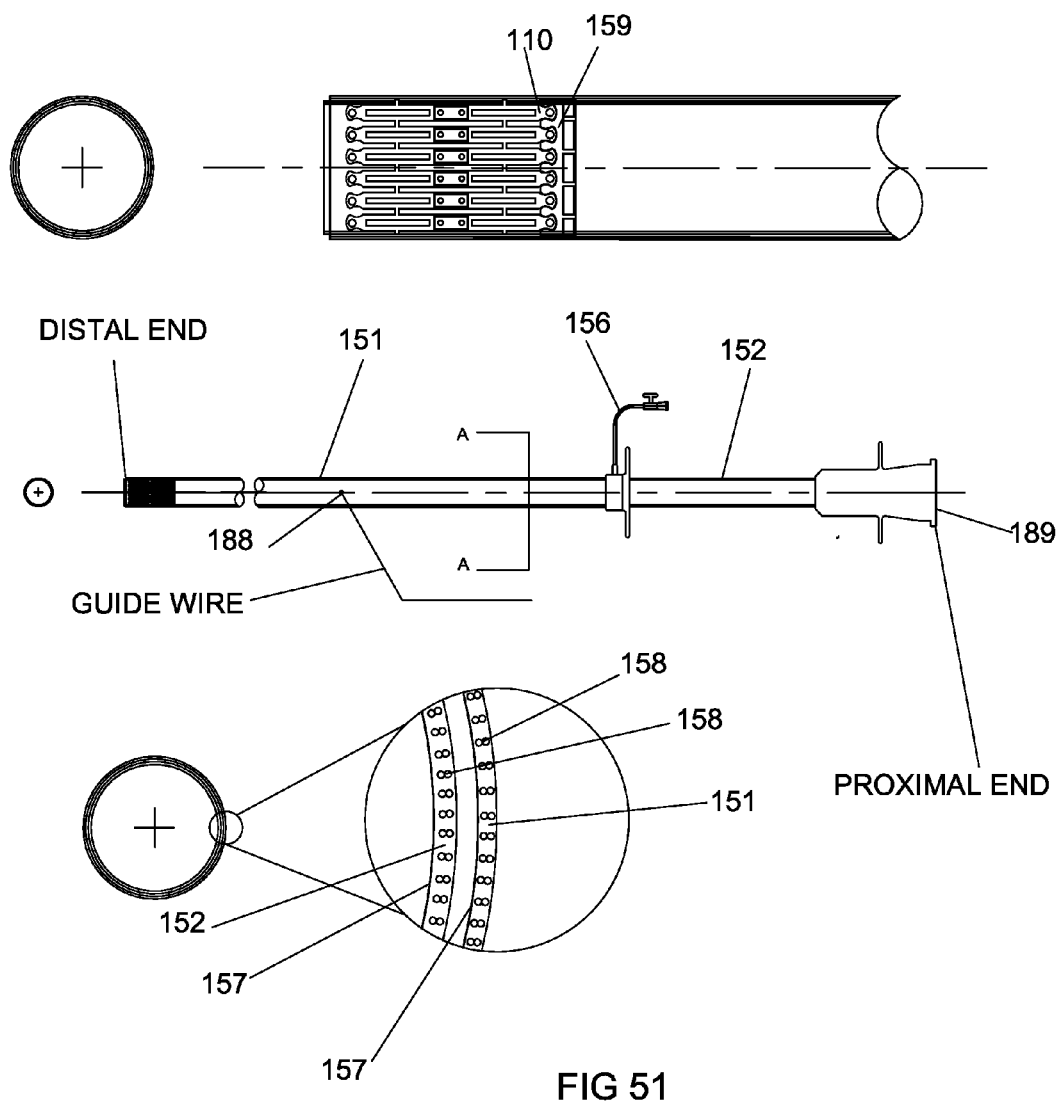

FIG. 51 shows an alternative embodiment of a delivery catheter for a self expanding internal tubular implant or for both 110 and 111 on the same catheter. The delivery catheter is constructed with a smaller outside diameter to allow the catheter to be inserted through the working channel of the endoscope 114. The delivery catheter consists of an outer catheter 151 and an inner catheter 152. Attached to the inner catheter is a stent retainer 159. The purpose of the stent retainer 159 is to prevent the stent from releasing from the delivery catheter prematurely during deployment. The stent retainer 159 is fastened to the inner catheter. The stent retainer 159 can be made from metal or plastic and can be made radio-opaque by making from it from a radio-opaque material such as tantalum. The stent retainer has a complementary shape that holds the tips on the stent and does not allow the stent to move distally or forward until the outer sheath 151 is fully retracted to the stent retainer 159. The catheter has a side port 156 which allows the space between the inner and outer sheaths to be flushed with saline. The outer sheath 151 and inner sheath 152 may be made from made from a simple single layer polymer extrusion such as from polyethylene or PTFE. The outer sheath 151 may also be constructed in the following manner. The sheath inner diameter surface is constructed of a thin wall PTFE liner 157. A layer of reinforcement 158 is placed over the PTFE liner 157, the reinforcement may be either a braid of wire or a coil of wire. The wire cross-section can be either round or rectangular. According to various embodiments, the wire is made from a metal such as 316 or 304 stainless steel or Nitinol or other suitable material. The wire diameters are typically in the 0.0005 inch to 0.010 inch diameter range. The outer jacket material may be reflowed into the reinforcement layer by melting the material and flowing it into the spaces in between the braided wire or the coil wires. The outside diameter of this catheter will range typically from 1 mm to 4 mm. The catheter can be constructed to be an over the wire catheter or a rapid exchange catheter. For a rapid exchange design, the guidewire will enter the central lumen of the distal end of the catheter and exit at point 188. For an over the wire catheter design, the guidewire will enter the central lumen of the distal end of the catheter and exit at point 189.

Figure 52:
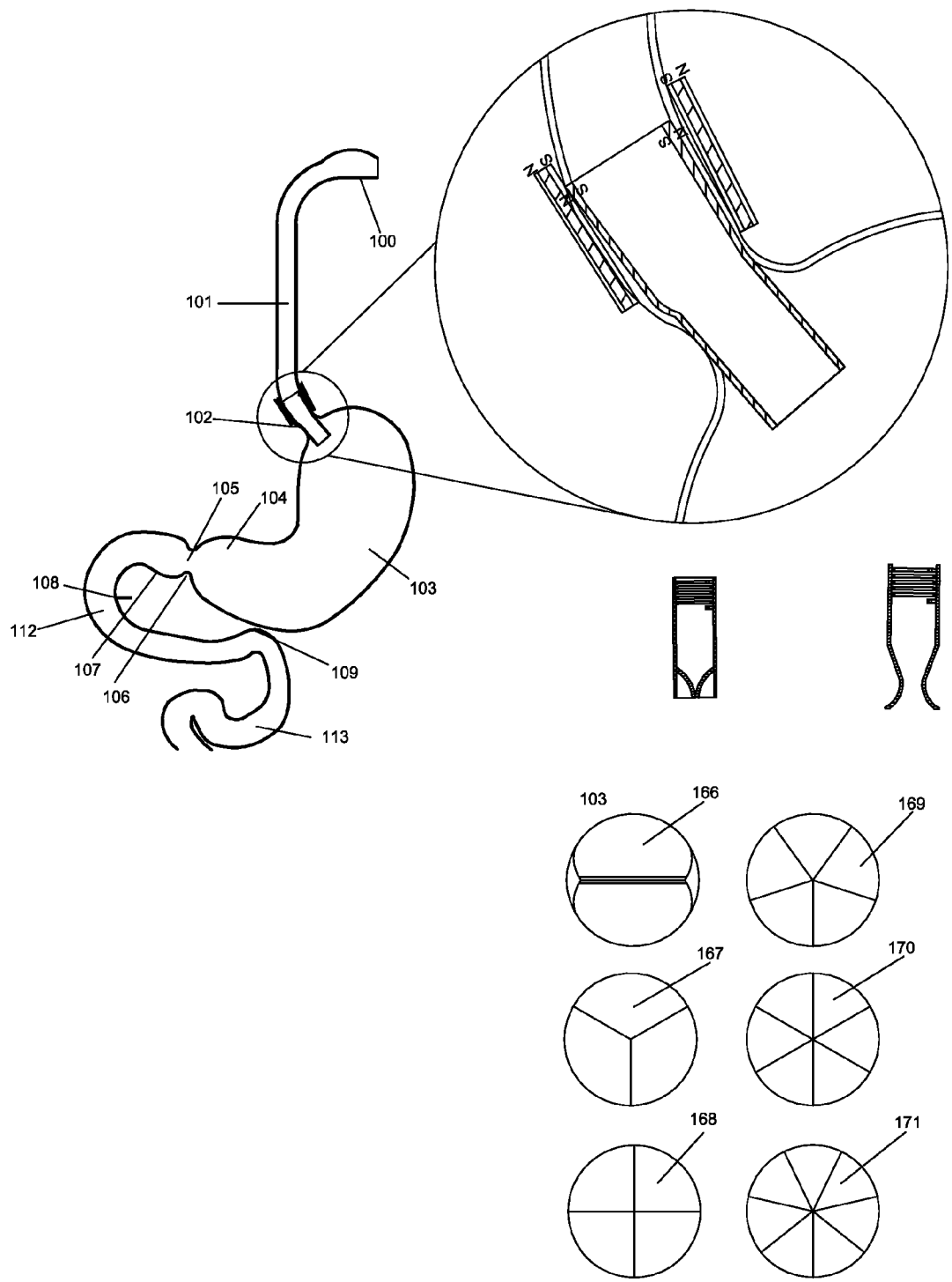
FIG. 52 shows a cross-sectional view of a portion of the digestive tract in the body. An external anchoring device is implanted around the esophagus at the gastro-esophageal junction. An internal tubular implant is implanted at the gastro-esophageal junction. The internal tubular implant can serve the function of an anti-reflux valve or a restrictive stoma.

FIG. 52 is a cross-sectional view of a portion of the digestive tract in the body. An external band is implanted in the esophagus at gastro-esophageal junction 102. An internal tubular implant is attached to the external band. The tubular implant can have bi-leaflet anti-reflux valve 166, a tri-leaflet anti-reflux valve 167, a quad-leaflet anti-reflux valve 168, a penta-leaflet anti-reflux valve 169, a six-leaflet anti-reflux valve 170 or seven-leaflet anti-reflux valve 171. The implant can also be a stoma.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of treating metabolic conditions including diabetes and obesity, the method comprising:
    placing an external implant at a location around at least a portion of a pylorus or a duodenum, the external implant having a docking feature and the external implant having an inner diameter generally equal to an outer diameter of a corresponding portion of the pylorus or the duodenum;
    implanting, using a minimally-invasive technique, an internal tubular implant having a securing feature to a location within the pylorus or the duodenum corresponding to the location of the external implant; and
    removably coupling the securing feature with the docking feature without penetrating the pylorus or the duodenum such that the internal tubular implant resists migration within a gastrointestinal tract.

2. The method of claim 1 wherein the securing feature and the docking feature are each magnetic structures magnetically coupling the internal tubular implant to the external implant.

3. The method of claim 2 wherein the securing feature and the docking feature removably couple the internal tubular implant to the external implant by magnetic attraction.

4. The method of claim 2 wherein the securing feature and the docking feature removably couple the internal tubular implant to the external implant by magnetic repulsion.

5. The method of claim 1 wherein the securing feature and the docking feature are mechanical elements that interlock across a duodenum without penetrating the pylorus.

6. The method of claim 1 wherein the placing includes interlocking the external implant with an anatomical structure at or near the pylorus or the duodenum.

7. The method of claim 5 wherein a diameter of the coupling feature of the external implant is mechanically adjustable.

8. The method of claim 7 wherein a diameter of the coupling feature of the external implant is adjustable using an inflatable member.

9. The method of claim 1 wherein the internal tubular implant extends within the duodenum such that a distal end of the internal tubular implant is located proximal or distal to a ligament of Treitz.

10. The method of claim 1 wherein the securing feature is a stent.

11. The method of claim 1 wherein the docking feature is a metal band.

12. The method of claim 1 wherein the docking feature is a fabric or elastomeric band.

13. A method of treating metabolic conditions including diabetes and obesity, the method comprising:
    placing an external implant at a location around at least a portion of a pylorus or a duodenum, the external implant having a docking feature and the external implant having an inner diameter generally equal to an outer diameter of a corresponding portion of the pylorus or the duodenum;

implanting, using a minimally-invasive technique, an internal tubular implant having a securing feature to a location within the pylorus or the duodenum corresponding to the location of the external implant; and removably coupling the securing feature with the docking feature without penetrating the pylorus or the duodenum such that the internal tubular implant resists migration within a gastrointestinal tract;

wherein the securing feature and the docking feature are each magnetic structures magnetically coupling the internal tubular implant to the external implant.

14. The method of claim 13 wherein the securing feature and the docking feature removably couple the internal tubular implant to the external implant by magnetic attraction.

15. The method of claim 13 wherein the securing feature and the docking feature removably couple the internal tubular implant to the external implant by magnetic repulsion.

16. The method of claim 13 wherein the internal tubular implant extends within the duodenum such that a distal end of the internal tubular implant is located proximal or distal to a ligament of Treitz.

\* \* \* \* \*